US012577288B2

(12) United States Patent
Wong et al.

(10) Patent No.: US 12,577,288 B2
(45) Date of Patent: Mar. 17, 2026

(54) METHODS AND COMPOSITIONS RELATING TO CHIMERIC ANTIGEN RECEPTORS

(71) Applicant: TRUSTEES OF BOSTON UNIVERSITY, Boston, MA (US)

(72) Inventors: Wilson W. Wong, Brookline, MA (US); Jang Hwan Cho, Chestnut Hill, MA (US)

(73) Assignee: TRUSTEES OF BOSTON UNIVERSITY

( * ) Notice: Subject to any disclaimer, the term of this patent is extended or adjusted under 35 U.S.C. 154(b) by 506 days.

(21) Appl. No.: 18/053,432

(22) Filed: Nov. 8, 2022

(65) Prior Publication Data

US 2023/0203123 A1     Jun. 29, 2023

Related U.S. Application Data

(63) Continuation of application No. 15/778,346, filed as application No. PCT/US2016/063257 on Nov. 22, 2016, now Pat. No. 11,530,252.

(60) Provisional application No. 62/258,712, filed on Nov. 23, 2015.

(51) Int. Cl.
| | |
|---|---|
| *C07K 16/46* | (2006.01) |
| *A61K 40/11* | (2025.01) |
| *A61K 40/31* | (2025.01) |
| *A61K 40/42* | (2025.01) |
| *C07K 14/315* | (2006.01) |
| *C07K 14/47* | (2006.01) |
| *C07K 14/705* | (2006.01) |
| *C07K 14/725* | (2006.01) |
| *C07K 16/00* | (2006.01) |
| *C07K 16/18* | (2006.01) |
| *C07K 16/28* | (2006.01) |
| *C07K 16/30* | (2006.01) |
| *C07K 16/32* | (2006.01) |
| *C12N 5/0783* | (2010.01) |
| *C12N 9/90* | (2006.01) |

(52) U.S. Cl.
CPC .......... *C07K 14/7051* (2013.01); *A61K 40/11* (2025.01); *A61K 40/31* (2025.01); *A61K 40/4205* (2025.01); *C07K 14/315* (2013.01); *C07K 14/4738* (2013.01); *C07K 14/70521* (2013.01); *C07K 14/70578* (2013.01); *C07K 16/00* (2013.01); *C07K 16/18* (2013.01); *C07K 16/28* (2013.01); *C07K 16/30* (2013.01); *C07K 16/32* (2013.01); *C12N 5/0636* (2013.01); *C12N 9/90* (2013.01); *A61K 2239/29* (2023.05); *C07K 2317/622* (2013.01); *C07K 2317/92* (2013.01); *C07K 2319/02* (2013.01); *C07K 2319/03* (2013.01); *C07K 2319/70*

(2013.01); *C07K 2319/73* (2013.01); *C07K 2319/80* (2013.01); *C07K 2319/81* (2013.01)

(58) Field of Classification Search
None
See application file for complete search history.

(56) References Cited

U.S. PATENT DOCUMENTS

2016/0185862 A1     6/2016  Wu et al.

FOREIGN PATENT DOCUMENTS

| | | |
|---|---|---|
| WO | 2012/082841 A2 | 6/2012 |
| WO | 2014/127261 A1 | 8/2014 |
| WO | 2015017214 A1 | 2/2015 |

OTHER PUBLICATIONS

Acharya et al., "Experimental identification of homodimerizing B-ZIP families in *Homo sapiens*." Journal of Structural Biology 155(2):130-139 (2006).

Andreeva et al. "SCOP2 prototype: a new approach to protein structure mining." Nucleic Acids Research 42(D1):D310-D314 (2014).

Behncken et al., "Growth hormone (GH)-independent dimerization of GH receptor by a leucine zipper results in constitutive activation", J Biol Chem., 275(22):17000-17007 (2000).

Brentjens et al. "CD19-targeted T cells rapidly induce molecular remissions in adults with chemotherapy-refractory acute lymphoblastic leukemia", Sci Transl Med., 5(177):177ra38 (2013).

Cho et al. "Universal Chimeric Antigen Receptors for Multiplexed and Logical Control of T Cell Responses." Cell 173(6): 1426-1438. e11 (2018).

Fedorov et al., "PD-1-and CTLA-4-based inhibitory chimeric antigen receptors (iCARs) divert off-target immunotherapy responses." Science Translational Medicine 5(215):215ra172 (2013).

Grada et al., "TanCAR: a novel bispecific chimeric antigen receptor for cancer immunotherapy." Molecular Therapy—Nucleic Acids 2:e105 (2013).

Juillerat et al., "Design of chimeric antigen receptors with integrated controllable transient functions." Scientific Reports 6:18950 (2016).

Kloss et al., "Combinatorial antigen recognition with balanced signaling promotes selective tumor eradication by engineered T cells." Nature Biotechnology 31(1):71-75 (2013).

Kudo et al., "T lymphocytes expressing a CD16 signaling receptor exert antibody-dependent cancer cell killing", Cancer Res., 74(1):93-103 (2013).

(Continued)

*Primary Examiner* — Michael D Pak
(74) *Attorney, Agent, or Firm* — NIXON PEABODY LLP; Ronald I. Eisenstein; Nicole D. Kling

(57) ABSTRACT

Described herein is a chimeric antigen receptor (CAR) platform with the ability to (a) serve as an ON/OFF switch (with the ability for tenability/titrability), (b) sense multiple antigens and perform logic computations, and/or (c) independently regulate multiple signaling pathways. The compositions provided herein permit the degree of control and discrimination necessary to optimize CAR T cell therapy. Also described herein are cells comprising such compositions and the use of these compositions and/or cells in the treatment of cancer.

8 Claims, 34 Drawing Sheets

Specification includes a Sequence Listing.

(56) References Cited

OTHER PUBLICATIONS

Lanitis et al., "Chimeric antigen receptor T cells with dissociated signaling domains exhibit focused antitumor activity with reduced potential for toxicity in vivo." Cancer Immunology Research 1(1):43-53 (2013).

Li et al. "A novel variable antibody fragment dimerized by leucine zippers with enhanced neutralizing potency against rabies virus G protein compared to its corresponding single-chain variable antibody fragment." Molecular immunology 68(2): 168-175 (2015).

Ma et al., "Versatile strategy for controlling the specificity and activity of engineered T cells." PNAS 113(4):E450-E458 (2016).

Mali et al., "Barcoding cells using cell-surface programmable DNA-binding domains" Nat Methods., 10(5):403-406 (2013).

Morsut et al., "Engineering customized cell sensing and response behaviors using synthetic notch receptors." Cell 164(4):780-791 (2016).

Odahara. "Stability and solubility of integral membrane proteins from photosynthetic bacteria solubilized in different detergents." Biochimica et Biophysica Acta (BBA)-Biomembranes 1660(1-2): 80-92 (2004).

Reinke et al. "A synthetic coiled-coil interactome provides heterospecific modules for molecular engineering." Journal of the American Chemical Society 132(17): 6025-6031 (2010).

Rodgers et al., "Switch-mediated activation and retargeting of CAR-T cells for B-cell malignancies." PNAS 113(4):E459-E468 (2016).

Roybal et al., "Precision tumor recognition by T cells with combinatorial antigen-sensing circuits." Cell 164(4):770-779 (2016).

Tameda et al. "Redirecting Gene-Modified T Cells toward Various Cancer Types Using Tagged Antibodies." Clinical Cancer Research 18(23): 6436-6445 (2012).

Urbanska et al., "A universal strategy for adoptive immunotherapy of cancer through use of a novel T-cell antigen receptor", Cancer Res., 72(7):1844-1852 (2012).

Wei et al., "Design space for complex DNA structures", J Am Chem Soc., 135(48):18080-18088 (2013).

Wu et al., "Remote control of therapeutic T cells through a small molecule-gated chimeric receptor." Science 350 (6258):aab4077 (2015).

Ye et al., "Synthetic therapeutic gene circuits in mammalian cells." FEBS Letters 588(15):2537-2544 (2014).

Zah et al., "T cells expressing CD19/CD20 bi-specific chimeric antigen receptors prevent antigen escape by malignant B cells." Cancer Immunology Research 4:498-508 (2016).

zipCAR LOGIC COMPUTATION

| Axl | Her2 | T cell act. |
|-----|------|-------------|
| 0 | 0 | 0 |
| 0 | 1 | 0 |
| 1 | 0 | 1 |
| 1 | 1 | 0 |

NOT gate

Weak interactions
between zipCAR
and two scFv fused
leucin zipper pairs

| Axl | Her2 | T cell act. |
|-----|------|-------------|
| 0 | 0 | 0 |
| 0 | 1 | 0 |
| 1 | 0 | 0 |
| 1 | 1 | 1 |

AND gate zipCAR ORTHOGONAL CONTROL of SIGNALING

| LOGIC GATE | | Truth Table | | | SUPRA Design | | |
| NAME | SYMBOL | IN | | OUT | ZipCAR | αHer2-ZipFv | αAxl-ZipFv |
| | | A Her2 | B Axl | T cel Act. | | | |
| FALSE | 1 | 0<br>1<br>0<br>1 | 0<br>0<br>1<br>1 | 0<br>0<br>0<br>0 | BZip1-CAR | | |
| A | A | 0<br>1<br>0<br>1 | 0<br>0<br>1<br>1 | 0<br>1<br>0<br>1 | BZip1-CAR | αHer2-AZip1 | |
| B | B | 0<br>1<br>0<br>1 | 0<br>0<br>1<br>1 | 0<br>0<br>1<br>1 | BZip1-CAR | | αAxl-AZip1 |
| OR | A B | 0<br>1<br>0<br>1 | 0<br>0<br>1<br>1 | 0<br>1<br>1<br>1 | BZip1-CAR | αHer2-AZip1 | αAxl-AZip1 |
| A NIMPLY B | A B | 0<br>1<br>0<br>1 | 0<br>0<br>1<br>1 | 0<br>1<br>0<br>0 | BZip1-CAR | αHer2-AZip1 | αAxl-BZip1 -weak |
| B NIMPLY A | A B | 0<br>1<br>0<br>1 | 0<br>0<br>1<br>1 | 0<br>0<br>1<br>0 | BZip1-CAR | αHer2-BZip1 -weak | αAxl-AZip1 |
| AND | A B | 0<br>1<br>0<br>1 | 0<br>0<br>1<br>1 | 0<br>0<br>0<br>1 | BZip2-BZip1-CAR | αHer2-PDZ-BZip1weak | αAxl-PL-BZip1weak |
| XOR | A B | 0<br>1<br>0<br>1 | 0<br>0<br>1<br>1 | 0<br>1<br>1<br>0 | BZip2-BZip1-CAR | αHer2-AZip1 BZip2-weak | αAxl-BZip1 -weak-AZip2 |

FIG. 16

| Set | zipCARs | | | Phenotype |
|---|---|---|---|---|
| | A | B | C | |
| 1 | CD3z | CD28 | 4-1BB | (A AND B) will has faster tumoricidal kinetics while (A AND C) will have longer persistence |
| 2 | CD3z | CD28 | PD-1 | (A AND B) will has faster tumoricidal kinetics while C can inhibit T cell activation |

METHODS AND COMPOSITIONS RELATING TO CHIMERIC ANTIGEN RECEPTORS

CROSS-REFERENCE TO RELATED APPLICATIONS

This application is a continuation under 35 U.S.C. § 120 of co-pending U.S. application Ser. No. 15/778,346 filed May 23, 2018, which is a 35 U.S.C. § 371 National Phase Entry Application of International Application No. PCT/US2016/063257 filed Nov. 22, 2016, which designates the U.S. and claims benefit under 35 U.S.C. § 119(e) of U.S. Provisional Application No. 62/258,712 filed Nov. 23, 2015, the contents of which are incorporated herein by reference in their entireties.

GOVERNMENT SUPPORT

This invention was made with Government Support under Contract No. CA186574 awarded by the National Institutes of Health. The Government has certain rights in the invention.

SEQUENCE LISTING

The instant application contains a Sequence Listing which has been filed electronically in XML format and is hereby incorporated by reference in its entirety. Said XML copy, created on Oct. 25, 2022, is named 701586-082751USC1_SL.xml and is 5,065 bytes in size.

TECHNICAL FIELD

The technology described herein relates to chimeric antigen receptors (CAR), e.g. multi-component CARs.

BACKGROUND

One approach to treating cancer is immunotherapy, an approach in which, instead of providing a drug that is toxic to cancer cells, the patient is provided a therapy that encourages the body's own immune system to more effectively attack the cancer itself. T cells are the part of the immune system that are responsible for recognizing the presence of a foreign or diseased cell in the body and either killing the diseased cell or recruiting the assistance of other immune cells to accomplish that goal.

T cells recognize their target cells by using receptors on their cell surface which are called T Cell Receptors (TCRs). TCRs have a recognition portion and a signaling portion. When the recognition portion binds to the natural complexes formed in the body in the presence of a diseased cell, the signaling portion is activated, which leads to the T cell engaging in killing activity or recruiting other immune cells to destroy the diseased cell.

A therapy called "CAR-T" seeks to help T cells recognize cancer cells. This is accomplished by genetically altering a T cell so that it expresses a chimeric antigen receptor (CAR). The CAR is an altered TCR, in which the natural recognition portion is removed and replaced with a synthetic recognition portion that is designed to more effectively recognize the cancer cells by very specifically detecting the presence of a molecule unique to the cancer cells (e.g. a cancer cell marker). These CAR-T cells are then given to a cancer patient. Inside the patient, their synthetic CAR molecules will bind to the cancer cells that express the marker and in the act of that binding, activate the T cell, resulting in the patient's own immune system attacking the cancer.

SUMMARY

While traditional CAR-T is a powerful tool, it is significantly lacking in flexibility. For example, once the CAR-T cell is administered, it will activate the immune system as soon as it finds a cancer cell and the activation will continue until the cancer is eradicated or the T cells die. In some patients, it may be desirable to delay or turn off the immune system activation, e.g., if the immune system activity is causing side effects or another therapy is to be administered. Addtionally, CAR-T is limited to recognition of a single marker on the cancer cells. Use of multiple markers requires multiple different CARs and once the cell is altered and given to the patient, it is not possible to change which markers and how many markers it recognizes.

Described herein is an improvement of CAR-T technology which relates to multi-component CARs. In a multi-component CAR, the signaling and recognition portions of the CAR are separated and present as two different polypeptides. The recognition portion of the multi-component CAR, on its own, can bind to a cancer cell marker, but not activate a T cell. The signaling portion of the multi-component CAR, on its own, cannot be turned on and thus does not activate the T cell. However, when a recognition poypeptide and a signaling polypeptide are present together, they can bind to each other and then function as a complete CAR.

This change in the structure of the CAR makes the CAR much more flexible. For instance, if the T cell is altered to have just a signaling portion of the multi-component CAR and then given to the subject, a physician can provide the recognition portion of the multi-component CAR as a separate drug, allowing the physician to control when and for how long the immune system activates. Additionally, if the use of a particular cancer cell marker turns out to be ineffective or counterproductive, the physician can switch to use of a second recognition polypeptide merely by administering a new recognition polypeptide. This is in contrast to traditional CAR-T, which would require that entirely new CAR-T cells be engineered and/or force the patient to wait out side effects caused by the original CAR-T cells.

Additionally, described herein are multi-component CARs that make very advanced therapies possible. For example, the technology described herein, by using multiple recognition molecules, can provide the immune system with instructions to activate if they recognize either marker 1 or marker 2. Alternatively, instructions can be provided to the immune system to activate if marker 1 (which is found on cancer cells) is recognized but not if marker 3 (which is found on healhy cells) is recognized in the same location. This ability to perform logical computations allows CAR-T therapy to be adjusted to the needs of individual patients quickly at much lower cost, and in ways that are not possible with traditional CAR-T therapies.

In one aspect of any of the embodiments, described herein is a composition comprising a multi-component chimeric antigen receptor (CAR); the multi-component CAR comprising: a) a first recognition polypeptide comprising 1) an antibody reagent specific for a first target ligand and 2) a protein interaction domain; and b) a signaling polypeptide comprising 1) an extracellular protein interaction domain that can bind specifically with the protein interaction domain of the first recognition polypeptide and 2) an intracellular T cell receptor (TCR) signaling domain. In some embodiments of any of the aspects, the protein interaction domains are leucine zipper domains. In some embodiments of any of the aspects, one leucine zipper domain is BZip (RR) and the second leucine zipper domain is AZip (EE). In some embodiments of any of the aspects, the protein interaction domains are PSD95-Dlg1-zo-1 (PDZ) domains. In some embodiments of any of the aspects, one protein interaction domain is streptavidin and a second protein interaction domain is streptavidin binding protein (SBP). In some embodiments of any of the aspect, one protein interaction domain is FKBP-binding domain of mTOR (FRB) and a second protein interaction domain is FK506 binding protein (FKBP); one protein interaction domain is cyclophilin-Fas fusion protein (CyP-Fas) and a second protein interaction domain is FK506 binding protein (FKBP); one protein interaction domain is calcineurinA (CNA) and a second protein interaction domain is FK506 binding protein (FKBP); one protein interaction domain is gibberellin insensitive (GIA) and a second protein interaction domain is gibberellin insensitive dwarf1 (GID1); one protein interaction domain is Snap-tag and a second protein interaction domain is Halo tag; or one protein interaction domain is T14-3-3-cdeltaC and a second protein interaction domain is C-Terminal peptides of PMA2 (CT52). In some embodiments of any of the aspects, one protein interaction domain is PYL and a second protein interaction domain is ABI. In some embodiments of any of the aspects, one protein interaction domain is a nucleotide tag and the second protein interaction domain is a zinc finger domain. In some embodiments of any of the aspects, the protein interaction domain of the recognition polypeptide is a nucleotide tag and the extracellular protein interaction domain of the signaling polypeptide is a zinc finger domain. In some embodiments of any of the aspects, the nucleotide tag is a DNA tag. In some embodiments of any of the aspects, the DNA tag is a dsDNA tag.

In some embodiments of any of the aspects, the compositions further comprise a second recognition polypeptide comprising 1) an antibody reagent specific for a second target ligand and 2) a protein interaction domain that competes with the protein interaction domain of the signaling polypeptide for binding to the protein interaction domain of the first recognition polypeptide. In some embodiments of any of the aspects, the protein interaction domain of the second recognition polypeptide and the protein interaction domain of the first recognition polypeptide have a greater affinity than the protein interaction domain of the signaling polypeptide and the protein interaction domain of the first recognition polypeptide. In some embodiments of any of the aspects, the target ligand recognized by the second recognition polypeptide is found on a healthy and/or non-target cell and not on a diseased and/or target cell.

In some embodiments of any of the aspects, the composition further comprises a second recognition polypeptide comprising 1) an antibody reagent specific for a second target ligand and 2) a protein interaction domain; and the signaling polypeptide further comprises a secondary protein interaction domain that specifically binds with the protein interaction domain of the second recognition polypeptide. In some embodiments of any of the aspects, the affinity of the signaling polypeptide's secondary protein interaction domain and the protein interaction domain of the second recognition polypeptide is weaker than the affinity of the signaling polypeptide's first protein interaction domain and the protein interaction domain of the first recognition polypeptide. In some embodiments of any of the aspects, the first and second recognition polypeptides each comprise a secondary protein interaction domain; and the secondary protein interaction domains specifically bind to each other.

In one aspect of any of the embodiments, described herein is a composition comprising a multi-component chimeric antigen receptor (CAR); the multi-component CAR comprising: a) a first recognition polypeptide comprising 1) an antibody reagent specific for a first target ligand and 2) a first portion of a nucleotide tag; b) a second recognition polypeptide comprising 1) an antibody reagent specific for a second target ligand and 2) a second portion of the nucleotide tag; and c) a signaling polypeptide comprising 1) an extracellular zinc finger domain that can bind specifically with a complete nucleotide tag formed by the association of the individual portions of the nucleotide tag and 2) an intracellular T cell receptor (TCR) signaling domain; wherein the individual portions of the nucleotide tag cannot be specifically bound by the zinc finger domain unless they are associated with each other. In some embodiments of any of the aspects, the first portion of the nucleotide tag is a ssDNA and the second portion of the nucleotide tag is a complementary ssDNA. In some embodiments of any of the aspects, the composition further comprises a third recognition polypeptide encoding 1) an antibody reagent specific for a third target ligand and 2) a third portion of the nucleotide tag; wherein the individual portions or pairwise combinations individual portions of the nucleotide tag cannot be specifically bound by the zinc finger domain, but when all three portions are associated with each other, the resulting complex can be specifically bound by the zinc finger domain. In some embodiments of any of the aspects, 1) the first portion of the nucleotide tag is a ssDNA; and 2) the second and third portions of the nucleotide tag are ssDNAs, each of which is complementary to the first portion and 3) the second and third portions of the nucleotide tag have sequences that do not overlap with each other.

In one aspect of any of the embodiments, described herein is a composition comprising a multi-component chimeric antigen receptor (CAR); the multi-component CAR comprising: a) a first recognition polypeptide comprising 1) an antibody reagent specific for a first target ligand and 2) a first nucleotide tag; b) a second recognition polypeptide comprising 1) an antibody reagent specific for a second target ligand and 2) a second nucleotide tag; and c) a signaling polypeptide comprising 1) an extracellular zinc finger domain that can bind specifically with the first nucleotide tag and 2) an intracellular T cell receptor (TCR) signaling domain; wherein the nucleotide tags cannot be specifically bound by the zinc finger domain when they are associated with each other. In some embodiments of any of the aspects, the first nucleotide tag forms a hairpin-loop structure and wherein the second nucleotide tag is complementary to a portion of the first nucleotide tag that encompasses a portion of one leg of the hairpin-loop and a portion of the loop of the hairpin-loop. In some embodiments of any of the aspects, the second target ligand is found on a healthy and/or non-target cell and not on a diseased and/or target cell.

In some embodiments of any of the aspects, a target ligand is a ligand found on a diseased and/or target cell. In some embodiments of any of the aspects, the target ligand specifically bound by a recognition polypeptide that can specifically bind with a signaling polypeptide is a ligand found on a diseased and/or target cell. In some embodiments of any of the aspects, the target ligand specifically bound by a recognition polypeptide that can specifically bind with a signaling polypeptide is a ligand found on a diseased and/or target cell and not on a healthy and/or non-target cell. In some embodiments of any of the aspects, the diseased cell is a cancerous cell.

In some embodiments of any of the aspects, the antibody reagent is selected from the group consisting of an immunoglobulin molecule, a monoclonal antibody, a chimeric antibody, a CDR-grafted antibody, a human antibody, a humanized antibody, a Fab, a Fab', a F(ab')2, a Fv, a disulfide linked Fv, a scFv, a single domain antibody, a diabody, a multispecific antibody, a dual specific antibody, an anti-idiotypic antibody, and a bispecific antibody. In some embodiments of any of the aspects, the intracellular TCR signaling domain is a signaling domain from a protein selected from the group consisting of: TCRζ, FcRγ, FcRβ, CD3γ, CD3δ, CD3ε, CD3ζ, CD22, CD79a, CD79b, CD66d, CARD11, CD2, CD7, CD27, CD28, CD30, CD40, CD54 (ICAM), CD83, CD134 (OX40), CD137 (4-1BB), CD150 (SLAMF1), CD152 (CTLA4), CD223 (LAG3), CD270 (HVEM), CD273 (PD-L2), CD274 (PD-L1), CD278 (ICOS), DAP10, LAT, NKD2C SLP76, TRIM, ZAP70, and 41BB.

In some embodiments of any of the aspects, the composition further comprises second multi-component CAR according to any of the embodiments. In some embodiments of any of the aspects, the antibody reagents of the second multi-component CAR bind specifically to different target ligands than those bound by the antibody reagents of the first multi-component CAR. In some embodiments of any of the aspects, the intracellular T cell receptor (TCR) signaling domain of the second multi-component CAR inhibits T cell activity. In some embodiments of any of the aspects, the intracellular T cell receptor (TCR) signaling domain of the second multi-component CAR which inhibits T cell activity comprises a signaling domain of a polypeptide selected from the group consisting of: PD1; CTLA4; BTLA; KIR; LAG-3; TIM-3; A2aR; LAIR-1; and TGIT. In some embodiments of any of the aspects, the target ligand specifically bound by a recognition polypeptide that can specifically bind with the signaling polypeptide of the second multi-component CAR is a ligand found on a healthy and/or non-target cell. In some embodiments of any of the aspects, the target ligand specifically bound by a recognition polypeptide that can specifically bind with the signaling polypeptide of the second multi-component CAR is a ligand found on a healthy and/or non-target cell and not on a diseased and/or target cell.

In some embodiments of any of the aspects, the signaling polypeptide is present on the membrane of a cell. In some embodiments of any of the aspects, the one or more recognition polypeptides are present in the extracellular space.

In one aspect of any of the embodiments, described herein is an engineered cell expressing the composition of any of the foregoing embodiments. In one aspect of any of the emobdiments, described herein is an engineered cell comprising a nucleic acid sequence encoding the composition of any of the foregoing embodiments. In some embodiments of any of the aspects, the cell is a T cell, NK cell, or NKT cell. In some embodiments of any of the aspects, the cell is a T cell.

In one aspect of any of the embodiments, described herein is a method of killing a target cell, the method comprising contacting the cell with a composition or cells of any of the foregoing embodiments. In one aspect of any of the embodiments, described herein is a method of treating a disease, comprising administering a composition or cells of any of the foregoing embodiments to a subject in need of treatment thereof. In some embodiments of any of the aspects, the disease is selected from the group consisting of:

cancer; solid cancers; breast cancer; lung cancer; acute lymphoblastic leukemia; multiple myeloma; and refractory multiple myeloma. In one aspect of any of the embodiments, described herein is a method of treating cancer, comprising administering a composition or cells of any of the foregoing embodiments to a subject in need of treatment thereof. In some embodiments of any of the aspects, the cell is autologous to the subject. In some embodiments of any of the aspects, the administered cell is derived and/or descended from a cell obtained from the subject and has been modified ex vivo to comprise the at least one multi-component CAR.

In one aspect of any of the embodiments, described herein is an engineered cell comprising a multi-component chimeric antigen receptor (CAR) signaling polypeptide, the signaling polypeptide comprising 1) an extracellular protein interaction domain and 2) an intracellular T cell receptor (TCR) signaling domain. In some embodiments of any of the aspects, the protein interaction domain is a leucine zipper domain. In some embodiments of any of the aspects, the leucine zipper domain is BZip (RR) or AZip (EE). In some embodiments of any of the aspects, the protein interaction domain is a PSD95-Dlg1-zo-1 (PDZ) domain. In some embodiments of any of the aspects, the protein interaction domain is streptavidin or streptavidin binding protein (SBP). In some embodiments of any of the aspects, the protein interaction domain is FKBP-binding domain of mTOR (FRB) or FK506 binding protein (FKBP). In some embodiments of any of the aspects, the protein interaction domain is PYL or ABI. In some embodiments of any of the aspects, the protein interaction domain is a nucleotide tag or a zinc finger domain. In some embodiments of any of the aspects, the nucleotide tag is a DNA tag. In some embodiments of any of the aspects, the DNA tag is a dsDNA tag. In some embodiments of any of the aspects, the protein interaction domain is a zinc finger domain. In some embodiments of any of the aspects, the signaling polypeptide is present on the membrane of the cell. In some embodiments of any of the aspects, the cell is a T cell, NK cell, or NKT cell. In some embodiments of any of the aspects, the cell is a T cell. In some embodiments of any of the aspects, the intracellular TCR signaling domain is a signaling domain from a protein selected from the group consisting of: TCRζ, FcRγ, FcRβ, CD3γ, CD3δ, CD3ε, CD3ζ, CD22, CD79a, CD79b, CD66d, CARD11, CD2, CD7, CD27, CD28, CD30, CD40, CD54 (ICAM), CD83, CD134 (OX40), CD137 (4-1BB), CD150 (SLAMF1), CD152 (CTLA4), CD223 (LAG3), CD270 (HVEM), CD273 (PD-L2), CD274 (PD-L1), CD278 (ICOS), DAP10, LAT, NKD2C SLP76, TRIM, ZAP70, and 41BB. In some embodiments of any of the aspects, the signaling polypeptide further comprises a secondary protein interaction domain that specifically binds with the protein interaction domain of the second recognition polypeptide. In some embodiments of any of the aspects, the cell further comprises a second multi-component CAR signaling peptide according to any of the embodiments.

In one aspect of any of the embodiments, described herein is a method of treating a disease, the method comprising administering: a cell comprising a multi-component chimeric antigen receptor (CAR) signaling polypeptide; and a first recognition polypeptide comprising 1) an antibody reagent specific for a first target ligand and 2) a protein interaction domain that can bind specifically with the protein interaction domain of the signaling polypeptide; to a subject in need of treatment therefor. In some embodiments of any of the aspects, the antibody reagent is selected from the group consisting of: an immunoglobulin molecule, a monoclonal antibody, a chimeric antibody, a CDR-grafted antibody, a human antibody, a humanized antibody, a Fab, a Fab', a F(ab')2, a Fv, a disulfide linked Fv, a scFv, a single domain antibody, a diabody, a multispecific antibody, a dual specific antibody, an anti-idiotypic antibody, and a bispecific antibody. In some embodiments of any of the aspects, the cell is autologous to the subject. In some embodiments of any of the aspects, the administered cell is derived and/or descended from a cell obtained from the subject and has been modified ex vivo to comprise the at least one multi-component CAR. In some embodiments of any of the aspects, the protein interaction domains are leucine zipper domains. In some embodiments of any of the aspects, one leucine zipper domain is BZip (RR) and the second leucine zipper domain is AZip (EE). In some embodiments of any of the aspects, the protein interaction domains are PSD95-Dlg1-zo-1 (PDZ) domains. In some embodiments of any of the aspects, one protein interaction domain is streptavidin and a second protein interaction domain is streptavidin binding protein (SBP). In some embodiments of any of the aspects, one protein interaction domain is FKBP-binding domain of mTOR (FRB) and a second protein interaction domain is FK506 binding protein (FKBP); one protein interaction domain is cyclophilin-Fas fusion protein (CyP-Fas) and a second protein interaction domain is FK506 binding protein (FKBP); one protein interaction domain is calcineurinA (CNA) and a second protein interaction domain is FK506 binding protein (FKBP); one protein interaction domain is gibberellin insensitive (GIA) and a second protein interaction domain is gibberellin insensitive dwarf1 (GID1); one protein interaction domain is Snap-tag and a second protein interaction domain is Halo tag; or one protein interaction domain is T14-3-3-cdeltaC and a second protein interaction domain is C-Terminal peptides of PMA2 (CT52). In some embodiments of any of the aspects, when one protein interaction domain is FKBP-binding domain of mTOR (FRB) and a second protein interaction domain is FK506 binding protein (FKBP), the method further comprises administering tacrolimus, a rapalog, or everolimus; when one protein interaction domain is cyclophilin-Fas fusion protein (CyP-Fas) and a second protein interaction domain is FK506 binding protein (FKBP), the method further comprises administering FKCsA; when one protein interaction domain is calcineurinA (CNA) and a second protein interaction domain is FK506 binding protein (FKBP), the method further comprises administering FK506; one protein interaction domain is gibberellin insensitive (GIA) and a second protein interaction domain is gibberellin insensitive dwarf1 (GID1), the method further comprises administering gibberellin; when one protein interaction domain is Snap-tag and a second protein interaction domain is Halo tag, the method further comprises administering HaXS; or when one protein interaction domain is T14-3-3-cdeltaC and a second protein interaction domain is C-Terminal peptides of PMA2 (CT52), the method further comprises administering fusicoccin. In some embodiments of any of the aspects, one protein interaction domain is PYL and a second protein interaction domain is ABI. In some embodiments of any of the aspects, the protein interaction domain of the recognition polypeptide is a nucleotide tag and the extracellular protein interaction domain of the signaling polypeptide is a zinc finger domain. In some embodiments of any of the aspects, the nucleotide tag is a DNA tag. In some embodiments of any of the aspects, the DNA tag is a dsDNA tag. In some embodiments of any of the aspects, the method further comprises administering a second recognition polypeptide comprising 1) an antibody reagent specific for a second target ligand and 2) a protein interaction domain that competes with the protein interaction domain of the signaling polypeptide for binding to the protein interaction domain of the first recognition polypeptide. In some embodiments of any of the aspects, the protein interaction domain of the second recognition polypeptide and the protein interaction domain of the first recognition polypeptide have a greater affinity than the protein interaction domain of the signaling polypeptide and the protein interaction domain of the first recognition polypeptide. In some embodiments of any of the aspects, the target ligand recognized by the second recognition polypeptide is found on a healthy and/or non-target cell and not on a diseased and/or target cell.

In some embodiments of any of the aspects, the method further comprises administering a second recognition polypeptide comprising 1) an antibody reagent specific for a second target ligand and 2) a protein interaction domain; and the signaling polypeptide further comprises a secondary protein interaction domain that specifically binds with the protein interaction domain of the second recognition polypeptide. In some embodiments of any of the aspects, the affinity of the signaling polypeptide's secondary protein interaction domain and the protein interaction domain of the second recognition polypeptide is weaker than the affinity of the signaling polypeptide's first protein interaction domain and the protein interaction domain of the first recognition polypeptide. In some embodiments of any of the aspects, the first and second recognition polypeptides each comprise a secondary protein interaction domain; and wherein the secondary protein interaction domains specifically bind to each other.

In some embodiments of any of the aspects, the method comprises administering a) a first recognition polypeptide comprising 1) an antibody reagent specific for a first target ligand and 2) a first portion of a nucleotide tag; b) a second recognition polypeptide comprising 1) an antibody reagent specific for a second target ligand and 2) a second portion of the nucleotide tag; wherein the signaling polypeptide comprises 1) an extracellular zinc finger domain that can bind specifically with a complete nucleotide tag formed by the association of the individual portions of the nucleotide tag; and wherein the individual portions of the nucleotide tag cannot be specifically bound by the zinc finger domain unless they are associated with each other. In some embodiments of any of the aspects, the first portion of the nucleotide tag is a ssDNA and the second portion of the nucleotide tag is a complementary ssDNA. In some embodiments of any of the aspects, the method further comprises administering a third recognition polypeptide encoding 1) an antibody reagent specific for a third target ligand and 2) a third portion of the nucleotide tag; wherein the individual portions or pairwise combinations individual portions of the nucleotide tag cannot be specifically bound by the zinc finger domain, but when all three portions are associated with each other, the resulting complex can be specifically bound by the zinc finger domain. In some embodiments of any of the aspects, 1) the first portion of the nucleotide tag is a ssDNA; and 2) the second and third portions of the nucleotide tag are ssDNAs, each of which is complementary to the first portion and 3) the second and third portions of the nucleotide tag have sequences that do not overlap with each other.

In some embodiments of any of the aspects, the method comprises administering: a) a first recognition polypeptide comprising 1) an antibody reagent specific for a first target ligand and 2) a first nucleotide tag; b) a second recognition polypeptide comprising 1) an antibody reagent specific for a second target ligand and 2) a second nucleotide tag; wherein the signaling polypeptide comprises 1) an extracellular zinc finger domain that can bind specifically with the first nucleotide tag; and wherein the nucleotide tags cannot be specifically bound by the zinc finger domain when they are associated with each other. In some embodiments of any of the aspects, the first nucleotide tag forms a hairpin-loop structure and wherein the second nucleotide tag is complementary to a portion of the first nucleotide tag that encompasses a portion of one leg of the hairpin-loop and a portion of the loop of the hairpin-loop. In some embodiments of any of the aspects, the second target ligand is found on a healthy and/or non-target cell and not on a diseased and/or target cell.

In some embodiments of any of the aspects, a target ligand is a ligand found on a diseased and/or target cell. In some embodiments of any of the aspects, the target ligand specifically bound by a recognition polypeptide that can specifically bind with a signaling polypeptide is a ligand found on a diseased and/or target cell. In some embodiments of any of the aspects, the target ligand specifically bound by a recognition polypeptide that can specifically bind with a signaling polypeptide is a ligand found on a diseased and/or target cell and not on a healthy and/or non-target cell. In some embodiments of any of the aspects, the diseased cell is a cancerous cell.

In some embodiments of any of the aspects, the cell comprises a second multi-component CAR signaling polypeptide and the subject is further administered a second recognition polypeptide comprising 1) an antibody reagent specific for a second target ligand and 2) a protein interaction domain that can bind specifically with the protein interaction domain of the second signaling polypeptide. In some embodiments of any of the aspects, the intracellular T cell receptor (TCR) signaling domain of the second multi-component CAR signaling polypeptide inhibits T cell activity. In some embodiments of any of the aspects, the target ligand specifically bound by a recognition polypeptide that can specifically bind with the second signaling polypeptide is a ligand found on a healthy and/or non-target cell. In some embodiments of any of the aspects, the target ligand specifically bound by a recognition polypeptide that can specifically bind with the second signaling polypeptide is a ligand found on a healthy and/or non-target cell and not on a diseased and/or target cell.

BRIEF DESCRIPTION OF THE DRAWINGS

FIG. 1A depicts adoptive immunotherapy using CAR in the clinics. FIG. 1B depicts a comparison of various existing CAR designs. scFv, single-chain antibody. CD3ζ, T cell receptor signaling domain from CD3ζ chain.

FIG. 2A depicts how SUPRA allows integration of multiple antigen signals. FIG. 2B demonstrates that SURPA can be realized using leucine zipper or zinc-finger as the programmable interaction domains.

FIGS. 3A-3C depict leucine zipper CAR design, logic computation and orthogonal control of T cell signaling. FIG. 3A depicts a schematic of leucine zipper CAR design. Leucine zippers that will be used in this project are consisted of an acidic (AZip) and basic (BZip) domain. AZips with different affinity to a BZip are available. FIG. 3B demonstrates that logic computation, such as NOT gates can be created using zipCAR. FIG. 3C demonstrates that zipCAR can be made to bind to orthogonal zipper, thus allow independent control of various T cell signaling pathways.

FIG. 6A demonstrates that each leucine zipper was tested for its own binding as well as other leucine zippers. The zippers were chosen to cover a wide range of affinity and specificity to other zipper. Interactions between leucine zipper pairs in CARs were measured by NFAT transcription activity. Numbering from 1 to 37 refers to different leucine zipper described in previous paper [Reinke et al, (2010)]. Top numbers represent leucine zippers expressed on effector cells and side numbers represent leucine zippers expressed on target cells. FIG. 6B demonstrates that from the data shown in FIG. 6A, three orthogonal pairs were identified. FIG. 6C demonstrates that four more potential pairs of orthogonal zippers were identified from the same set of data. Note that no NFAT activation was observed when effector cells expressing leucine zipper 11 and target cell expressing leucine zipper 33. However, when effector cells expressing leucine zipper 33 and target cell expressing leucine zipper 11 were co-cultured together, high NFAT transcription activity was measured. Potentially, leucine zipper 33 can be used to be expressed on effector cell and use leucine zipper 11 to be fused with scFv that can target cancer cells. FIG. 6D demonstrates that different binding affinities between BZIP and AZIP lead to different NFAT transcription activities. Binding affinities between two leucine zipper pairs were obtained from previously reported data.

FIGS. 8A-8C depict zinc-finger CAR design, logic computation and orthogonal control of T cell signaling. FIG. 8A depicts a schematic of zinc-finger CAR design. FIG. 8B demonstrates logic computation, such as AND and NOT gates can be created using zfCAR. FIG. 8C demonstrates that zfCAR can easily be made to bind to orthogonal double stranded (ds) DNA, thus allow independent control over various T cell signaling pathways.

FIG. 13A depicts a schematic of the experimental setup. In FIG. 13B ZipCARs were introduced into CD4+ T cells. The addition of an activating zipFv (anti-Her2-AZIP) leads to the production of IFN-γ when exposed to K562 cells expressing Her2. FIG. 13C demonstrates that zipCAR+CD8 T cells lead to the lysis of target K562 Her2+ cells in a dose-dependent manner. zipFv alone without the engineered T cells did not lead to cell killing.

FIG. 14A depicts a schematic diagram of the parameters and components that are systematically modulated for the characterization of the SUPRA platform. FIG. 14B demonstrates that varying the zipper affinity on the anti-Her2-AZIP zipFvs can modulate the tumor cell killing by primary CD8 T cells expressing the corresponding zipCAR. FIG. 14C demonstrates that varying the anti-Her2 scFv affinity on the anti-Her2-AZIP zipFvs can also modulate the cell killing efficiency of zipCAR expressing CD8 T cells.

FIG. 15A depicts tumor luciferase expression in mice treated with T cells modified with a traditional CAR or SUPRA CAR 42 days post tumor implantation. Her2+ tumor cells that constitutively express luciferase were implanted intraperitoneally into 15 mice. After 12 days, CAR T cells were injected into the mice and anti-HER2 zipFv was added 1 day later. Tumor imaging through IVIS was performed periodically. FIG. 15B depicts a graph of the size of Her2+ tumors in mice treated with SUPRA T cells or controls from day 12 to day 40.

FIG. 19C depicts a heatmap of 37 zippers (both AZIP and BZIP) used to generate zipCARs with CD3ζ, CD28, and 4-1BB as intracellular signaling domains. Each of the zipCARs was transduced via lentiviral transduction into Jurkat T cells that contain an NFAT transcription reporter (pNFAT-GFP). When the zipCAR is activated, the pNFAT-GFP reporter is activated and produces GFP expression. GFP expression was quantified using flow cytometry. Each zipper was assayed by co-culturing with Jurkat target cell lines expressing "dead" versions of another zipper, which were not fused to any signaling domains. Every zipCAR was tested against target cell lines for all other zippers to identify orthogonal zipper pairs that can be used in the SUPRA CAR platform. FIG. 19B demonstrates that three orthogonal pairs of zippers were identified based on NFAT transcription activity in Jurkat T cells. FIG. 19C demonstrates that a PD-1 intracellular signaling domain was fused to an anti-Mesothelin scFv (NOT a zipCAR) and, showing that PD-1 can inhibit anti-HER2 CAR activity in Jurkat T cells.

DETAILED DESCRIPTION

Figure 1A:
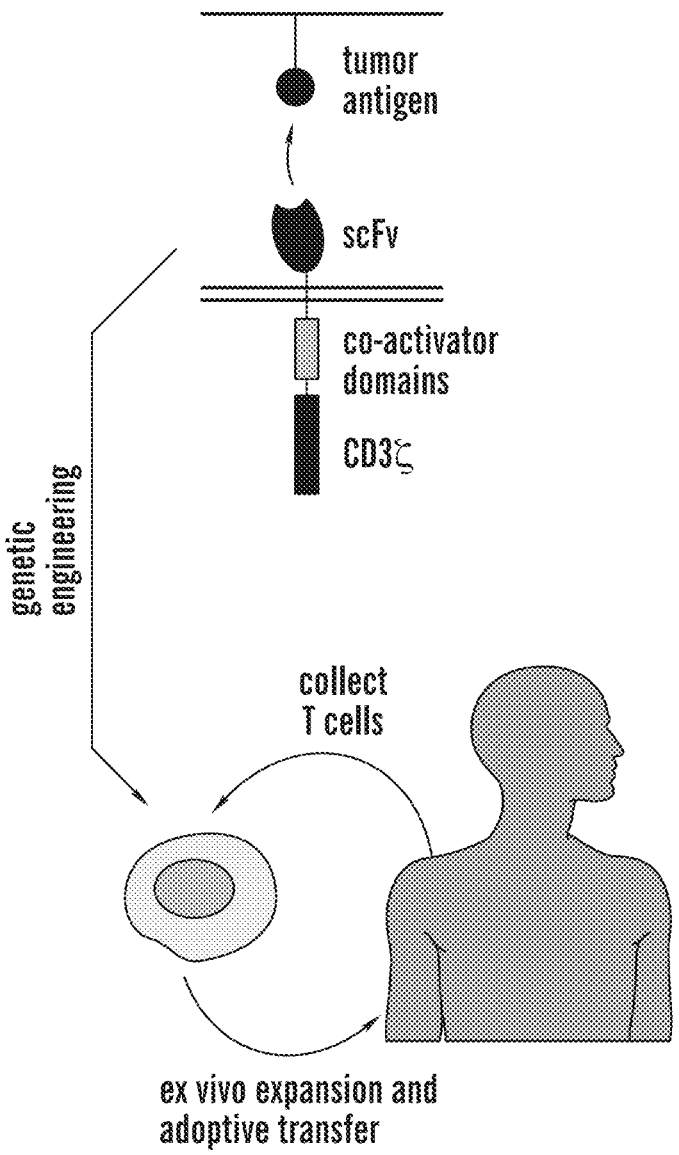
FIGS. 1A-1B depict schematics for various CAR design.

Described herein are chimeric antigen receptors (CARs) in which the recognition and signaling portions of the CAR are separate polypeptides. The two separate polypeptides that make up a complete CAR are able to interact and form the complete CAR by way of protein interaction domains. This permits flexible, modular CAR-T therapy which is capable of complex logic computation, providing a more precise and effective approach to immunotherapy.

In one aspect of any of the embodiments is a multi-component chimeric antigen receptor (CAR) and/or a composition comprising a multi-component CAR. Multi-component CARs are also referred to herein variously as SMART CAR or SUPRA.

As used herein, "chimeric antigen receptor" or "CAR" refers to an artificially constructed hybrid polypeptide comprising an antigen-binding domain (e.g. an antigen-binding portion of an antibody (e.g. a scFV)) linked to a cell signaling and/or cell activation domain. In some embodiments the cell-signaling domain can be a T-cell signaling domain. In some embodiments, the cell activation domain can be a T-cell activation domain. CARs have the ability to redirect the specificity and reactivity of T cells and other immune cells toward a selected target in a non-MHC-restricted manner, exploiting the antigen-binding properties of monoclonal antibodies. The non-MHIC-restricted antigen recognition gives T-cells expressing CARs the ability to recognize an antigen independent of antigen processing, thus bypassing a major mechanism of tumor escape. Moreover, when expressed in T-cells, CARs advantageously do not dimerize with endogenous T-cell receptor (TCR) alpha and beta chains. Most commonly, the CAR's extracellular binding domain is composed of a single chain variable fragment (scFv) derived from fusing the variable heavy and light regions of a murine or humanized monoclonal antibody. Alternatively, scFvs may be used that are derved from Fabs (instead of from an antibody, e.g., obtained from Fab libraries), in various embodiments, this scFv is fused to a transmembrane domain and then to an intracellular signaling domain. "First-generation" CARs include those that solely provide CD3zeta signals upon antigen binding, "Second-generation" CARs include those that provide both costimulation (e.g. CD28 or CD 137) and activation (CD3Q. "Third-generation" CARs include those that provide multiple costimulation (e.g. CD28 and CD 137) and activation (CO3Q). In various embodiments, the CAR is selected to have high affinity or avidity for the antigen. Further discussion of CARs can be found, e.g., in Maus et al. Blood 2014 123:2624-35; Reardon et al. Neuro-Oncology 2014 16:1441-1458; Hoyos et al. Haematologica 2012 97:1622; Byrd et al. J Clin Oncol 2014 32:3039-47; Maher et al. Cancer Res 2009 69:4559-4562; and Tamada et al. Clin Cancer Res 2012 18:6436-6445; each of which is incorporated by reference herein in its entirety.

As used herein, "multi-component CAR" refers to a CAR comprising at least two separate polypeptides, neither of which polypeptides is capable of both ligand recognition and signaling activation on its own. In some embodiments, the at least two separate polypeptides each comprise a protein interaction domain that permits interaction, e.g., binding of the separate polypeptides. In some embodiments, one of the at least two separate polypeptides is a transmembrane polypeptide having an intracellular T cell receptor (TCR) signaling domain and a second of the at least two separate polypeptides is an extracellular polypeptide having a ligand-binding domain. In some embodiments, a multi-component CAR can comprise two, three, four, five, or more separate polypeptides.

In one aspect of the embodiments, described herein is a multi-component chimeric antigen receptor (CAR); the multi-component CAR comprising: a) a first recognition polypeptide comprising 1) an antibody reagent specific for a first target ligand and 2) a protein interaction domain; and b) a signaling polypeptide comprising 1) an extracellular protein interaction domain that can bind specifically with the protein interaction domain of the first recognition polypeptide and 2) an intracellular T cell receptor (TCR) signaling domain.

As used herein, "recognition polypeptide" refers to an extracellular polypeptide having a ligand-binding domain. In some embodiments, the ligand-binding domain can be an antibody reagent. In some embodiments, the recognition polypeptide can further comprise a protein interaction domain.

As used herein, "signaling polypeptide" refers to a transmembrane polypeptide having an intracellular T cell receptor (TCR) signaling domain. In some embodiments, the signaling polypeptide can further comprise a protein interaction domain. In some embodiments, the signaling polypeptide can further comprise an extracellular protein interaction domain.

As used herein, "protein interaction domain" refers to a domain that permits specific binding of two separate polypeptides to each other. A number of exemplary protein interaction domains, as well as pairs of protein interaction domains are provided elsewhere herein. In some embodiments, the protein interaction domains of the polypeptides of a multi-component CAR can bind specifically, e.g. one of the protein interaction domains can bind specifically to a second protein interaction domain of the multi-component CAR. In some embodiments, specific binding can occur when two separate protein interaction domains are present. In some embodiments, specific binding can occur when three or more separate protein interaction domains are present. Exemplary protein interaction domains are known in the art and can be used in embodiments of the aspects described herein.

In some embodiments of any of the aspects described herein, the protein interaction domains can be leucine zipper domains. Leucine zipper domains are a type of protein-protein interaction domain commonly found in transcription factors characterized by leucine residues evenly spaced through a α-helix. Leucine zippers may form heterodimers or homodimers. A number of leucine zipper domains, as well as their ability to bind each other, are known in the art and discussed further, e.g., in Reinke et al. JACS 2010 132: 6025-31 and Thomposon et al. ACS Synth Biol 2012 1:118-129; each of which is incorporated by reference herein in its entirety. In some embodiments, one leucine zipper domain is BZip (RR) and the second leucine zipper domain is AZip (EE). In some embodiments, the sequence of a BZip (RR) leucine zipper domain is MDPDLEIRAAFLRQRNTA-LRTEVAELEQEVQRLENEVSQYETRYGPLGGGK (SEQ ID NO: 2). In some embodiments, the sequence of a AZip (EE) leucine zipper domain is MDPDLEIEAAFLER-ENTALETRVAELRQRVQRLRNRVSQYRTRYG-PLGGGK (SEQ ID NO: 3). Further exemplary leucine zipper domains are describe in Reinke et al. JACS 2010 132:6025-31; which is incorporated by reference herein in its entirety. For example, suitable leucine zipper domains can include SYNZIP 1 to SYNZIP 48, andBATF, FOS, ATF4, ATF3, BACH1, JUND, NFE2L3, and HEPTAD. Binding affinities of various combinations of these domains are described, e.g., at FIG. 1 of Reinke et al. In some embodiments, a suitable pair of leucine zipper domains has a dissociation constant (Kd) of 1000 nM or less. In some embodiments, a suitable pair of leucine zipper domains has a dissociation constant (Kd) of 100 nM or less. In some embodiments, a suitable pair of leucine zipper domains has a dissociation constant (Kd) of 10 nM or less. In some embodiments, a suitable pair of leucine zipper domains has a dissociation constant (Kd) of 1 nM or less.

Further exemplary pairs of protein interaction domains can include a) PSD95-Dlg1-zo-1 (PDZ) domains; b) a streptavidin domain and a streptavidin binding protein (SBP) domain; and c) a PYL domain and an ABI domain.

In some embodiments of any of the aspects described herein, the protein interaction domains can be chemically-induced protein interaction domains, e.g., domains that will only bind specifically in the presence of a third molecule, e.g., a small molecule or drug. Exemplary pairs of chemically-induced protein interaction domains can include: FKBP-binding domain of mTOR (FRB) and FK506 binding protein (FKBP) (binding of which is activated by tacrolimus, everolimus, or a rapalog); cyclophilin-Fas fusion protein (CyP-Fas) and FK506 binding protein (FKBP) (binding of which is activated by FKCsA); calcineurinA (CNA) and FK506 binding protein (FKBP) (binding of which is activated by FK506); gibberellin insensitive (GIA) and gibberellin insensitive dwarf1 (GID1) (binding of which is activated by gibberellin); Snap-tag and Halo tag (binding of which is activated by HaXS); and T14-3-3-cdeltaC and C-Terminal peptides of PMA2 (CT52) (binding of which is activated by fusicoccin). Further description of chemically-induced protein interaction domains can be found in the art, e.g., Miyamoto et al. Nat Chem Biol. 2012 Mar. 25; 8(5): 465-470 and Belshaw et al. PNAS 1996 93:4604-4607; each of which is incorporated herein by reference in its entirety.

In some embodiments of any of the aspects described herein, the protein interaction domains can comprise at least one nucleotide tag and at least one zinc finger domain. Zinc finger domains are characterized by the coordination of a zinc ion in order to stabilize their tertirary structure. The particular folds that appear in zinc fingers can vary. In some embodiments, a zinc finger domain can be a nucleotide-binding zinc finger domain. In some embodiments, a zinc finger domain can be a DNA-binding zinc finger domain. In some embodiments, the protein interaction domain of the recognition polypeptide is a nucleotide tag and the extra-cellular protein interaction domain of the signaling polypep-tide is a zinc finger domain. In some embodiments, a nucleotide tag can be a DNA tag. In some embodiments, a nucleotide tag can be a dsDNA tag comprising the entire recognition sequence for the zinc finger domain being used. Exemplary zinc finger domains and their cognate nucleotide tags are described in the art, e.g. Mali et al. Nature Methods 2013 10:403-406; which is incorporated by reference herein in its entirety. In some embodiments, a zinc finger domain can be sZF15 as described in Mali et al. Nature Methods 2013 10:403-406.

In aspects with a single recognition polypeptide and a single signaling polypeptide that are able to bind specifically without a third polypeptide, the multiple-component CARs described herein will activate in the presence of the target ligand, thereby inducing T cell activity in the vicinity of the target ligand. Further described herein are multiple-compo-nent CARs capable of logic computation, for example, multiple-component CARs that serve as AND, OR, or NOT logic gates.

Figure 8A:
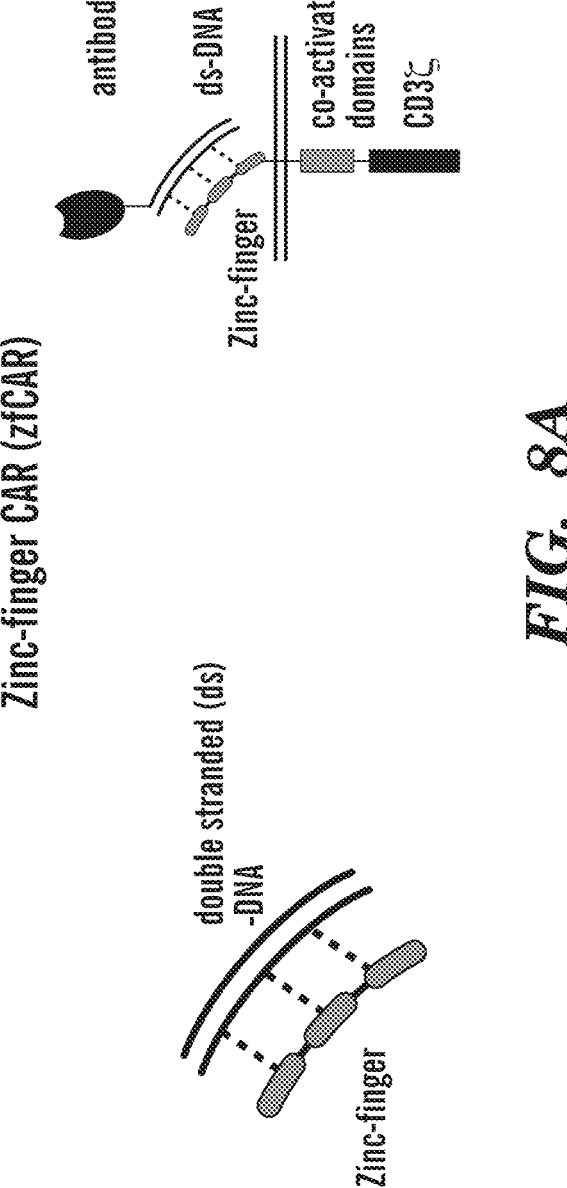
Figure 8B:
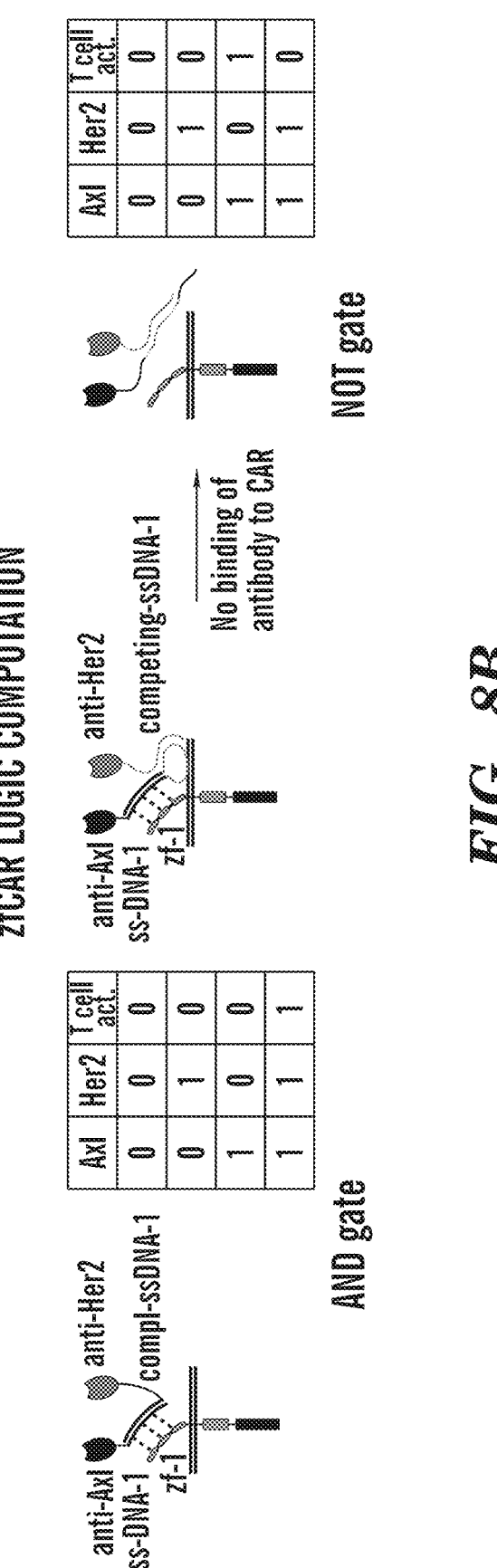
Figure 8C:
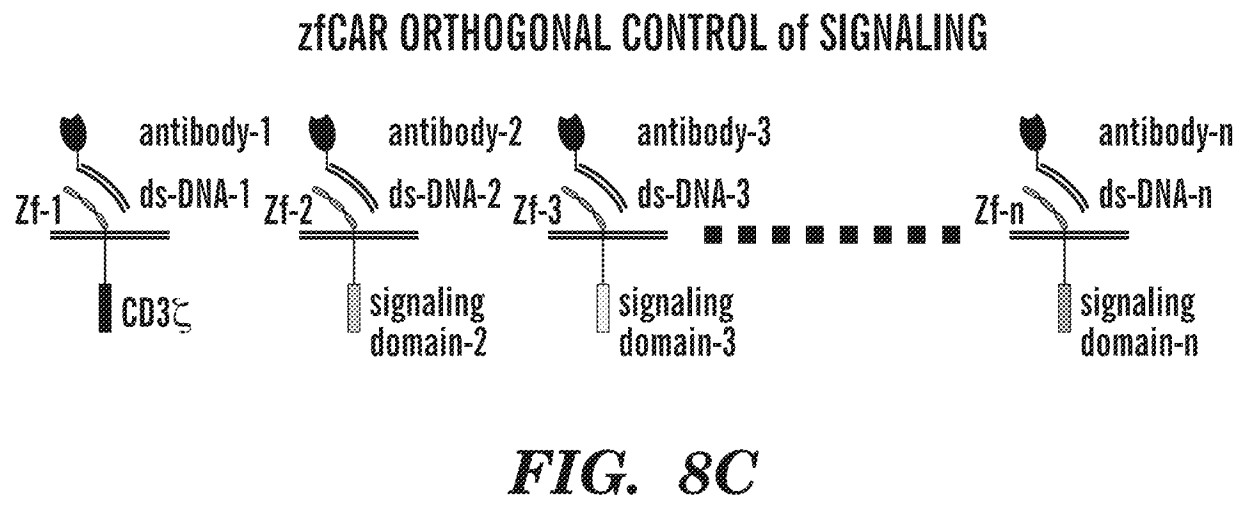
Figure 9:
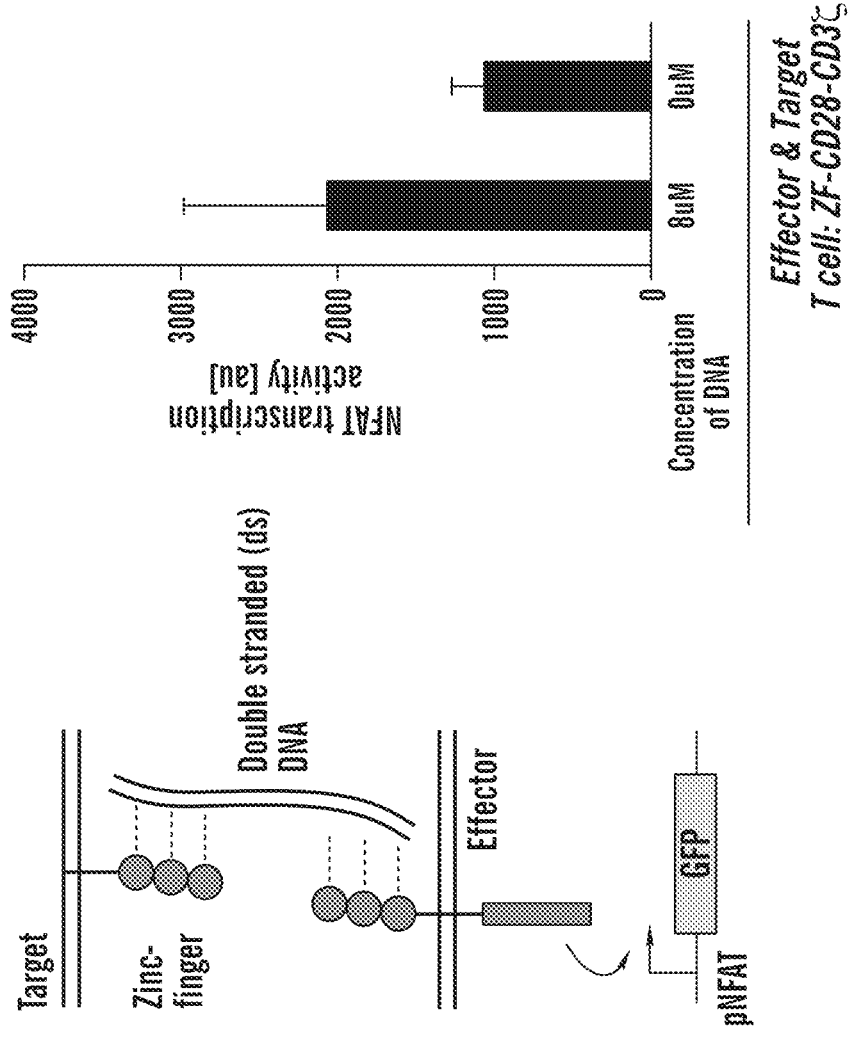
FIG. 9 depicts Zinc-finger CAR activation. A zinc-finger domain (zf15 11) serves as the extracellular domain of the CAR. This CAR can be activated by mixing double stranded zf15 specific DNA sequence (CCCaTGGGTGGCAt-AAAaTGGGTGGCAtAAAaTGGGTGGCAt-AAAaTGGGTGGCAtA AAaTGGGTGGCAt-AAAaTGGGTGGCAtAAA) (SEQ ID NO: 1) to and another cell that also expresses zf15 on the surface. NFAT transcription activity is used as a reporter of activation in Jurkat T cells.

In some aspects, described herein is a multiple-compo-nent CAR that permits AND gate logic. In these aspects, activation of the mulit-component CAR happens only in the presence of two target ligands; recognition of a single target ligand is not sufficient for activation. Such multi-component CARs can permit greater specificity and reduce off-target effects. Any single ligand that is a good marker for a target cell or tissue may occur elsewhere in a subject, resulting in off-target effects. However, requiring the recognition of two separate marker ligands reduces the odds of off-target activ-ity. In one aspect of any of the embodiments, described herein is a multi-component chimeric antigen receptor (CAR); the multi-component CAR comprising: a) a first recognition polypeptide comprising 1) an antibody reagent specific for a first target ligand and 2) a first portion of a nucleotide tag; b) a second recognition polypeptide com-prising 1) an antibody reagent specific for a second target ligand and 2) a second portion of the nucleotide tag; and c) a signaling polypeptide comprising 1) an extracellular zinc finger domain that can bind specifically with a complete nucleotide tag formed by the association of the individual portions of the nucleotide tag and 2) an intracellular T cell receptor (TCR) signaling domain; wherein the individual portions of the nucleotide tag cannot be specifically bound by the zinc finger domain unless they are associated with each other. In some embodiments, the first portion of the nucleotide tag is a ssDNA and the second portion of the nucleotide tag is a complementary ssDNA, such that when the two tags hybridize, they form a dsDNA that can be specifically bound by the zinc finger domain. In some embodiments, the first portion of the nucleotide tag is a dsDNA with a first overhang and the second portion of the nucleotide tag is a dsDNA with a complementary overhang, such that neither dsDNA comprise the entire recognition sequence required for zinc finger binding and when the overhangs hybridize, a single dsDNA comprising the entire recognition sequence required for zinc finger binding is formed. FIGS. 8A-8C depict exemplary multi-component CARs comprising zinc finger domains.

In some embodiments, described herein is a multi-com-ponent chimeric antigen receptor (CAR); the multi-compo-nent CAR comprising: a) a first recognition polypeptide comprising 1) an antibody reagent specific for a first target ligand and 2) a first portion of a nucleotide tag; b) a second recognition polypeptide comprising 1) an antibody reagent specific for a second target ligand and 2) a second portion of the nucleotide tag; c) a third recognition polypeptide encod-ing 1) an antibody reagent specific for a third target ligand and 2) a third portion of the nucleotide tag; and d) a signaling polypeptide comprising 1) an extracellular zinc finger domain that can bind specifically with a complete nucleotide tag formed by the association of the individual portions of the nucleotide tag and 2) an intracellular T cell receptor (TCR) signaling domain; wherein the individual portions of the nucleotide tag cannot be specifically bound by the zinc finger domain unless they are associated with each other. For example, the individual portions or pairwise combinations individual portions of the nucleotide tag cannot be specifi-cally bound by the zinc finger domain, but when all three portions are associated with each other, the resulting com-plex can be specifically bound by the zinc finger domain. In some embodiments, 1) the first portion of the nucleotide tag is a ssDNA; and 2) the second and third portions of the nucleotide tag are ssDNAs, each of which is complementary to the first portion and 3) the second and third portions of the nucleotide tag have sequences that do not overlap with each other. Additional arrangements of three nucleotide tags to regulate zinc finger domain binding are contemplated herein, e.g., using DNA origami. Such arrangements are described in the art, see, e.g., Wei et al. Nature 2012 485:623-626; Ke et al. Science 2012 338:1177-1183; and Douglas et al. Nature 2009 459:414-418; each of which is incorporated by reference herein in its entirety.

Further embodiments of AND logic gate multi-compo-nent CARs are described herein. In one aspect, a multi-component CAR comprising a recognition polypeptide com-prising a protein interaction domain and a signaling polypeptide comprising a protein interaction domain can further comprise a second recognition polypeptide compris-ing 1) an antibody reagent specific for a second target ligand and 2) a protein interaction domain; wherein the signaling polypeptide further comprises a secondary protein interac-tion domain that specifically binds with the protein interac-tion domain of the second recognition polypeptide. In some embodiments, the affinity of the signaling polypeptide's secondary protein interaction domain and the protein inter-action domain of the second recognition polypeptide is weaker than the affinity of the signaling polypeptide's first protein interaction domain and the protein interaction domain of the first recognition polypeptide. As described elsewhere herein, the relative affinities of protein interaction domains can be readily determined by one of skill in the art and are known in the art for a number of specific protein interaction domains. In some embodiments, the first and second recognition polypeptides each comprise a secondary protein interaction domain; and the secondary protein inter-action domains specifically bind to each other.

In some embodiments of any of the aspects described herein, a multi-component CAR as described herein can comprise a NOT logic gate (see, e.g., FIG. 8B). For example, recognition of a second target ligand by a second recognition polypeptide can prevent interaction (e.g. specific binding) of the signaling polypeptide and first recognition polypeptide. Such embodiments can permit suppression of T cell activity in inappropriate and/or off-target tissues. For example, the second target ligand can be a marker of a tissue that is particularly sensitive to T cell activity, is a known area of off-target activity, and/or shares markers with the desired target tissue. In some embodiments, in a NOT gate multi-component CAR, the second target ligand is not a ligand found in the target tissue and/or cells, e.g., in or on cancer cells. In some embodiments, the second target ligand of a NOT logic gate multi-component CAR is found on a healthy and/or non-target cell and not on a diseased and/or target cell. In one aspect, described herein is a a) recognition polypeptide comprising 1) an antibody reagent specific for a first target ligand and 2) a first nucleotide tag; b) a second recognition polypeptide comprising 1) an antibody reagent specific for a second target ligand and 2) a second nucleotide tag; and c) a signaling polypeptide comprising 1) an extracellular zinc finger domain that can bind specifically with the first nucleotide tag and 2) an intracellular T cell receptor (TCR) signaling domain; wherein the nucleotide tags cannot be specifically bound by the zinc finger domain when they are associated with each other. Various 2- and 3-dimensional configurations of such pairs of nucleotide pairs are known in the art, e.g., see discussion of DNA origami elsewhere herein. In an exemplary embodiment, the first nucleotide tag forms a hairpin-loop structure and the second nucleotide tag is complementary to a portion of the first nucleotide tag that encompasses a portion of one leg of the hairpin-loop and a portion of the loop of the hairpin-loop. Thus, in the absence of the second nucleotide tag, the first nucleotide tag comprises a dsDNA portion that can be bound by a cognate zinc finger. In the presence of the second nucleotide tag, the tags hybridize, forcing the first nucleotide tag to unfold from the hairpin-loop structure and resulting in a dsDNA molecule that lacks the necessary recognition sequence fot he same cognate zinc finger. Such an arrangement is depicted graphically in, e.g., FIG. 8B.

Described herein are other embodiments of NOT logic gate multi-component CARs. In one aspect, a multi-component CAR as described herein, e.g., one comprising a first recognition polypeptide with a protein interaction domain, can further comprise a second recognition polypeptide comprising 1) an antibody reagent specific for a second target ligand and 2) a protein interaction domain that competes with the protein interaction domain of the signaling polypeptide for binding to the protein interaction domain of the first recognition polypeptide. In one aspect, described herein is a NOT logic gate multi-component chimeric antigen receptor (CAR); the multi-component CAR comprising: a) a first recognition polypeptide comprising 1) an antibody reagent specific for a first target ligand and 2) a protein interaction domain; b) a signaling polypeptide comprising 1) an extracellular protein interaction domain that can bind specifically with the protein interaction domain of the first recognition polypeptide and 2) an intracellular T cell receptor (TCR) signaling domain; and c) a second recognition polypeptide comprising 1) an antibody reagent specific for a second target ligand and 2) a protein interaction domain that competes with the protein interaction domain of the signaling polypeptide for binding to the protein interaction domain of the first recognition polypeptide. In some embodiments, the target ligand recognized by the second recognition polypeptide is found on a healthy and/or non-target cell and not on a diseased and/or target cell. In some embodiments, the protein interaction domain of the second recognition polypeptide and the protein interaction domain of the first recognition polypeptide have a greater affinity than the protein interaction domain of the signaling polypeptide and the protein interaction domain of the first recognition polypeptide. Relative binding affinities can be determined experimentally, e.g., by binding affinity assays known in the art and relative binding affinities are known for a number of combinations of protein interaction domains described herein, see, e.g. Reinke et al. JACS 2010 132:6025-31; which is incorporated by reference herein in its entirety. In some embodiments, the binding affinity of the recognition polypeptide protein interaction domains can be at least 2× greater than the binding affinity of the first recognition polypeptide protein interaction domain and the signaling polypeptide interaction domain. In some embodiments, the binding affinity of the recognition polypeptide protein interaction domains can be at least 5× greater than the binding affinity of the first recognition polypeptide protein interaction domain and the signaling polypeptide interaction domain. In some embodiments, the binding affinity of the recognition polypeptide protein interaction domains can be at least 10× greater than the binding affinity of the first recognition polypeptide protein interaction domain and the signaling polypeptide interaction domain.

As used herein, "target ligand" refers to a molecule in or on a cell which can be bound by a ligand-binding domain. Non-limiting examples of such molecules can include polypeptides, lipids, saccharides, and the like. In some embodiments, the target ligand can be an extracellular molecule. In some embodiments, the target ligand can be a cell surface molecule.

In some embodiments, e.g., those relating to a multi-component CAR with a single recognition polypeptide or an AND gate multi-component CAR, the target ligand (e.g. the first and/or second target ligand) can be a ligand expressed in a target tissue. In some embodiments, the target ligand can be expressed constitutively in the target tissue and/or cell. In some embodiments, the target ligand can be expressed exclusively in the target tissue and/or cell. In some embodiments, the target ligand can be expressed at a higher level in the target tissue and/or cell than in other tissues and/or cells. As recognition of a target ligand in embodiments relating to a multi-component CAR with a single recognition polypeptide or an AND gate multi-component CAR can result in T cell activation (e.g. cell killing activity of the cell comprising the target ligand), the target ligand can be selected to target T cell activity in a desirable and/or therapeutic way, e.g., by targeting cancer cells. In some embodiments, a target ligand is a ligand found in/on a diseased and/or target cell. In some embodiments, the target ligand specifically bound by a recognition polypeptide that can specifically bind with a signaling polypeptide or is a portion of an AND gate multi-component CAR is a ligand found in/on a diseased and/or target cell. In some embodiments, a target ligand specifically bound by a recognition polypeptide that can specifically bind with a signaling polypeptide or is a portion of an AND gate multi-component CAR is a ligand found on a diseased and/or target cell and not on a healthy and/or non-target cell. In some embodiments, the diseased cell is a cancerous cell. In some embodiments, the target ligand specifically bound by a recognition polypeptide that can specifically bind with a signaling polypeptide or is a portion of an AND gate multi-component CAR is found on the surface of a cancer cell. In some embodiments, a recognition polypeptide that can specifically bind with a signaling polypeptide or is a portion of an AND gate multi-component CAR specifically binds to a target ligand on the surface of a cancer cell, e.g. as compared to binding to normal cells.

In some embodiments, a composition and/or cell described herein can further comprise a second multi-component CAR according to any of the aspects and embodiment described herein for the first multi-component CAR.

By way of non-limiting example, a second CAR can be designed to bind specifically to (and, e.g., be activated by or inhibited by) different target ligands than those to which the first multi-component CAR specifically binds (and, e.g. is activated by or inhibited by) This can provide increased specificity, reduced off-target effects, and/or reduced effective dosages for the methods described herein. In some embodiments, the antibody reagents of second multi-component CAR bind specifically to different target ligands than those bound by the antibody reagents of the first multi-component CAR.

In some embodiments, the second multi-component CAR can comprise an inhibitory intracellular T cell receptor (TCR) signaling domain, e.g., one that inhibits T cell activity. In such embodiments, the second multi-component can therefore be designed to operate in opposition to the first multi-component CAR, e.g. permitting inhibition of T cell activation while the first multi-component CAR permits activation of T cell activity. Inhibitory intracellular TCR signaling domains are known in the art and can include, by way of non-limiting example, PD1; CTLA4; BTLA; KIR; LAG-3; TIM-3; A2aR; LAIR-1; and TGIT. In some embodiments, the target ligand specifically bound by a recognition polypeptide that can specifically bind with the signaling polypeptide of the second multi-component CAR comprising an inhibitory intracellular TCR signaling domain is a ligand found on a healthy and/or non-target cell. In some embodiments, the target ligand specifically bound by a recognition polypeptide that can specifically bind with the signaling polypeptide of the second multi-component CAR comprising an inhibitory intracellular TCR signaling domain is a ligand found on a healthy and/or non-target cell and not on a diseased and/or target cell. In some embodiments, the second multi-component CAR comprising an inhibitory intracellular TCR signaling domain can be an OR logic gate according to any of the embodiments described herein and the second target ligand can be a ligand found in/on, or specific to, diseased (e.g. cancerous) cells.

In some embodiments of any of the aspects, a ligand-binding domain can comprise or consist essentially of an antibody reagent. In some embodiments, the antibody reagent can be an immunoglobulin molecule, a monoclonal antibody, a chimeric antibody, a CDR-grafted antibody, a human antibody, a humanized antibody, a Fab, a Fab', a F(ab')2, a Fv, a disulfide linked Fv, a scFv, a single domain antibody, a diabody, a multispecific antibody, a dual specific antibody, an anti-idiotypic antibody, and/or a bispecific antibody.

In some embodiments, the intracellular TCR signaling domain can be a T-cell activation domain. In some embodiments, the intracellular TCR signaling domain is a signaling domain from a protein selected from the group consisting of: TCRζ, FcRγ, FcRβ, CD3γ, CD3δ, CD3δ, CD3ζ, CD22, CD79a, CD79b, CD66d, CARD11, CD2, CD7, CD27, CD28, CD30, CD40, CD54 (ICAM), CD83, CD134 (OX40), CD137 (4-1iB), CD150 (SLAMF1), CD152 (CTLA4), CD223 (LAG3), CD270 (HVEM), CD273 (PD-L2), CD274 (PD-L1), CD278 (ICOS), DAP10, LAT, NKD2C SLP76, TRIM, ZAP70, and 41BB.

The multi-component CARs described herein can permit regulation of cellular activity, e.g., T, NK, or NKT cell activity, e.g., cell-killing activity mediated and/or performed by such cells. Accordingly, in some embodiments, one or more multi-component CARs as described herein can be present in/on a cell. In some embodiments, a signaling polypeptide is present on the membrane of a cell. In some embodiments, the one or more recognition polypeptides are present in the extracellular space, e.g., the recognition polypeptide(s) can be expressed and secreted by the cell or the cell can be contacted by recognition polypeptides provided from another source (e.g. produced synthetically or by another cell and optionally, purified or processed before the contacting step).

In one aspect, described herein is an engineered cell expressing and/or comprising one or more multi-component CARs as described herein, e.g., at least one signaling polypeptide and at least one recognition polypeptide. In some embodiments, the cell is a T cell, NK cell, or NKT cell. In some embodiments, the cell is a T cell. Such cells expressing and/or comprising both a signaling polypeptide and at least one recognition polypeptide of a multi-component CAR are referred to herein as "complete multi-component CAR" cells. In some embodiments, a complete multi-component CAR cell expresses both a signaling polypeptide and at least one recognition polypeptide of a multi-component CAR. In some embodiments, a complete multi-component CAR cell comprises nucleic acid sequences encoding both a signaling polypeptide and at least one recognition polypeptide of a multi-component CAR.

In any of the aspects described herein, e.g., those relating to either a complete or partial multi-component CAR cell, the recognition and/or signaling polypeptide can be under the control of an inducible and/or repressible promoter. Such promoters allow the expression of the polypeptide to be increased or decreased as desired and are in contrast to constitutive promoters. The term "constitutively active promoter" refers to a promoter of a gene which is expressed at all times within a given cell. Exemplary promoters for use in mammalian cells include cytomegalovirus (CMV) and the like. The term "inducible promoter" refers to a promoter of a gene which can be expressed in response to a given signal, for example addition or reduction of an agent. Non-limiting examples of an inducible promoter are promoters that are regulated in a specific tissue type, a promoter regulated by a steroid hormone, by a polypeptide hormone (e.g., by means of a signal transduction pathway), or by a heterologous polypeptide (e.g., the tetracycline-inducible systems, "Tet-On" and "Tet-Off"; see, e.g., Clontech Inc., CA, Gossen and Bujard, Proc. Natl. Acad. Sci. USA 89:5547, 1992, and Paillard, Human Gene Therapy 9:983, 1989; each of which are incorporated by reference herein in its entirety). In some embodiments, expression of the polypeptide can be precisely regulated, for example, by using an inducible regulatory sequence that is sensitive to certain physiological regulators, e.g., circulating glucose levels, or hormones (Docherty et al., 1994, FASEB J. 8:20-24). Such inducible expression systems, suitable for the control of expression in cells or in mammals include, for example, regulation by ecdysone, by estrogen, progesterone, tetracycline, chemical inducers of dimerization, and isopropyl-beta-D1-thiogalactopyranoside (IPTG). A person skilled in the art would be able to choose the appropriate regulatory/promoter sequence based on the intended use of the polypeptide.

In some embodiments, the expression of one or more of the recognition or signaling polypeptides can be constitutive. In some embodiments, the expression of one or more of the recognition or signaling polypeptides can be transient. Transient expression can be achieved by, e.g., use of transient and/or inducible expression promoters or by use of transient vectors, e.g. those that do not incorporate into the genome and/or persist in the target cell. By way of non-limiting example, derivatives of viruses such as the bovine papillomavirus (BPV-1), or Epstein-Barr virus (pHEBo, pREP-derived and p205) can be used for transient expression of nucleic acids in eukaryotic cells. For other suitable expression systems as well as general recombinant procedures, see Molecular Cloning A Laboratory Manual, 2nd Ed., ed. by Sambrook, Fritsch and Maniatis (Cold Spring Harbor Laboratory Press: 1989) Chapters 16 and 17; which is incorporated by reference herein in its entirety. In some embodiments, the signaling polypeptide of a multi-component CAR can be constitutively expressed and the recognition polypeptide can be transiently expressed. In some embodiments, the recognition polypeptide of a multi-component CAR can be constitutively expressed and the signaling polypeptide can be transiently expressed.

In one aspect, described herein is a method of killing a target cell, the method comprising contacting the cell with a complete multi-component CAR cell according to any of the embodiments described herein. In some embodiments, the target cell can be a diseased cell, e.g., a cancer cell. In one aspect, described herein is a method of treating a disease, comprising administering a complete multi-component CAR cell according to any of the embodiments described herein. In some embodiments, the disease can be cancer; solid cancers; breast cancer; lung cancer; acute lymphoblastic leukemia; multiple myeloma; or refractory multiple myeloma. In one aspect, described herein is a method of treating cancer, comprising administering a complete multi-component CAR cell according to any of the embodiments described herein. In some embodiments, the complete multi-component CAR cell can be autologous to the subject. In some embodiments, the complete multi-component CAR cell can be derived and/or descended from a cell obtained from the subject and has been modified ex vivo to comprise the at least one multi-component CAR, e.g., genetically engineered to comprise nucleic acid sequences encoding both a signaling polypeptide and at least one recognition polypeptide of a multi-component CAR. In some embodiments, the method can further comprise the steps of obtaining a cell from a subject (e.g. a T, NK, or NKT cell or a progenitor thereof), altering the cell to comprise nucleic acid sequences encoding both a signaling polypeptide and at least one recognition polypeptide of a multi-component CAR, and then administering the cell to the subject.

In one aspect, described herein is an engineered cell expressing and/or comprising one or more multi-component CAR signaling polypeptides according to any of the embodiments described herein. In some embodiments, the cell is a T cell, NK cell, or NKT cell. In some embodiments, the cell is a T cell. Such cells expressing and/or comprising a multi-component CAR signaling polypeptide are referred to herein as "partial multi-component CAR" cells. In some embodiments, the partial multi-component CAR cell does not express, e.g., does not comprise a nucleic acid sequence encoding, a multi-component CAR recognition polypeptide. In some embodiments, a partial multi-component CAR cell comprises a nucleic acid sequence encoding at least one multi-component CAR signaling polypeptide. In some embodiments, the multi-component CAR signaling polypeptide is present on the membrane of the cell, e.g., is expressed as a transmembrane protein at detectable levels. In some embodiments, the signaling polypeptide further comprises a secondary protein interaction domain that specifically binds with the protein interaction domain of the second recognition polypeptide, e.g., the signaling polypeptide is part of an AND gate multi-component CAR as described elsewhere herein. In some embodiments, the cell can further comprise a second multi-component CAR signaling polypeptide, e.g., a signaling polypeptide that is part of a second multi-component CAR according to any of the embodiments described herein.

In one aspect, described herein is a method of killing a target cell, the method comprising contacting the target cell with a partial multi-component CAR cell according to any of the embodiments described herein and contacting the target cell with at least one recognition polypeptide of the multi-component CAR. In some embodiments, the target cell can be a diseased cell, e.g., a cancer cell. In one aspect, described herein is a method of treating a disease, the method comprising administering to a subject in need of treatment thereof: a partial multi-component CAR cell and a first recognition polypeptide comprising 1) an antibody reagent specific for a first target ligand and 2) a protein interaction domain that can bind specifically with the protein interaction domain of the signaling polypeptide of the partial multi-component CAR. In some embodiments, the partial multi-component CAR cell can be autologous to the subject. In some embodiments, the partial multi-component CAR cell can be derived and/or descended from a cell obtained from the subject and has been modified ex vivo to comprise the at least one partial multi-component CAR, e.g., genetically engineered to comprise a nucleic acid sequence encoding a signaling polypeptide of a multi-component CAR. In some embodiments, the method can further comprise the steps of obtaining a cell from a subject (e.g. a T, NK, or NKT cell or a progenitor thereof), altering the cell to comprise a nucleic acid sequence encoding a signaling polypeptide of a multi-component CAR, and then administering the cell to the subject.

In some embodiments, the partial multi-component CAR cell comprises a NOT gate multi-component CAR according to any of the embodiments described herein. In some embodiments, a subject administered a partial multi-component CAR cell and a first recognition polypeptide can be further administered a second recognition polypeptide comprising 1) an antibody reagent specific for a second target ligand and 2) a protein interaction domain that competes with the protein interaction domain of the signaling polypeptide for binding to the protein interaction domain of the first recognition polypeptide. In some embodiments, the target ligand recognized by the second recognition polypeptide is found on a healthy and/or non-target cell and not on a diseased and/or target cell. In some embodiments, the protein interaction domain of the second recognition polypeptide and the protein interaction domain of the first recognition polypeptide have a greater affinity than the protein interaction domain of the signaling polypeptide and the protein interaction domain of the first recognition polypeptide. In some embodiments, the first recognition polypeptide comprising 1) an antibody reagent specific for a first target ligand and 2) a first nucleotide tag; and the second recognition polypeptide comprising 1) an antibody reagent specific for a second target ligand and 2) a second nucleotide tag; wherein the signaling polypeptide comprises 1) an extracellular zinc finger domain that can bind specifically with the first nucleotide tag; and wherein the nucleotide tags cannot be specifically bound by the zinc finger domain when they are associated with each other. In some embodiments, the first nucleotide tag forms a hairpin-loop structure and wherein the second nucleotide tag is complementary to a portion of the first nucleotide tag that encompasses a portion of one leg of the hairpin-loop and a portion of the loop of the hairpin-loop. In some embodiments, the second target ligand is found on a healthy and/or non-target cell and not on a diseased and/or target cell.

In some embodiments, the partial multi-component CAR cell comprises an AND gate multi-component CAR according to any of the embodiments described herein. In some embodiments, a subject administered a partial multi-component CAR cell and a first recognition polypeptide can be further administered a second recognition polypeptide comprising 1) an antibody reagent specific for a second target ligand and 2) a protein interaction domain; wherein the signaling polypeptide further comprises a secondary protein interaction domain that specifically binds with the protein interaction domain of the second recognition polypeptide. In some embodiments, the first and second recognition polypeptides each comprise a secondary protein interaction domain; wherein the secondary protein interaction domains specifically bind to each other. In some embodiments, the affinity of the signaling polypeptide's secondary protein interaction domain and the protein interaction domain of the second recognition polypeptide is weaker than the affinity of the signaling polypeptide's first protein interaction domain and the protein interaction domain of the first recognition polypeptide. In some embodiments, the first recognition polypeptide comprises 1) an antibody reagent specific for a first target ligand and 2) a first portion of a nucleotide tag; and the second recognition polypeptide comprises 1) an antibody reagent specific for a second target ligand and 2) a second portion of the nucleotide tag; wherein the signaling polypeptide comprises 1) an extracellular zinc finger domain that can bind specifically with a complete nucleotide tag formed by the association of the individual portions of the nucleotide tag; and wherein the individual portions of the nucleotide tag cannot be specifically bound by the zinc finger domain unless they are associated with each other. In some embodiments, the first portion of the nucleotide tag is an ssDNA and the second portion of the nucleotide tag is a complementary ssDNA. In some embodiments, the method can comprise administering a third recognition polypeptide encoding 1) an antibody reagent specific for a third target ligand and 2) a third portion of the nucleotide tag; wherein the individual portions or pairwise combinations individual portions of the nucleotide tag cannot be specifically bound by the zinc finger domain, but when all three portions are associated with each other, the resulting complex can be specifically bound by the zinc finger domain. In some embodiments, 1) the first portion of the nucleotide tag is a ssDNA; and 2) the second and third portions of the nucleotide tag are ssDNAs, each of which is complementary to the first portion and 3) the second and third portions of the nucleotide tag have sequences that do not overlap with each other.

In some embodiments, the partial multi-component CAR cell can comprise a second signaling polypeptide that is part of a second multi-component CAR according to any of the embodiments described herein. In some embodiments, the subject is further administered a second recognition polypeptide comprising 1) an antibody reagent specific for a second target ligand and 2) a protein interaction domain that can bind specifically with the protein interaction domain of the second signaling polypeptide. In some embodiments, the intracellular T cell receptor (TCR) signaling domain of the second multi-component CAR signaling polypeptide inhibits T cell activity. In some embodiments, the target ligand specifically bound by a recognition polypeptide that can specifically bind with the second signaling polypeptide is a ligand found on a healthy and/or non-target cell. In some embodiments, the target ligand specifically bound by a recognition polypeptide that can specifically bind with the second signaling polypeptide is a ligand found on a healthy and/or non-target cell and not on a diseased and/or target cell.

In some embodiments of any of the methods described herein, a pair of protein interaction domains of a multi-component CAR can comprise chemically induced binding domains and the method can further comprise administering a compound that induces binding of the domains. In some embodiments, when one protein interaction domain is FKBP-binding domain of mTOR (FRB) and a second protein interaction domain is FK506 binding protein (FKBP), the method further comprises administering tacrolimus, a rapalog, or everolimus. In some embodiments, when one protein interaction domain is cyclophilin-Fas fusion protein (CyP-Fas) and a second protein interaction domain is FK506 binding protein (FKBP), the method further comprises administering FKCsA. In some embodiments, when one protein interaction domain is calcineurinA (CNA) and a second protein interaction domain is FK506 binding protein (FKBP), the method further comprises administering FK506. In some embodiments, when one protein interaction domain is gibberellin insensitive (GIA) and a second protein interaction domain is gibberellin insensitive dwarf1 (GID1), the method further comprises administering gibberellin. In some embodiments, when one protein interaction domain is Snap-tag and a second protein interaction domain is Halo tag, the method further comprises administering HaXS. In some embodiments, when one protein interaction domain is T14-3-3-cdeltaC and a second protein interaction domain is C-Terminal peptides of PMA2 (CT52), the method further comprises administering fusicoccin.

In some embodiments of any of the aspects described herein, a recognition and/or signaling polypeptide of a multi-component CAR can be engineered. In some embodiments of any of the aspects described herein, a recognition and/or signaling polypeptide of a multi-component CAR can be transgenic. In some embodiments of any of the aspects described herein, a recognition and/or signaling polypeptide of a multi-component CAR can be recombinant. In some embodiments of any of the aspects described herein, a recognition and/or signaling polypeptide of a multi-component CAR can be heterologous to a cell. In some embodiments of any of the aspects described herein, a recognition and/or signaling polypeptide of a multi-component CAR can be heterologous to a T cell. In some embodiments of any of the aspects described herein, a recognition and/or signaling polypeptide of a multi-component CAR can be heterologous to a human T cell. In some embodiments of any of the aspects described herein, a recognition and/or signaling polypeptide of a multi-component CAR can be exogenous to a cell. In some embodiments of any of the aspects described herein, a recognition and/or signaling polypeptide of a multi-component CAR can be exogenous to a T cell. In some embodiments of any of the aspects described herein, a recognition and/or signaling polypeptide of a multi-component CAR can be exogenous to a human T cell.

It is specifically contemplated herein that each of the individual embodiments described herein can be combined, e.g., in a single cell. By way of non-limiting example, a single cell could comprise a first complete multi-component CAR and a second partial multi-component CAR, wherein each multi-component CAR can be according to any of the embodiments described herein.

In some embodiments, the methods described herein relate to CAR-immune cell therapies such as CAR-T therapy. Standard CAR-T and related therapies relate to adoptive cell transfer of immune cells (e.g. T cells) expressing a CAR that binds specifically to a targeted cell type (e.g. cancer cells) to treat a subject. In some embodiments, the cells administered as part of the therapy can be autologous to the subject. In some embodiments, the cells administered as part of the therapy are not autologous to the subject. In some embodiments, the cells are engineered and/or genetically modified to express a multi-component CAR or portion thereof as described herein. Further discussion of CAR-T therapies can be found, e.g., in Maus et al. Blood 2014 123:2624-35; Reardon et al. Neuro-Oncology 2014 16:1441-1458; Hoyos et al Haematologica 2012 97:1622; Byrd et al. J Clin Oncol 2014 32:3039-47; Maher et al. Cancer Res 2009 69:4559-4562; and Tamada et al. Clin Cancer Res 2012 18:6436-6445; each of which is incorporated by reference herein in its entirety.

In some embodiments, the technology described herein relates to a syringe or catheter, including an organ-specific catheter (e.g., renal catheter, biliary catheter, cardiac catheter, etc.), comprising a therapeutically effective amount of a composition described herein.

In some embodiments, the methods described herein relate to treating a subject having or diagnosed as having cancer with one or more multi-component CARs as described herein. Subjects having cancer can be identified by a physician using current methods of diagnosing cancer. Symptoms and/or complications of cancer which characterize these conditions and aid in diagnosis are well known in the art and include but are not limited to, presence of tumor, organ function impairment or failure, abnormal blood counts, weight loss, etc. Tests that may aid in a diagnosis of, e.g. cancer include, but are not limited to, blood counts, X-rays, and CT scans. A family history of cancer, or exposure to risk factors for cancer (e.g. smoking or radiation exposure) can also aid in determining if a subject is likely to have cancer or in making a diagnosis of cancer.

As used herein, the term "cancer" relates generally to a class of diseases or conditions in which abnormal cells divide without control and can invade nearby tissues. Cancer cells can also spread to other parts of the body through the blood and lymph systems. There are several main types of cancer. Carcinoma is a cancer that begins in the skin or in tissues that line or cover internal organs. Sarcoma is a cancer that begins in bone, cartilage, fat, muscle, blood vessels, or other connective or supportive tissue. Leukemia is a cancer that starts in blood-forming tissue such as the bone marrow, and causes large numbers of abnormal blood cells to be produced and enter the blood. Lymphoma and multiple myeloma are cancers that begin in the cells of the immune system. Central nervous system cancers are cancers that begin in the tissues of the brain and spinal cord.

As used herein, the term "malignant" refers to a cancer in which a group of tumor cells display one or more of uncontrolled growth (i.e., division beyond normal limits), invasion (i.e., intrusion on and destruction of adjacent tissues), and metastasis (i.e., spread to other locations in the body via lymph or blood). As used herein, the term "metastasize" refers to the spread of cancer from one part of the body to another. A tumor formed by cells that have spread is called a "metastatic tumor" or a "metastasis." The metastatic tumor contains cells that are like those in the original (primary) tumor.

As used herein, the term "benign" or "non-malignant" refers to tumors that may grow larger but do not spread to other parts of the body. Benign tumors are self-limited and typically do not invade or metastasize.

A "cancer cell" or "tumor cell" refers to an individual cell of a cancerous growth or tissue. A tumor refers generally to a swelling or lesion formed by an abnormal growth of cells, which may be benign, pre-malignant, or malignant. Most cancer cells form tumors, but some, e.g., leukemia, do not necessarily form tumors. For those cancer cells that form tumors, the terms cancer (cell) and tumor (cell) are used interchangeably.

A subject that has a cancer or a tumor is a subject having objectively measurable cancer cells present in the subject's body. Included in this definition are malignant, actively proliferative cancers, as well as potentially dormant tumors or micrometastatses. Cancers which migrate from their original location and seed other vital organs can eventually lead to the death of the subject through the functional deterioration of the affected organs. Hemopoietic cancers, such as leukemia, are able to out-compete the normal hemopoietic compartments in a subject, thereby leading to hemopoietic failure (in the form of anemia, thrombocytopenia and neutropenia) ultimately causing death.

The compositions and methods described herein can be administered to a subject having or diagnosed as having cancer. In some embodiments, the methods described herein comprise administering an effective amount of compositions described herein to a subject in order to alleviate a symptom of a cancer. As used herein, "alleviating a symptom of a cancer" is ameliorating any condition or symptom associated with the cancer. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, topical, injection, or intratumoral administration. Administration can be local or systemic.

The administration of the compositions contemplated herein may be carried out in any convenient manner, including by aerosol inhalation, injection, ingestion, transfusion, implantation or transplantation. In a preferred embodiment, compositions are administered parenterally. The phrases "parenteral administration" and "administered parenterally" as used herein refers to modes of administration other than enteral and topical administration, usually by injection, and includes, without limitation, intravascular, intravenous, intramuscular, intraarterial, intrathecal, intracapsular, intraorbital, intratumoral, intracardiac, intradermal, intraperitoneal, transtracheal, subcutaneous, subcuticular, intraarticular, subcapsular, subarachnoid, intraspinal and intrasternal injection and infusion. In one embodiment, the compositions contemplated herein are administered to a subject by direct injection into a tumor, lymph node, or site of infection.

It can generally be stated that a pharmaceutical composition comprising the cells, e.g., T cells or multi-component CAR cells, described herein may be administered at a dosage of $10^2$ to $10^{10}$ cells/kg body weight, preferably $10^5$ to $10^6$ cells/kg body weight, including all integer values within those ranges. The number of cells will depend upon the ultimate use for which the composition is intended as will the type of cells included therein. For uses provided herein, the cells are generally in a volume of a liter or less, can be 500 mLs or less, even 250 mLs or 100 mLs or less. Hence the density of the desired cells is typically greater than $10^6$ cells/ml and generally is greater than $10^7$ cells/ml, generally $10^8$ cells/ml or greater. The clinically relevant number of immune cells can be apportioned into multiple infusions that cumulatively equal or exceed $10^5$, $10^6$, $10^7$, $10^8$, $10^9$, $10^{10}$, $10^{11}$, or $10^{12}$ cells. In some aspects of the present invention, particularly since all the infused cells will be redirected to a particular target antigen, lower numbers of cells, in the range of $10^6$/kilogram ($10^6$-$10^{11}$ per patient) may be administered. Multi-component CAR expressing cell compositions may be administered multiple times at dosages within these ranges. The cells may be allogeneic, syngeneic, xenogeneic, or autologous to the patient undergoing therapy. If desired, the treatment may also include administration of mitogens (e.g., PHA) or lymphokines, cytokines, and/or chemokines (e.g., IFN-$\gamma$, IL-2, IL-12, TNF-alpha, IL-18, and TNF-beta, GM-CSF, IL-4, IL-13, Flt3-L, RANTES, MIP1$\alpha$, etc.) as described herein to enhance induction of the immune response. In some embodiments, the dosage can be from about $1 \times 10^5$ cells to about $1 \times 10^8$ cells per kg of body weight. In some embodiments, the dosage can be from about $1 \times 10^6$ cells to about $1 \times 10^7$ cells per kg of body weight. In some embodiments, the dosage can be about $1 \times 10^6$ cells per kg of body weight. In some embodiments, one dose of cells can be administered. In some embodiments, the dose of cells can be repeated, e.g., once, twice, or more. In some embodiments, the dose of cells can be administered on, e.g., a daily, weekly, or monthly basis.

The dosage ranges for the agent depend upon the potency, and encompass amounts large enough to produce the desired effect e.g., slowing of tumor growth or a reduction in tumor size. The dosage should not be so large as to cause unacceptable adverse side effects. Generally, the dosage will vary with the age, condition, and sex of the patient and can be determined by one of skill in the art. The dosage can also be adjusted by the individual physician in the event of any complication. In some embodiments, the dosage ranges from 0.001 mg/kg body weight to 0.5 mg/kg body weight. In some embodiments, the dose range is from 5 µg/kg body weight to 100 µg/kg body weight. Alternatively, the dose range can be titrated to maintain serum levels between 1 µg/mL and 1000 µg/mL. For systemic administration, subjects can be administered a therapeutic amount, such as, e.g., 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more Administration of the doses recited above can be repeated. In some embodiments, the doses are given once a day, or multiple times a day, for example but not limited to three times a day. In some embodiments, the doses recited above are administered daily for several weeks or months. The duration of treatment depends upon the subject's clinical progress and responsiveness to therapy.

In some embodiments, the dose can be from about 2 mg/kg to about 15 mg/kg. In some embodiments, the dose can be about 2 mg/kg. In some embodiments, the dose can be about 4 mg/kg. In some embodiments, the dose can be about 5 mg/kg. In some embodiments, the dose can be about 6 mg/kg. In some embodiments, the dose can be about 8 mg/kg. In some embodiments, the dose can be about 10 mg/kg. In some embodiments, the dose can be about 15 mg/kg. In some embodiments, the dose can be from about 100 mg/m² to about 700 mg/m². In some embodiments, the dose can be about 250 mg/m². In some embodiments, the dose can be about 375 mg/m². In some embodiments, the dose can be about 400 mg/m². In some embodiments, the dose can be about 500 mg/m².

In some embodiments, the dose can be administered intravenously. In some embodiments, the intravenous administration can be an infusion occurring over a period of from about 10 minute to about 3 hours. In some embodiments, the intravenous administration can be an infusion occurring over a period of from about 30 minutes to about 90 minutes.

In some embodiments the dose can be administered about weekly. In some embodiments, the dose can be administered weekly. In some embodiments, the dose can be administered weekly for from about 12 weeks to about 18 weeks. In some embodiments the dose can be administered about every 2 weeks. In some embodiments the dose can be administered about every 3 weeks. In some embodiments, the dose can be from about 2 mg/kg to about 15 mg/kg administered about every 2 weeks. In some embodiments, the dose can be from about 2 mg/kg to about 15 mg/kg administered about every 3 weeks. In some embodiments, the dose can be from about 2 mg/kg to about 15 mg/kg administered intravenously about every 2 weeks. In some embodiments, the dose can be from about 2 mg/kg to about 15 mg/kg administered intravenously about every 3 weeks. In some embodiments, the dose can be from about 200 mg/m² to about 400 mg/m² administered intravenously about every week. In some embodiments, the dose can be from about 200 mg/m² to about 400 mg/m² administered intravenously about every 2 weeks. In some embodiments, the dose can be from about 200 mg/m² to about 400 mg/m² administered intravenously about every 3 weeks. In some embodiments, a total of from about 2 to about 10 doses are administered. In some embodiments, a total of 4 doses are administered. In some embodiments, a total of 5 doses are administered. In some embodiments, a total of 6 doses are administered. In some embodiments, a total of 7 doses are administered. In some embodiments, a total of 8 doses are administered. In some embodiments, the administration occurs for a total of from about 4 weeks to about 12 weeks. In some embodiments, the administration occurs for a total of about 6 weeks. In some embodiments, the administration occurs for a total of about 8 weeks. In some embodiments, the administration occurs for a total of about 12 weeks. In some embodiments, the initial dose can be from about 1.5 to about 2.5 fold greater than subsequent doses.

In some embodiments, the dose can be from about 1 mg to about 2000 mg. In some embodiments, the dose can be about 3 mg. In some embodiments, the dose can be about 10 mg. In some embodiments, the dose can be about 30 mg. In some embodiments, the dose can be about 1000 mg. In some embodiments, the dose can be about 2000 mg. In some embodiments, the dose can be about 3 mg given by intravenous infusion daily. In some embodiments, the dose can be about 10 mg given by intravenous infusion daily. In some embodiments, the dose can be about 30 mg given by intravenous infusion three times per week.

A therapeutically effective amount is an amount of an agent that is sufficient to produce a statistically significant, measurable change in tumor size, tumor growth etc. (efficacy measurements are described below herein). Such effective amounts can be gauged in clinical trials as well as animal studies.

An agent can be administered intravenously by injection or by gradual infusion over time. Given an appropriate formulation for a given route, for example, agents useful in the methods and compositions described herein can be administered intravenously, intranasally, by inhalation, intraperitoneally, intramuscularly, subcutaneously, intracavity, and can be delivered by peristaltic means, if desired, or by other means known by those skilled in the art. It is preferred that the compounds used herein are administered orally, intravenously or intramuscularly to a patient having cancer. Local administration directly to a tumor mass is also specifically contemplated.

Therapeutic compositions containing at least one agent can be conventionally administered in a unit dose, for example. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired.

In embodiments where the subject is administered a partial multi-component CAR cell and a recognition polypeptide, the partial multi-component CAR cell and a recognition polypeptide can be administered together or separately. In embodiments where the subject is separately administered a partial multi-component CAR cell and a recognition polypeptide each of the compositions can be administered, separately, according to any of the dosages and administration routes/routines described herein.

Precise amounts of active ingredient required to be administered depend on the judgment of the practitioner and are particular to each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

In some embodiments, the methods further comprise administering the pharmaceutical composition described herein along with one or more additional chemotherapeutic agents, biologics, drugs, or treatments as part of a combinatorial therapy. In some such embodiments, the chemotherapeutic agent biologic, drug, or treatment is selected from the group consisting of: radiation therapy, surgery, antibody reagents, and/or small molecules.

In some embodiments of the methods described herein, the methods further comprise administering one or more chemotherapeutic agents to the subject being administered the pharmaceutical composition described herein. Non-limiting examples of chemotherapeutic agents can include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any one of the above.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins, such as small molecule toxins or enzymatically active toxins of bacterial, fungal, plant or animal origin, including fragments and/or variants thereof.

As used herein, the terms "chemotherapy" or "chemotherapeutic agent" refer to any chemical agent with therapeutic usefulness in the treatment of diseases characterized by abnormal cell growth. Such diseases include tumors, neoplasms and cancer as well as diseases characterized by hyperplastic growth. Chemotherapeutic agents as used herein encompass both chemical and biological agents. These agents function to inhibit a cellular activity upon which the cancer cell depends for continued survival. Categories of chemotherapeutic agents include alkylating/alkaloid agents, antimetabolites, hormones or hormone analogs, and miscellaneous antineoplastic drugs. Most if not all of these agents are directly toxic to cancer cells and do not require immune stimulation. In one embodiment, a chemotherapeutic agent is an agent of use in treating neoplasms such as solid tumors. In one embodiment, a chemotherapeutic agent is a radioactive molecule. One of skill in the art can readily identify a chemotherapeutic agent of use (e.g., see Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology $2^{nd}$ Edition, 2000 Churchill Livingstone, Inc; Baltzer L, Berkery R (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993). The bispecific and multispecific polypeptide agents described herein can be used in conjunction with additional chemotherapeutic agents.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one time administration and typical dosages range from 10 to 200 units (Grays) per day.

In some embodiments, the methods described herein can further comprise administering an additional immunotherapy to the subject. As used herein, "immunotherapy" refers to a diverse set of therapeutic strategies designed to induce the patient's own immune system to fight the tumor, and include, but are not limited to, intravesical BCG immunotherapy for superficial bladder cancer, vaccines to generate specific immune responses, such as for malignant melanoma and renal cell carcinoma, the use of Sipuleucel-T for prostate cancer, in which dendritic cells from the patient are loaded with prostatic acid phosphatase peptides to induce a specific immune response against prostate-derived cells, administration of cytokines, growth factors and/or signaling molecules that stimulate one or more immune cell type (e.g., interleukins), ex vivo expansion and/or stimulation of lymphocytes and/or dendritic cell specific for a tumor antigen prior to reintroduction to the patient, imiquimod, adoptive cell transfer, and/or the methods described, e.g., in International Patent Publication WO 2003/063792 and U.S. Pat.

No. 8,329,660. In some embodiments, the immunotherapy stimulates NK responses. In some embodiments, the immunotherapy is an adoptive cell transfer approach, i.e., adoptive immunothreapy.

In some embodiments, the methods described herein can further comprise administering an additional antibody, antigen-binding portion thereof, or T cell comprising a CAR to the subject. In some embodiments, the methods described herein can further comprise administering cytokine to the subject. Antibody- and cytokine-based therapies are known in the art and can include, by way of non-limiting example, alemtuzumab; bevacizumab; brentuximab vedotin; cetuximab; gemtuzumab; ibritumomab tiuxetan; ipilimumab; ofatumumab; pantibumumab; rituximab; tositumomab; trastuzumab; interleukin-2, and interferon-alpha.

The efficacy of a given treatment for cancer can be determined by the skilled clinician. However, a treatment is considered "effective treatment," as the term is used herein, if any one or all of the signs or symptoms of e.g., a tumor are altered in a beneficial manner or other clinically accepted symptoms are improved, or even ameliorated, e.g., by at least 10% following treatment with an agent as described herein. Efficacy can also be measured by a failure of an individual to worsen as assessed by hospitalization or need for medical interventions (i.e., progression of the disease is halted). Methods of measuring these indicators are known to those of skill in the art and/or described herein.

An effective amount for the treatment of a disease means that amount which, when administered to a mammal in need thereof, is sufficient to result in effective treatment as that term is defined herein, for that disease. Efficacy of an agent can be determined by assessing physical indicators of, for example cancer, e.g., tumor size, tumor mass, tumor density, angiogenesis, tumor growth rate, etc.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the active inregdient, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for tumor size or growth, among others. The dosage can be determined by a physician and adjusted, as necessary, to suit observed effects of the treatment.

Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response, (e.g. an inhibition of tumor growth). It is well within the ability of one skilled in the art to monitor efficacy of administration and/or treatment by measuring any one of such parameters, or any combination of parameters. Efficacy can be assessed in animal models of a condition described herein, for example treatment of cancer. When using an experimental animal model, efficacy of treatment is evidenced when a statistically significant change in a marker is observed, e.g. tumor size.

In some embodiments, the technology described herein relates to a pharmaceutical composition comprising a multi-component CAR (or portion thereof, or cell comprising a multi-component CAR) as described herein, and optionally a pharmaceutically acceptable carrier. In some embodiments, the active ingredients of the pharmaceutical composition comprise a multi-component CAR (or portion thereof, or cell comprising a multi-component CAR) as described herein. In some embodiments, the active ingredients of the pharmaceutical composition consist essentially of a multi-component CAR (or portion thereof, or cell comprising a multi-component CAR) as described herein. In some embodiments, the active ingredients of the pharmaceutical composition consist of a multi-component CAR (or portion thereof, or cell comprising a multi-component CAR) as described herein. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent as described herein.

In some embodiments, the pharmaceutical composition comprising a multi-component CAR (or portion thereof, or cell comprising a multi-component CAR) as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS©-type dosage forms and dose-dumping.

Suitable vehicles that can be used to provide parenteral dosage forms of a multi-component CAR (or portion thereof, or cell comprising a multi-component CAR) as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of an active ingredient can also be incorporated into the parenteral dosage forms of the disclosure, including conventional and controlled-release parenteral dosage forms.

Pharmaceutical compositions can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia PA. (2005).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the composition can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of cancer. A subject can be male or female.

A subject can be one who has been previously diagnosed with or identified as suffering from or having a condition in need of treatment (e.g. cancer) or one or more complications related to such a condition, and optionally, have already undergone treatment for cancer or the one or more complications related to cancer. Alternatively, a subject can also be one who has not been previously diagnosed as having cancer or one or more complications related to cancer. For example, a subject can be one who exhibits one or more risk factors for cancer or one or more complications related to cancer or a subject who does not exhibit risk factors.

A "subject in need" of treatment for a particular condition can be a subject having that condition, diagnosed as having that condition, or at risk of developing that condition.

In some embodiments, a nucleic acid encoding a multi-component CAR or portion thereof as described herein is comprised by a vector. In some of the aspects described herein, a nucleic acid sequence encoding a multi-component CAR or portion thereof as described herein, or any module thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence that is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

As used herein, the term "viral vector" refers to a nucleic acid vector construct that includes at least one element of viral origin and has the capacity to be packaged into a viral vector particle. The viral vector can contain the nucleic acid encoding a multi-component CAR or portion thereof as described herein in place of non-essential viral genes. The vector and/or particle may be utilized for the purpose of transferring any nucleic acids into cells either in vitro or in vivo. Numerous forms of viral vectors are known in the art.

By "recombinant vector" is meant a vector that includes a heterologous nucleic acid sequence, or "transgene" that is capable of expression in vivo. It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra chromosomal DNA thereby eliminating potential effects of chromosomal integration.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein an "antibody" refers to IgG, IgM, IgA, IgD or IgE molecules or antigen-specific antibody fragments thereof (including, but not limited to, a Fab, F(ab')2, Fv, disulphide linked Fv, scFv, single domain antibody, closed conformation multispecific antibody, disulphide-linked scfv, diabody), whether derived from any species that naturally produces an antibody, or created by recombinant DNA technology; whether isolated from serum, B-cells, hybridomas, transfectomas, yeast or bacteria.

As described herein, an "antigen" is a molecule that is bound by a binding site on an antibody agent. Typically, antigens are bound by antibody ligands and are capable of raising an antibody response in vivo. An antigen can be a polypeptide, protein, nucleic acid or other molecule or portion thereof. The term "antigenic determinant" refers to an epitope on the antigen recognized by an antigen-binding molecule, and more particularly, by the antigen-binding site of said molecule.

As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, and domain antibodies (dAb) fragments (see, e.g. de Wildt et al., Eur J. Immunol. 1996; 26(3):629-39; which is incorporated by reference herein in its entirety)) as well as complete antibodies. An antibody can have the structural features of IgA, IgG, IgE, IgD, IgM (as well as subtypes and combinations thereof). Antibodies can be from any source, including mouse, rabbit, pig, rat, and primate (human and non-human primate) and primatized antibodies. Antibodies also include midibodies, humanized antibodies, chimeric antibodies, and the like.

The VH and VL regions can be further subdivided into regions of hypervariability, termed "complementarity determining regions" ("CDR"), interspersed with regions that are more conserved, termed "framework regions" ("FR"). The extent of the framework region and CDRs has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917; which are incorporated by reference herein in their entireties). Each VH and VL is typically composed of three CDRs and four FRs, arranged from amino-terminus to carboxy-terminus in the following order: FR1, CDR1, FR2, CDR2, FR3, CDR3, FR4.

The terms "antigen-binding fragment" or "antigen-binding domain", which are used interchangeably herein are used to refer to one or more fragments of a full length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and CHi domains; (ii) a F(ab')2 fragment, a bivalent fragment including two Fab fragments linked by a disulfide bridge at the hinge region; (iii) an Fd fragment consisting of the VH and CHi domains; (iv) an Fv fragment consisting of the VL and VH domains of a single arm of an antibody, (v) a dAb fragment (Ward et al., (1989) Nature 341:544-546; which is incorporated by reference herein in its entirety), which consists of a VH or VL domain; and (vi) an isolated complementarity determining region (CDR) that retains specific antigen-binding functionality.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third nontarget entity. A reagent specific for a given target is one that exhibits specific binding for that target under the conditions of the assay being utilized.

Additionally, and as described herein, a recombinant humanized antibody can be further optimized to decrease potential immunogenicity, while maintaining functional activity, for therapy in humans. In this regard, functional activity means a polypeptide capable of displaying one or more known functional activities associated with a recombinant antibody or antibody reagent thereof as described herein. Such functional activities include, e.g. the ability to bind to a target.

A "cancer cell" is a cancerous, pre-cancerous, or transformed cell, either in vivo, ex vivo, or in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is associated with, e.g., morphological changes, immortalization of cells, aberrant growth control, foci formation, anchorage independence, malignancy, loss of contact inhibition and density limitation of growth, growth factor or serum independence, tumor specific markers, invasiveness or metastasis, and tumor growth in suitable animal hosts such as nude mice. See, e.g., Freshney, CULTURE ANIMAL CELLS: MANUAL BASIC TECH. (3rd ed., 1994). As used herein, the term "cancer" refers to an uncontrolled growth of cells that interferes with the normal functioning of the bodily organs and systems. A subject who has a cancer or a tumor is a subject having objectively measurable cancer cells present in the subject's body. Included in this definition are benign and malignant cancers, as well as dormant tumors or micrometastases. Cancers that migrate from their original location and seed vital organs can eventually lead to the death of the subject through the functional deterioration of the affected organs.

A "tumor" as used herein refers to an uncontrolled growth of cells tumor interferes with the normal functioning of the bodily organs and systems. The terms "cancer" and "malignancy" refer to a tumor that is metastatic, i.e. that is it has become invasive, seeding tumor growth in tissues remote from the original tumor site. A subject that has a cancer or a tumor is a subject having objectively measurable cancer cells present in the subject's body. Included in this definition are benign tumors and malignant cancers, as well as potentially dormant tumors or micrometastatses. Cancers that migrate from their original location and seed other vital organs can eventually lead to the death of the subject through the functional deterioration of the affected organs. Hematopoietic cancers, such as leukemia, are able to outcompete the normal hematopoietic compartments in a subject, thereby leading to hematopoietic failure (in the form of anemia, thrombocytopenia and neutropenia) ultimately causing death.

Examples of cancer include but are not limited to, carcinoma, lymphoma, blastoma, sarcoma, leukemia, basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma (GBM); hepatic carcinoma; hepatoma; intra-epithelial neoplasm.; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. cancer. The term "treating" includes reducing or alleviating at least one adverse effect or symptom of a condition, disease or disorder associated with a, e.g. cancer. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, $4^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

One of skill in the art can readily identify a chemotherapeutic agent of use (e.g. see Physicians' Cancer Chemotherapy Drug Manual 2014, Edward Chu, Vincent T. DeVita Jr., Jones & Bartlett Learning; Principles of Cancer Therapy, Chapter 85 in Harrison's Principles of Internal Medicine, 18th edition; Therapeutic Targeting of Cancer Cells: Era of Molecularly Targeted Agents and Cancer Pharmacology, Chs. 28-29 in Abeloff's Clinical Oncology, 2013 Elsevier; and Fischer D S (ed): The Cancer Chemotherapy Handbook, 4th ed. St. Louis, Mosby-Year Book, 2003).

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

T cells expressing chimeric antigen receptors (CAR), the fusion of single-chain variable fragments (scFv) and receptor signaling domains, have shown phenomenal successes in clinical trials against B cell malignancies 1, 2. CAR T cell, however, can have toxicities due to off-targeting and over-activation. Described herein are methods and compositions that provide improved safety and efficacy of CAR T cells by providing a universal approach for combinatorial, temporal, and logical control of multiple T cell signaling pathways.

In one embodiment, specificity can be enhanced by using CARs that can detect two antigens have been developed[3-6]. The ability to sense more than two antigens can further improve tumor specificity. In addition, even when CAR T cells are on target, adverse side effects can still occur when over-activation of T cells leads to cytokine release syndrome. Kill and ON switches have been developed to mitigate some of these side effects. Still, these switches serve mostly as master switches and consequentially lack fine control. Since control of natural T cell activation is achieved through a balance of multiple co-stimulatory and co-inhibitory signaling pathways 7, strategies that provide tunable and temporal control over such signaling pathways are important for optimizing CAR T cell performance. These challenges illustrate the need for intelligent controls of T cell response.

Figure 12:
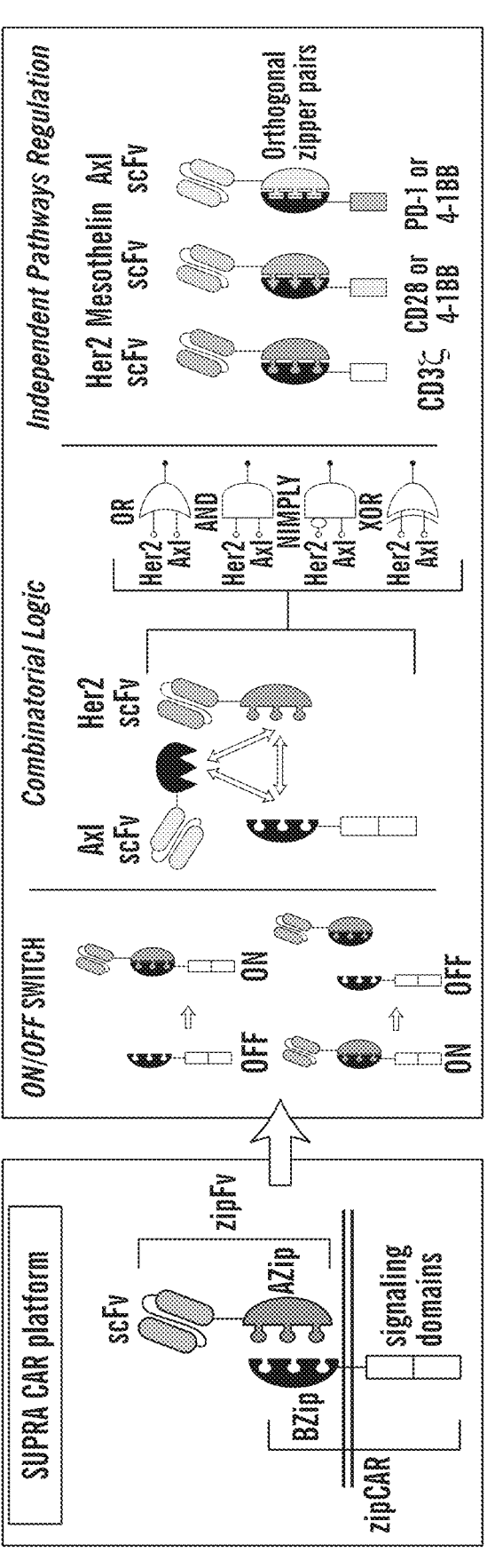
FIG. 12 depicts schematics of exemplary embodiments of aspects described herein.

Described herein is a universal CAR platform with the ability to (a) serve as an ON/OFF switch, (b) sense multiple antigens and perform logic computations, and (c) independently regulate multiple signaling pathways, will provide the necessary control for optimizing CAR T cell therapy. The split, universal, programmable and reconfigurable (SUPRA) CAR platform described herein is used for this purpose. Importantly the SUPRA CAR platform can accommodate new targets without further manipulation to patients' T cells. The SUPRA CAR platform is a two-component receptor system composed of a universal receptor expressed on T cells and a tumor-targeting scFv adaptor (FIG. 12). The universal receptor is generated from the fusion of intracellular signaling domains and a leucine zipper as the extracellular domain (zipCAR). The adaptor molecule is generated from the fusion of a cognate leucine zipper and a scFv (zipFv). The scFv on the zipFv binds to the antigen and the leucine zipper binds and activates the zipCAR on the T cells. This system also functions as a tunable switch with the zipFv as a titratable inducer. However, unlike other existing split CAR systems 8-11, described herein are orthogonal zipCAR/zipFv pairs, which permit control of multiple signaling pathways independently and performance of logic operations.

Described herein is:

Characterization of the SUPRA CAR platform as an ON/OFF switch. Design rules of the SUPRA CAR are provided in view of how various design parameters affect T cell activation.

Development of combinatorial logic operations with the SUPRA CAR platform.

Protein engineering approaches are utilized to develop cooperativity and competition in leucine zipper binding to generate a panel of 2-Input Boolean logic gates in a single receptor.

Development of SUPRA CAR to separately control multiple signaling pathways (signaling mixer). Orthogonal zipCARs were constructed to control CD3ζ, as well as co-stimulatory (e.g., CD28 and 4-1BB) and co-inhibitory (e.g., PD-1) signaling pathways independently for combinatorial and temporal regulation.

The SUPRA CAR platform was tested in vitro and in mouse models. The modular design affords high levels of specificity, flexibility, and precision as well as providing tools to improve the safety and efficacy of cellular cancer immunotherapy.

CAR T cell therapy. The transfer of tumor-targeting T cells to patients is a promising approach for cancer immunotherapy[1, 2]. In particular, CAR-modified T cells have demonstrated unprecedented efficacy against acute lymphoblastic leukemia, with around 90% complete remission being observed in clinical trials[1,2]. Despite these encouraging results, improvements can be made for CAR T cell therapy to be widely adopted for this and other cancers. In particular, improving the specificity and limiting the toxicity of CAR T cells without compromising efficacy.

The CAR design found in current clinical trials is comprised of a fixed, antigen-specific scFv fused to intracellular signaling domains derived from the T cell receptor (TCR) and other co-stimulatory receptors, such as CD28 and 4-1BB. These CARs can only detect one antigen and are therefore limited in their capacity to differentiate tumors from healthy tissues. In fact, a fatality was observed for a patient with metastatic colon cancer treated with T cells expressing anti-Her2 CARs because the T cells recognized low level of Her2 on healthy lung epithelial cells[12]. While significant efforts are underway to identify tumor-specific biomarkers, it remains an immensely challenging goal. In addition, the fixed design of current CARs makes it challenging to switch targets if the patient relapses due to insurgence of a clone not expressing the target antigen. Further, CARs targeting single antigens may also have limited efficacy against heterogeneous tumors. Therefore, a system that can sense multiple antigens, intelligently discern cancer from healthy tissue, and adapt to the dynamic and heterogeneous nature of tumor growth is highly desirable.

The current CAR design is also rigid with respect to the strength and timing of T cell activation. Further, this design is intractable to the addition or removal of signaling domains during the course of a treatment. This fixed design therefore stringently constrains the extent to which T cell function can be regulated. While CARs containing either CD28 or 4-1BB have demonstrated success in clinic trials, it remains uncertain whether current choices of signaling domains are ideal. For example, T cells expressing CARs with a CD28 domain have faster and stronger tumoricidal activity, but have shorter in vivo persistence. In contrast, T cells with CARs containing a 4-1BB domain have slower tumoricidal kinetics, but proliferate and survive better in vivo[13, 14] In addition, the fixed CAR design also triggers all signaling pathway on the CAR at the same level simultaneously. However, in one embodiment, the optimal CAR T cell response would involve different pathways being activated at varying levels and timescales. For example, in natural T cell activation conditions such as during influenza infection, 4-1BB signaling is not activated until 48-72 hours after the initial induction of the TCR and CD28 pathways[15-17] In such embodiments, CAR T cell response involves activating different signaling pathways at different times. Given that natural T cell activation is a dynamic process that involves many costimulatory signaling pathways, a CAR system that allows the tuning of separate costimulatory (or coinhibitory) pathways in a dynamic fashion, much like a music mixer for T cell signaling, will greatly facilitate the optimization of T cell response.

Even when CAR T cells are able to properly target tumors and achieve complete remission, adverse side effects (ASE) can be observed. The most common side effect of CAR T cell therapy is cytokine release syndrome (CRS), which is a combination of inflammatory symptoms resulting from cytokine elevations associated with rampant T cell activation and proliferation. While the management of CRS has improved[2], CRS remains a challenging and dangerous complication. Indeed, in a recent trial with anti-CD19 CAR T cells, a patient died due to CRS-associated complications[18]. In addition to CRS, neurotoxicity has also been observed in many patients treated with CAR T cells[1, 2], and four patients died in a recent trial due to cerebral edema. Given the varied and complex nature of these life-threatening side effects, preventing them, as opposed to managing them, is important. One way to minimize ASE development is to impart control over the timing, level, and persistence of CAR T cell activation. This can be achieved through regulating the amount of T cells injected into the patient. However, since T cells may still proliferate, it may just delay, rather than eliminate, CRS. A complementary strategy is to introduce switches into T cells such that their activity can be titrated with the administration of molecules, similar to ON/OFF switches. In one embodiments, one can introduce a "kill" switch.

Combinatorial antigen sensing is one strategy for improving the tumor specificity of CAR T cell therapy. Several technologies already exist for performing simple logic computations in engineered T cells. For example, two different antigen-specific scFvs have been fused together into one CAR, thus allowing either antigen to trigger T cell activation[3, 4]. These systems recapitulate an OR logic gate and can reduce the chance of tumor escape because mutations to two antigens by tumors are needed to avoid detection by CAR T cells. However, this tandem scFv CAR design can only perform OR logic. In addition to the OR gate, AND logic combinatorial CAR systems have also been created[5, 6], whereby T cells are transduced with an activation-deficient CAR with specificity directed towards one antigen, and a chimeric costimulatory receptor with specificity towards a second antigen. Moreover, the costimulatory signaling domain can be replaced with domains from inhibitory receptors, such as PD-119. These strategies, although successful, allow at most two CARs to be added together, and that cannot be extended to include more antigens.

Most of the current combinatorial CAR systems were designed to search and attack cells that display one or two specific antigens. However, some cancer cells may be classified by the absence, as opposed to the presence, of antigens. For instance, many cancer cells downregulate HLA expression to evade T cell response[22]. NK cells can detect and kill cells that are missing HLA[23]. This immune mechanism is robust as HLA is widely expressed in most cell types, and thus the absence of HLA can be interpreted as unusual and malignant. However, surface markers that are down-regulated in some cancers[24] are only expressed in a subset of tissues. As such, to precisely detect cancer cells that are missing non-ubiquitous antigens, one must also be able to detect antigens that specify or exclude the cell type of interest. This represents the logic of A BUT NOT B (A NIMPLY B) or Exclusive OR (XOR). A CAR platform that can perform these computations will be capable of detecting an extended range of tumors using novel mechanisms. Such a system will also expand the set of antigens that can be targeted by CAR T cells and thus ameliorate the need for novel and sufficient tumor antigens.

In addition to improving tumor specificity, controlling the timing and strength of CAR T cell activation level is critical for enhancing the safety profile of engineered T cell immunotherapies. Drug-inducible suicide genes (i.e., kill switches), such as inducible caspase 9[25] or human simplex virus thymidine kinase[26], such that the addition of small molecule inducers trigger the suicide genes and kill the engineered T cells that express them. These features allow clinicians to kill off the CAR T cells if CRS develops and becomes life-threatening. However, it remains uncertain whether killing the CAR T cells after CRS has developed can mitigate the ASE. In an alternative approach utilizes drug-controllable CARs can be used, whereby the addition of small molecules allows the CAR to transduce signals[27, 28]. Such ON switch systems can provide a temporal control that regulates T cell activation in a dose-dependent manner.

Another CAR design that can also serve as an ON switch is a split receptor configuration where the antigen recognition motif, usually a tumor-specific scFv, is dissociated from the signaling motif of the CAR; in such a configuration, the split receptor domains can be recruited to each other via biomolecular interactions. This split CAR configuration also allows a large panel of antigens to be targeted without reengineering the immune cells as it uses a universal receptor as the common basis for all interactions. Other embodiments are available for recruiting antigen recognition motifs to the signaling motifs on engineered T cells. The simplest version of such a split CAR design is accomplished through the fusion of a CD16 extracellular domain and intracellular TCR signaling domain. CD16 is a low-affinity Fc receptor that binds to the constant region of human IgG antibodies. The addition of the appropriate antibody triggers the activation of CD16 CAR T cells, and thus also acts as an ON switch[11]. Although convenient, this CD16 CAR may have many potential off-target effects through binding with endogenous antibodies produced by patients. Accordingly additional precautions are preferably used in addition to the CD16 and Fc pair, other heterodimerization domains, such as streptavidin and biotin[10], FITC and anti-FITC scFv[8], or peptide and anti-peptide scFv 9 have also been used to generate split CARs. In these designs, streptavidin or scFvs were fused to the TCR signaling domains and displayed on the T cell surface. Tumor-specific antibodies modified with biotin, FITC, or synthetic peptide served as an adaptor between cancer cells and T cells expressing split CARs, and were used to trigger T cell response. To date, these systems have only been used to control one CAR at a time. Orthogonal recruitment pairs will allow the control of multiple signaling pathways simultaneously, thus allowing combinatorial sensing and fine-balancing of different pathway activities.

Split, universal, programmable and reconfigurable (SUPRA) CAR platform For this work, the following functionalities are included in the SUPRA CAR platform described herein:

ON/OFF switch,

Logical decision-making based on detection of antigens, and

Independent and multiplexed tuning of different signaling pathways,

The SUPRA platform uses leucine zipper as the extracellular portion of the CAR and various signaling proteins as the intracellular domains (FIG. 12). The cognate leucine zipper is fused to an antigen specific scFv antibody. The administration of the antibody/zipper fusion activates the T cells, and thus serves as an ON switch in a dose-dependent manner. Leucine zippers are a class of protein domain that can form heteromeric structures through charge interactions[29]. Leucine zippers are beneficial for the SUPRA platform because many orthogonal pairs of leucine zippers are available, thus providing a large pool of candidates for design efforts[28]. Leucine zipper domains can also be engineered to compete with each other for the same binding partner, thus allowing inhibition and "NOT" functionality (FIG. 12). Moreover, we can utilize different affinities between leucine zipper pairs to engineer complex functions, such as OR, NIMPLY, AND, XOR (FIG. 12). There are 8 possible 2-Input Boolean logic behaviors that are not constitutively active (There are 16 possible 2-Input Boolean logic gates. However, only 8 of them (FALSE, A, B, OR, AND, A NIMPLY B, B NIMPLY A, and XOR) are inactive when no input is present.)

Furthermore, multiple orthogonal pairs permit CARs with split signaling domains (e.g., CD3$\zeta$, CD28, 4-1BB, PD-1), thus enabling independent and tunable control of these pathways (FIG. 12). Each individual CAR can be readily paired to scFvs that target different antigens, thus allowing combinatorial and logical antigen sensing. In vitro characterization can map SUPRA CAR platform responses (e.g., cytotoxicity, cytokine production, and memory T cell formation) to design parameters (e.g., zipCAR expression level, zipFv concentration, scFv affinity, and zipper affinity). The functionalities described herein can also be tested in vivo in mouse xenograft tumor models.

Current CAR designs have limited control and computing capabilities. These deficiencies render current CARs susceptible to dangerous over-activation and reduce CARs' ability to distinguish tumor cells from healthy tissues. Described herein are methods and compositions to address the control and computing capability by using, e.g., the SUPRA CAR platform to independently regulate multiple signaling pathways in T cells, which imparts logic and signaling mixer functions.

The methods and compositions provide advantages e.g., they provide the first function-rich, universal CAR platform featuring an ON/OFF switch, logical detection and integration, processing of >2 antigens, and independent regulation of different signaling pathways. These features have never been demonstrated together in a single system. In particular, provided herein is the first independent tuning of multiple signal pathways in T cells using CARs. Described herein are how different parameters can affect a split, universal CAR system, which will be useful for designing titratable ON/OFF CAR switches. Further described herein is the generation of the first complete set of two-input Boolean logic gates with CARs, including OR, NIMPLY, AND and XOR logic gates. This logic behavior will be very useful for improving the specificity of CAR T cells against cancer cells as well as for preventing tumor escape. In addition, some of the logic behaviors are interesting from a synthetic biology perspective because they are difficult to engineer. For example, XOR logic gates are one of the most difficult to engineer because each of the input signals has been able to activate and suppress output, depending on the presence the other input. Additionally, described herein is the development of the first CAR system that can integrate>2 antigens from cancerous and healthy cells to control multiple signaling pathways. For the first time in a CAR T cell system, it is possible to separately control CD3$\zeta$, CD28, 4-1BB and PD-1 signaling and explore how the timing and strength of activation for each pathway influences CAR T cell response and memory T cell formation.

Reagents and DNA constructs: Many zipCARs and zipFvs can be developed to systematically map the correlation between affinities, expression levels of the receptors, and the properties of the SUPRA CAR platform. As such, conclusions drawn from the results will be derived from the totality of an extensive set of reagents and conditions, as opposed to a few reagents commonly found in other studies. This will help ensure that anomaly from some reagents will not totally mask the functions of the SUPRA CAR.

Primary T cells: In some embodiments, primary T cells will be isolated from many anonymous donors. Results derived from one donor's T cells will be verified with T cells from another donor from the opposite sex.

Animals: Both male and female mice will be used to reduce the bias due to the sex of the mice.

Metric: A novel unbiased metric is described herein to determine the functional validity of a logic behavior (see below for more detail). To ensure transparency and facilitate data sharing, an innovative way to display key specifications and performance of genetic circuits in web-based datasheets has also been developed (available on the world wide web at datasheets.synbiotools.org/).

Characterization of the SUPRA CAR Platform as ON/OFF Switches

Figure 14A:
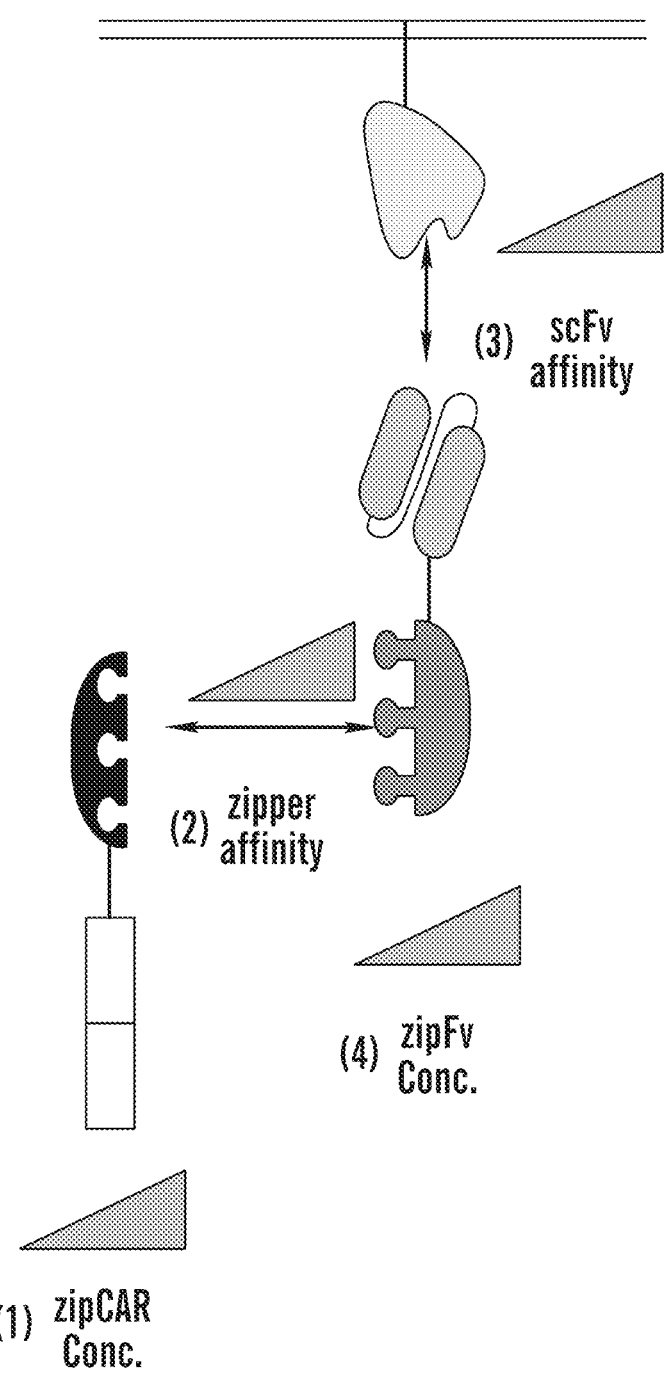
FIGS. 14A-14C demonstrate the characterization of parameters that can influence SUPRA CAR properties.

Key question: What are the relationships between design parameters of the SUPRA platform and T cell response? Described herein is the systematic characterization of how the (1) zipCAR expression level, (2) leucine zipper affinity, (3) scFv affinity, and (4) zipFv concentration ultimately influence T cell activation in vitro against antigen-expressing cells and in vivo against tumors (FIG. 14A).

Systematic characterization of the SUPRA CAR in vitro to gain insight into the design rules. It can be determined how changing the following parameters affect SUPRA CAR T cell activation:

(1) ZipCAR expression level: zipCAR can be introduced into primary human T cells via lentiviral transduction with varying multiplicity of infection to create T cells consisting of 3 separate levels of zipCAR expression. Expression of zipCARs can be verified with mCherry or myc staining measurement.

Figure 14C:
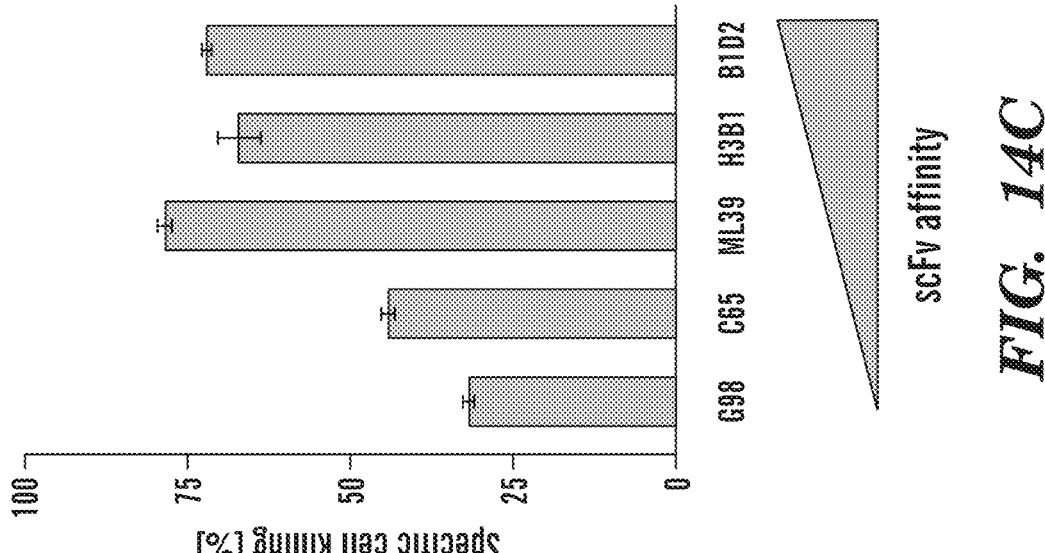
Figure 14B:
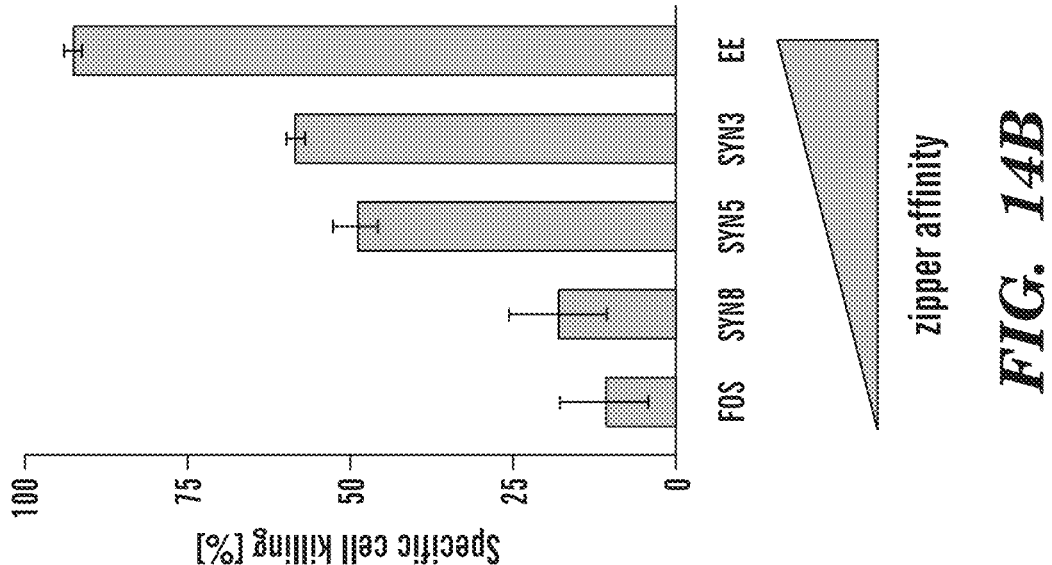

(2) Leucine zipper affinity: At least 3 different leucine zippers (AZIP) have been identified that can bind to the zipCAR BZIP with varying affinity, and zipFvs can be constructed using these AZIPs (FIG. 14B).

(3) scFv affinity: At least 3 anti-Her2 scFvs are available with different affinities that can be used to generate zipFvs (FIG. 14C). Together with the 3 leucine zipper pairs, at least 9 unique zipFvs can be purified. The proteins can be expressed in HEK293T cell and secreted into the media. The zipFvs can be purified with FPLC from the cell culture supernatant.

(4) ZipFv concentration: Varying amounts of zipFvs (e.g., 5 µg/ml, 0.5 µg/mL or 50 ng/mL) can be used in order to explore the dose-dependent nature of the SUPRA CAR platform.

Each condition outlined above can be tested with 3 effector to target (E:T) ratios (1:1, 10:1, 1:10). The target cancer cell line chosen for this experiment is a Her2+ breast cancer cell line called SK-BR-3 because it is a standard breast cancer cell line used in xenograft tumor models36. The SK-BR-3 line is modified with luciferase to facilitate in vitro cytotoxicity assays and in vivo imaging. For this experiment, different numbers of SK-BR-3 cells can be plated onto 96-well plates and grown overnight. The engineered T cells and zipFvs can be added to the 96-well plates containing the SK-BR-3 cells the next day. The number of T cells and the concentration of zipFvs to be added can be varied depending on the condition. T cell activation can be quantified, e.g., through measuring cytokine production of IL-2 and IFN-γ in the media using standard ELISA assays. Cytotoxicity against the SK-BR-3 cells can be measured by quantifying the remaining live cells (i.e., cells that were not killed by the T cells) through a luciferase assay[14]. CD69 expression on the T cell surface can be measured to determine the percentage of T cells that were activated.

Figure 15A:
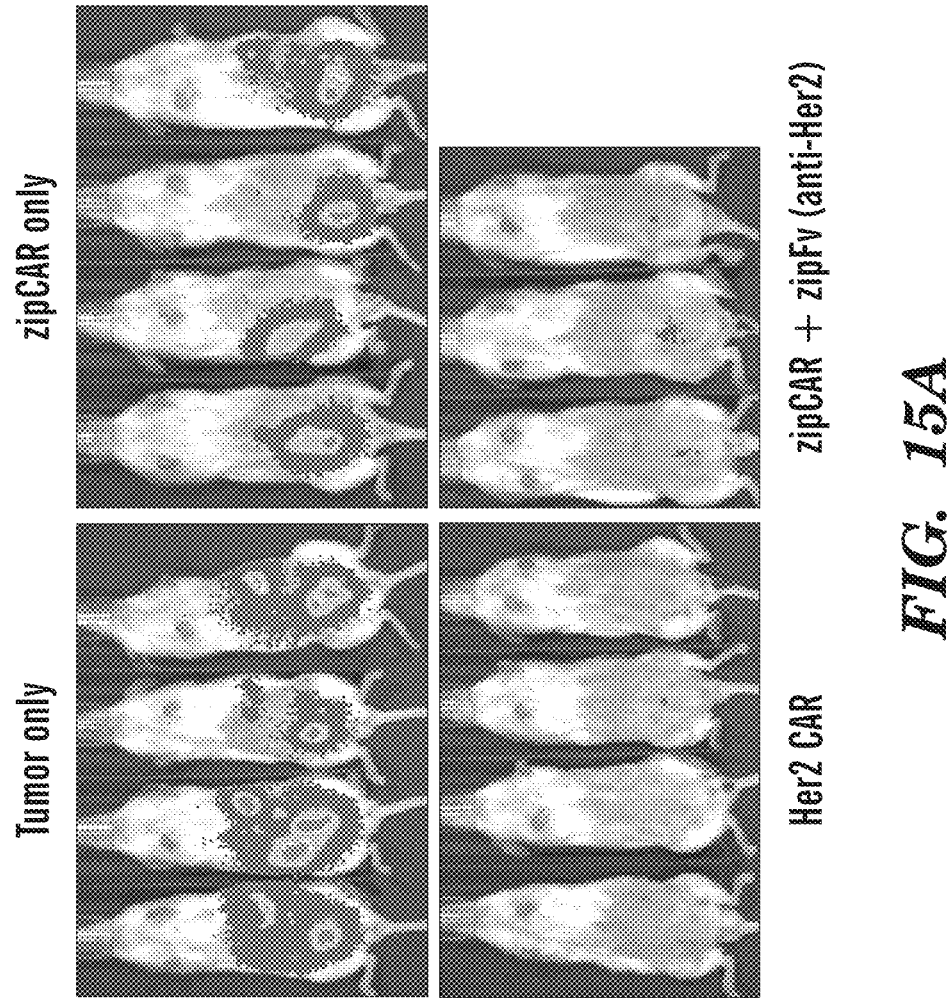
FIGS. 15A-15B demonstrate killing of established tumors in vivo by the SUPRA CAR platform.
Figure 15B:
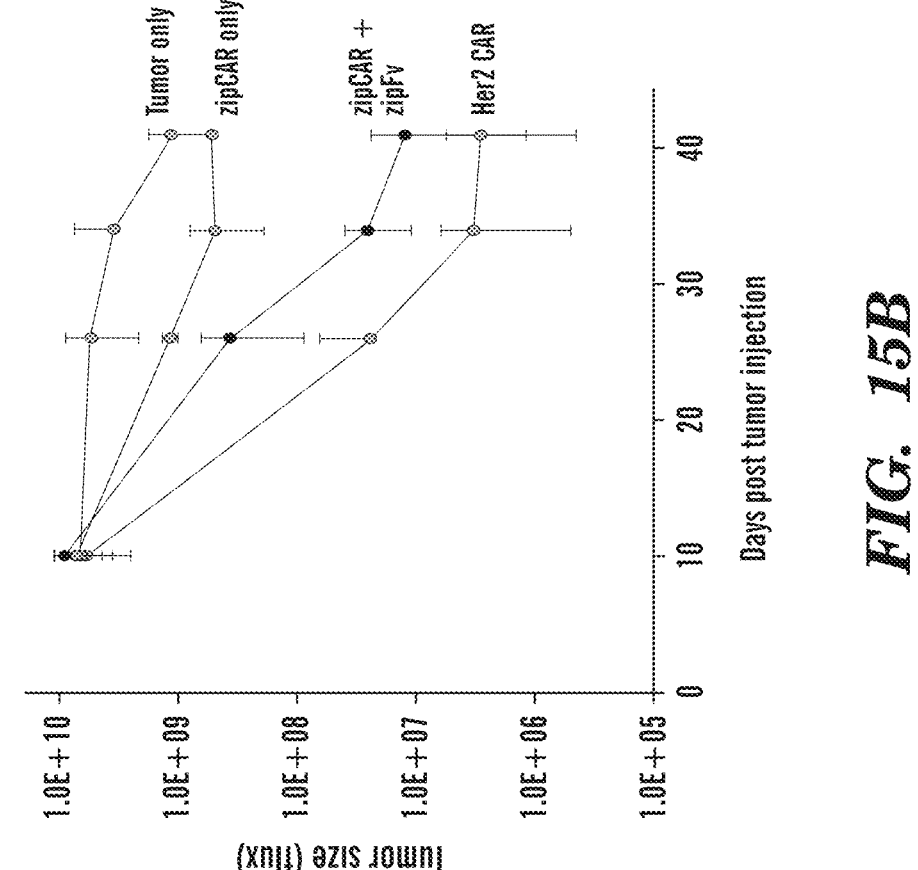

Mouse studies to verify activity and parameter correlations in vivo. How various parameters affect the anti-tumor activity of the SUPRA platform can be examined in a mouse xenograft tumor model. To test the performance of the SUPRA platform in a mouse xenograft tumor model, SK-BR-3 cells expressing luciferase can be implanted into immunodeficient mice (NOD scid gamma (NSG), 4-6 week old, Jackson Laboratory). Five million cancer cells can be implanted intraperitoneally (ip). After 14-20 days of tumor establishment, 5 million CD8+ T cells expressing the zip-CARs can be introduced via ip injection. Antibodies with different zipper and scFv affinities can be introduced via ip injection 1 day later. Six mice can be grouped together (3 male and 3 female mice) for each condition to reduce bias due to the sex of the mice. Tumor growth can be measured via luciferase and IVIS imaging. After 3 weeks, the mice can be sacrificed and the bone marrow and splenic cells harvested to determine the number of total T cells and other T cell subsets (e.g., central memory cells) via flow cytometry. Based on the experimental conditions described above, it was demonstrated that the SUPRA system can indeed alleviate tumor burden in the mouse tumor model (FIGS. 15A and 15B). The efficiency of the SUPRA platform is comparable to T cells expressing a full-length Her2 CAR. In addition, T cells expressing zipCAR did not reduce tumor size significantly without the corresponding zipFv.

Described herein is the mapping of the relationship between SUPRA CAR design parameters and the anti-tumor activity of the engineered T cells both in vitro and in vivo. This can provide design rules on how to effectively utilize the SUPRA system in future preclinical and clinical studies.

Develop Combinatorial Logics Operations with the SUPRA CAR Platform

Figure 16:
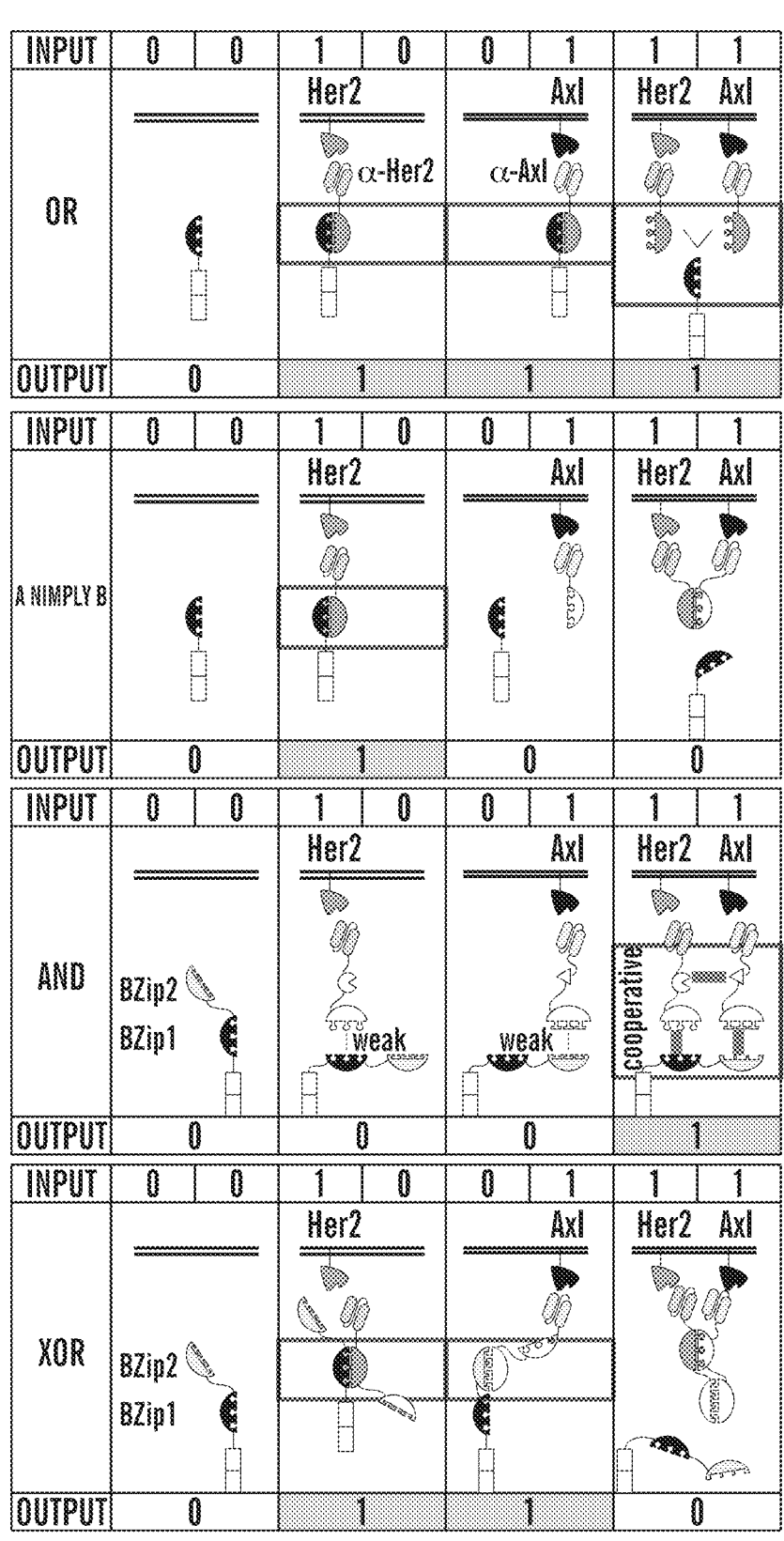
FIG. 16 depicts the design of SURPA CAR platform for logic operation. zipCARs and zipFvs designs that can be used to create Boolean logic operations. There are 8 possible 2-Input Boolean logic behaviors where the null state (no antigen or input) produces no output. Schematic diagrams are provided to demonstrate how the SUPRA system can be engineered to display OR, NIMPLY, AND, and XOR logic.
Figure 17:
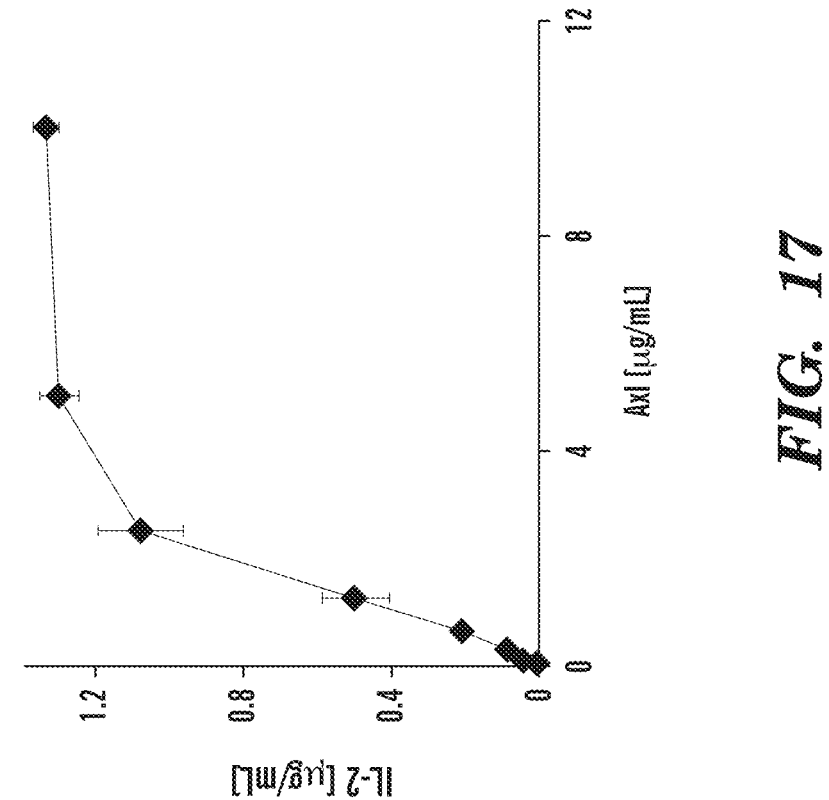
FIG. 17 depicts the design and characterization of a novel CAR against Axl. Dose response activity, as measured by IL-2 production, of the Axl CAR in human primary CD4+ T cells.

There are 8 possible 2-Input-1-Output logic gates where the no-input state (0,0) produces no output (FIG. 16). These logic gates will not generate constitutively active T cells, a requirement of safe and effective T cell therapy. Without wishing to be bound by theory, it is contemplated herein that the affinity of the scFv and leucine zipper can play an important role in determining the outcome for some of the logic behaviors (e.g., XOR, NIMPLY, and AND gates). Affinities that are too strong or too weak could compromise the performance of the system. Therefore, to design these logic operations into zipCARs, a library of leucine zippers and protein engineering approaches can be used to create zipCARs and zipFvs that can compete or bind cooperatively to achieve logic computation. The relationship between zipper/scFv affinity and CAR T logical detection of cancer cells can be determined. In all designs, only one zipCAR will be introduced into the T cells. To demonstrate the logic behavior, we can design zipFvs that target either Her2 or Axl. Axl is a receptor tyrosine kinase overexpressed in many cancers[37]. A novel CAR against Axl (FIG. 17) has been developed and the scFv against Axl can be used to generate zipFvs.

Three of the proposed receptor gates, FALSE, A only, and B only, can serve as controls for the other logic designs. The OR gate allows either or both of the two antigens to trigger T cell response. Thus, the OR gate can be useful for preventing tumor escape because mutations to two antigens are needed for the tumor to avoid detection by the engineered T cells. The AND gate can improve tumor targeting specificity by requiring two antigens to be present on the same tumor in order to activate T cell response. NIMPLY gates are useful for detecting a tumor that is marked by loss of one of the antigens. Similarly, XOR gates can detect tumor cells whose surface profile is distinguished by the loss of either of two antigens. Note that this type of inhibition is distinct from the inhibitory CAR (iCAR) design described below wherein the ligand binding triggers the PD-1 signaling pathway. This design represents an alternative strategy to iCARs and does not risk pushing the T cells into an anergic state.

Design and Characterization of Logic Operation in zipCARs Receptor Design:

FALSE, A only, and B only gates (FIG. 16): These logic behaviors serve as controls for the other logic designs and have been described above in this Example.

OR gate (FIG. 16): The OR gate is one of the simplest logics that can be achieved with the SUPRA platform. The presence of either or both of the two input signals can trigger the T cell response. To accomplish this logic behavior with SUPRA, a zipCAR can be first introduced into primary T cells via lentiviral transduction. Two zipFvs with the same leucine zipper, but with scFvs targeting either Her2 or Axl can be used. Note that this OR gate design can easily be scaled to accommodate more antigen inputs without further T cell engineering.

Figure 18:
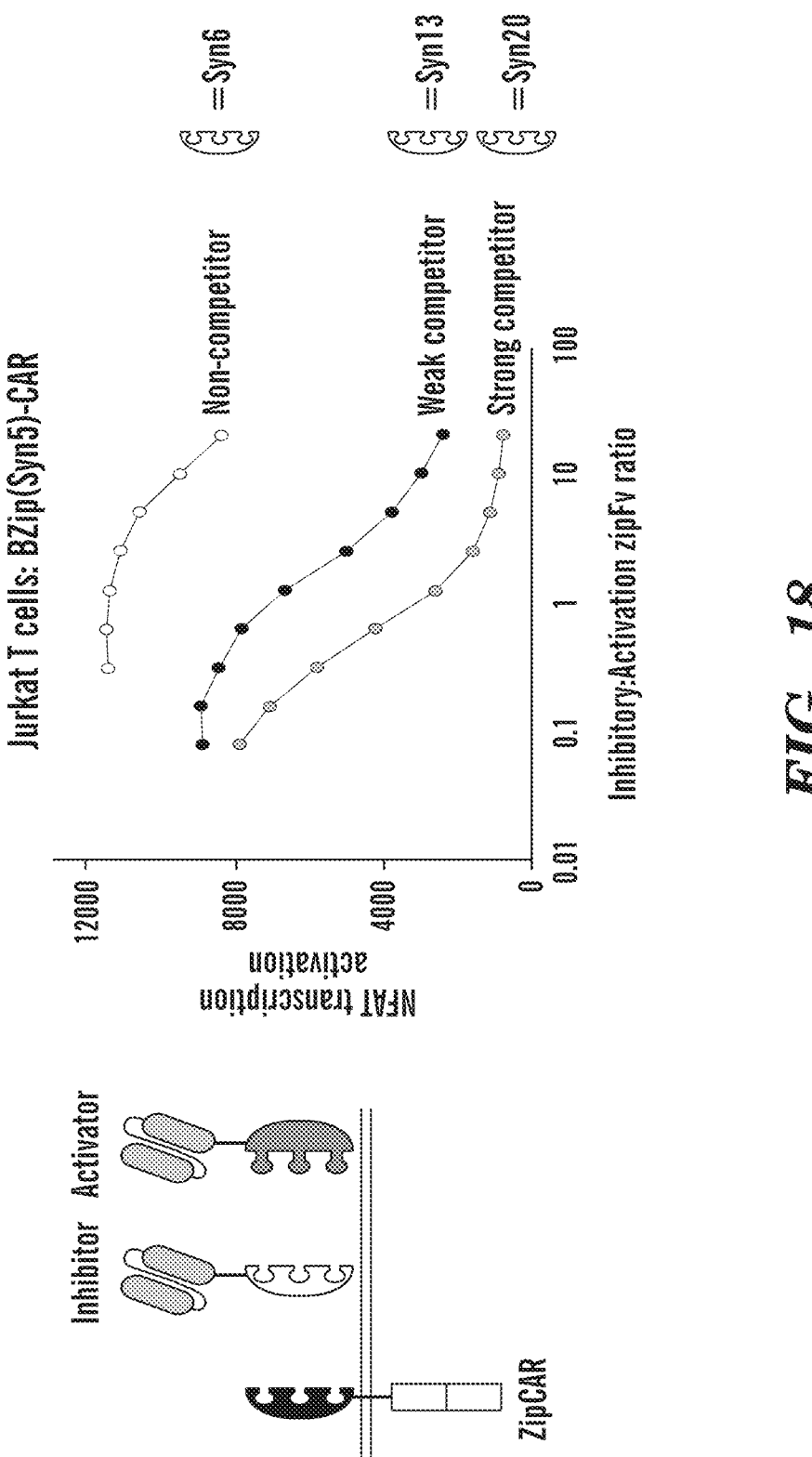
FIG. 18 demonstrates the design of inhibitor zipFvs through competitively binding leucine zippers. On the left is provided a schematic of an example of an inhibitory zipFv design where a BZIP is attached to an scFv and can compete with the zipCAR for the activating zipFv to inhibit its activation. On the right is a graph of Jurkat activation, as measured by NFAT transcription activation, by zipCARs and activating anti-Her2-AZIP zipFv. As shown, activation can be reduced by competing anti-Her2-BZIP zipFvs. Changing the zipper affinity can modulate the level of reduction. Non-competing BZIP (syn6) did not reduce zipCAR activation.

NIMPLY B and B NIMPLY A gates (FIG. 16): In a NIMPLY logic gate, only one input can trigger the output and the presence of the second input turns the system off. For example, A NIMPLY B means that only cancer cells with antigen A will trigger a response. Cells expressing no antigen, antigen B only, or antigen A and B will not activate the SUPRA CAR. To accomplish this logic behavior with SUPRA, two zipFvs with different leucine zippers (e.g., Her2-AZIP and Axl-BZIP-weak) can be designed. The weak BZIP on the Axl zipFv can bind to the Her2-AZIP zipFv, but with weaker affinity than the BZIP on the zipCAR. When only Her2 is present on a cell, the Her2-AZIP will bind to the receptor and trigger T cell activation. However, when both Her2 and Axl are present on the same cell, the scFv-antigen binding can provide the proximity cooperativity needed to competitively saturate the Her2-AZIP with Axl-BZIP-weak, and the T cells can not be activated It is demonstrated herein that competitive zipper binding can be effective in blocking zipCAR activation. Four anti-Her2 zipFvs, one with an AZIP (activating) and the other three with BZIP that binds the AZIP either strongly or weakly were generated. The anti-Her2-AZIP zipFv can activate the zipCAR, and the anti-Her2-BZIP can robustly inhibit the activation triggered by the anti-Her2-AZIP in a dose-dependent manner (FIG. 18).

two Axl scFvs and 5 Her2 scFvs38 are available with varying affinities. Variants of inhibitory scFvs for NIMPLY gates using combinations of scFvs and BZIP affinity variants can be constructed. The identity of the AZIP on the activating zipFv remains unchanged. The BZIP on the zipCAR also remains constant. The zippers can be derived from the library of zippers that have been tested as described elsewhere herein. More zipper variants can be generated based on protein engineering principles described in the literature[30] by altering the interacting residues on the zipper.

AND gate (FIG. 16): To generate AND gates, two zipFvs can be created that bind weakly to the zipCAR, but can bind much tighter to the zipCAR when both zipFvs are bound antigen on the same cell because of the cooperative interaction between the two zipFvs. Two orthogonal BZIP zippers can be attached onto a zipCAR. The two corresponding AZIPs can be attached to each of the zipFvs. Lastly, an orthogonal heterodimeric interaction domain can also be attached to each zipFv to allow for a weak interaction between the two zipFvs. This combination of weak interactions between the zipFvs and zipCAR can provide the cooperativity needed to ensure that zipCAR T cells are only activated in the presence of both zipFvs. DZ domains and their corresponding ligands can be used as the orthogonal heterodimeric interaction domains on the zipFvs because many weakly interacting PDZ/ligand pairs are available[39] and have been used for engineering cooperativity in signaling proteins or transcription factors[41-42]. A small library of zipCARs and zipFvs composed of PDZ and zipper domains can be generated to identify a set of domains that can function as an AND gate.

XOR (FIG. 16): To generate a XOR gate, two orthogonal BZIP zippers can be attached onto a zipCAR, similar to the AND gate. The corresponding orthogonal AZIP zippers can be attached onto zipFvs such that each can bind the receptor on a different BZIP. In addition, each zipFv can also be equipped with a BZIP-weak the other zipFV such that the presence of both zipFvs does not activate the receptor. However, the affinity of the BZIP-weak is low enough such that it requires cooperative binding through antigens and does not allow zipFvs to bind in solution. Therefore, the two zipFvs only inhibit each other when they are bound to the same cells through their scFvs and thus prevent both zipFvs from activating the zipCAR. Similar to the other logic gates, a series of zipFvs with varying BZIP affinities to the AZIP can be generated to identify the optimal design.

Receptors Characterization:

ZipCARs can be introduced into primary T cells (i.e., CD4 and CD8) via lentiviral transduction. Expression of zipCARs can be quantified with myc staining and flow cytometry. ZipFvs can be produced in HEK293T cells and purified with FPLC. To determine the logic behavior of the SUPRA system in vitro, the system can be activated by mixing the engineered T cells and zipFvs with SK-BR-3 cells expressing (a) no ligand, (b) Her2 only, (c) Axl only, or (d) Her2 and Axl. The no-ligand SK-BR-3 line can be generated with CRISPR-Cas9 knockout of Her2. Axl can be introduced into SK-BR-3 via lentiviral transduction. These 4 SK-BR-3 lines represent the 4 possible Boolean logic inputs for this aim. Each system can be tested with 3 E:T ratios. The zipFv concentrations and zipCAR expression, in addition to the zipper and scFv affinities, can be varied. T cell activation can be monitored by measuring cytokine production (i.e., IL-2, and IFN-γ), cytotoxicity against tumor cells, and CD69 expression on the T cells.

To quantitatively determine the logic performance of these receptors without bias, a metric called Vector Proximity (VP) has been developed. VP measures the misalignment between a circuit's biological implementation and its ideal implementation from its intended truth table. Truth tables and obtained experimental results are represented as vectors, Truth Table and Signal Vectors, respectively, in a 4-dimensional vector space. The angular error between these two vectors (VP angle metric) is calculated with 0° meaning the data represents the intended truth table perfectly and 900 meaning the data demonstrates completely incorrect output (inverted response to the intended truth table). For any implemented circuit its VP angle is measured from all 16 possible 2-Input Boolean logic truth tables and the results sorted in ascending order. The rank of the intended truth table in this sorted list is defined as the circuit's VP global rank. Note that each output measurement (e.g. cytotoxicity, cytokines, CD69) has its own VP angle and global rank. A circuit is called as functionally valid under this measure if it has the best (that is, smallest) VP global rank for all of the outputs. The best receptor is the one that is functionally valid and has the largest differences between ON and OFF states (dynamic range).

Characterization of logic behavior of zipCARs in a mouse xenograft tumor model. A fairly standard in vivo tumor model can be used where the 4 SK-BR-3 cancer cell lines described above are introduced via ip injection in separate mouse groups. These cell lines are implanted into NSG mice and tumors allowed to grow for 2 weeks. Five million T cells containing zipCARs are introduced into the mice via ip injection. ZipFvs are also injected via ip injection 1 day later. For some of the gates with several functional sets of zipFvs, as least two of the sets are tested to determine which works better in vivo. Five mice are grouped together for each of the combinations. Tumor growth is measured with luciferase and IVIS imager. After 3 weeks, the mice are sacrificed and the bone marrow and splenic cells are harvested to determine the number of distinct T cell subsets via flow cytometry. Six mice are grouped together (3 male and 3 female mice) for each condition to reduce bias due to the sex of the mice. The 8 possible 2-Input logic receptors are tested and the VP metric used to objectively determine the logic performance of the receptors in vivo.

Described herein is the design and characterization of a set of zipCARs and zipFvs to perform logic operations that are unmatched by any current CAR designs, thus delivering an intelligent platform for providing precision medicine to cancer patients.

Parameters such as the linker length between the zippers and the order of the zippers can be varied, to identify the best zipCAR design.

The design can also be modified to include 3 zippers such that 3 inputs can be processed by the same receptor and more complex logics can be achieved. Additionally, a library of leucine zipper and PDZ-ligand pairs with varying affinities are provided so that they can be used for more complex SUPRA CAR designs.

Development of SUPRA CAR to Control Multiple Signaling Pathways

Triggering co-stimulatory pathways, such as CD28 and 4-1BB, can lead to both fast tumoricidal activity and more central T cell formation. Activating PD-1 signaling pathways only on the engineered T cells can temper overactive CAR T cells and lower the risk of developing adverse side effects. Orthogonal zipCARs with different intracellular signaling domains and leucine zippers can be examined to address how strength and activation timing of each pathway contribute to the overall T cell response, T cell differentiation, and antitumor effect.

Design, Build, and Characterize Orthogonal zipCARs with Different Signaling Domains.

Figure 19A:
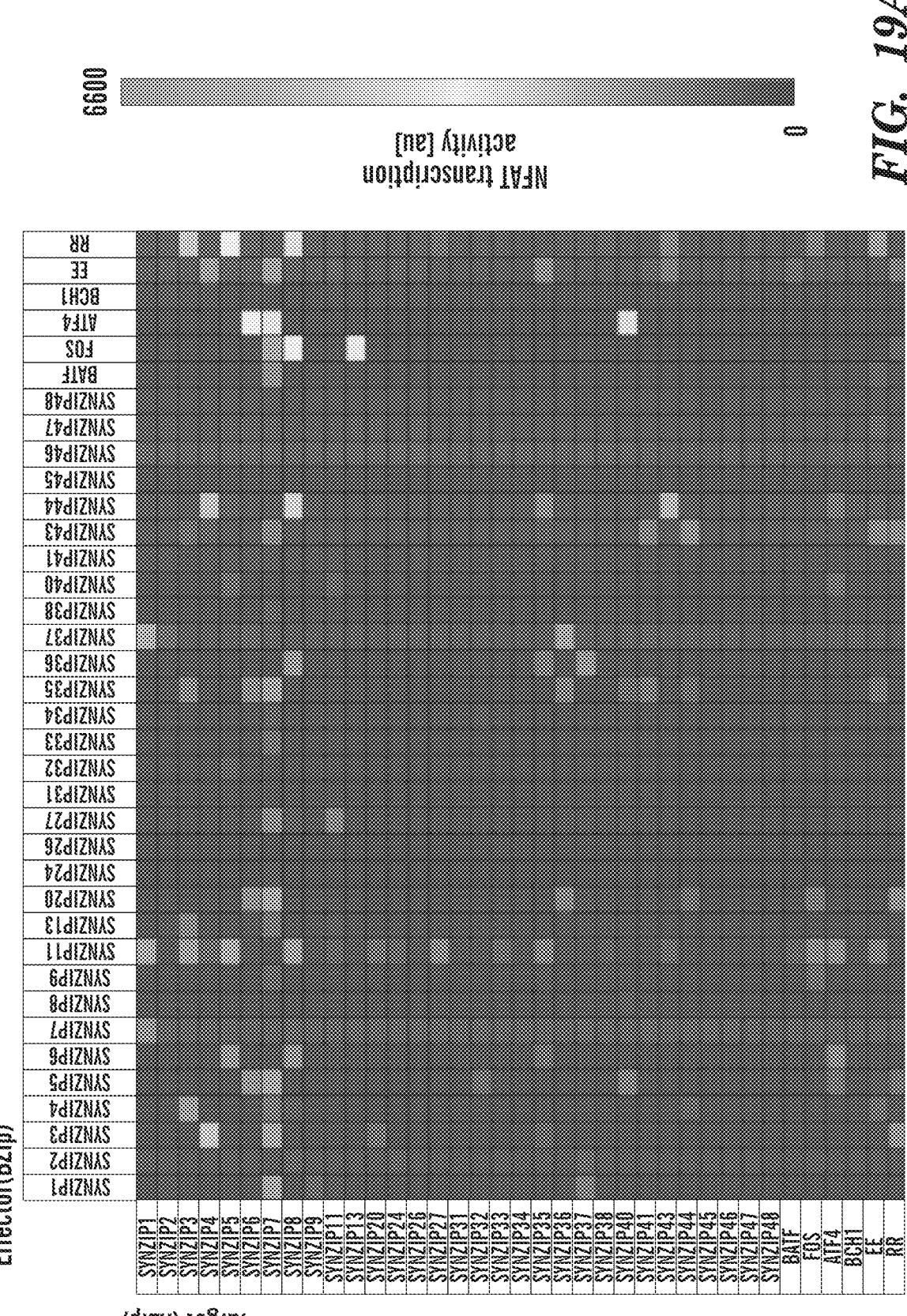
FIGS. 19A-19C demonstrate the use of orthogonal leucine zippers and PD-1 signaling domain in SUPRA CAR platform.
Figure 19C:
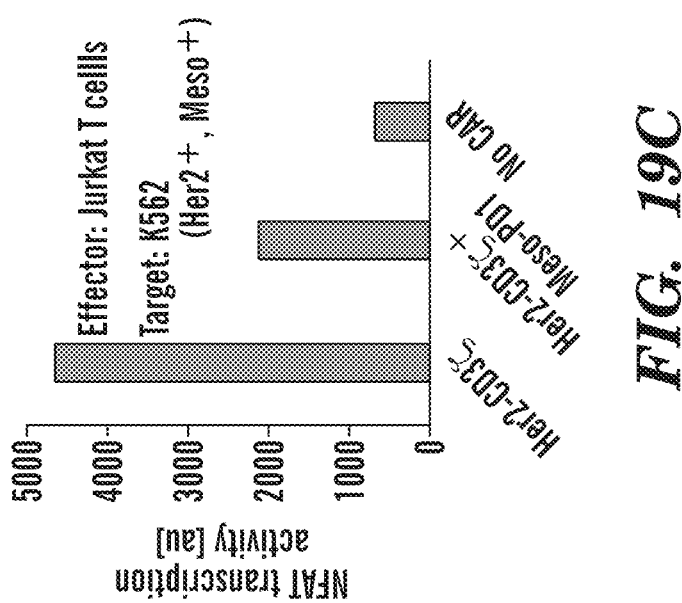
Figure 19B:
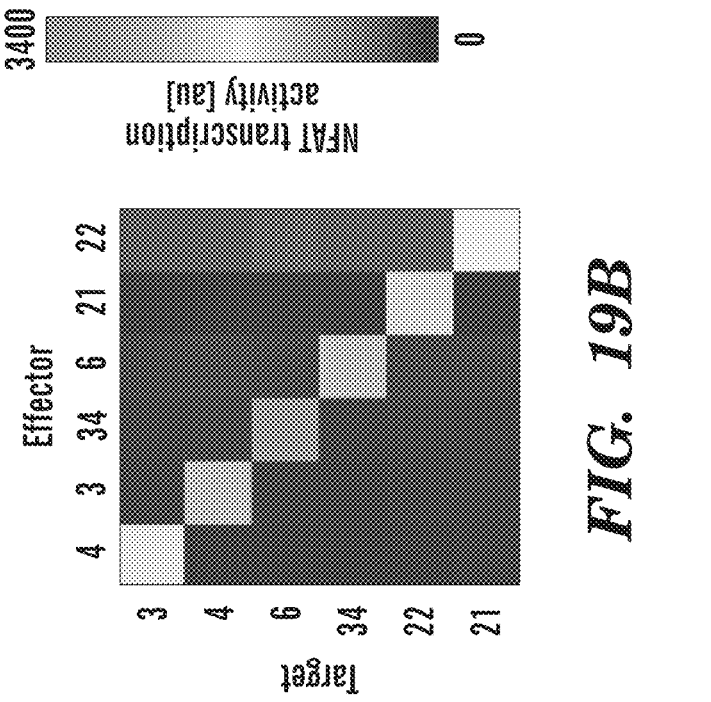

40 leucine zipper pairs[43] have been screened within the SUPRA CAR platform in Jurkat T cells (FIG. 19A) and 3 orthogonal zipper pairs (FIG. 19B) have been identified that are compatible with the SUPRA platform. These zippers can be used to create orthogonal zipCARs with CD37, CD28, 4-1BB and PD-1 signaling domains. These zipCARs are transduced into T cells using a lentiviral vector as described above. For example, demonstrated herein is the generation of an inhibitory CAR with a PD-1 intracellular signaling domain which inhibits the activation of a different CAR in Jurkat T cells. (FIG. 19C).

Testing CD3γ, CD28, and 4-1BB zipCARs: To verify how the zipCARs with different signaling domains function in T cells, both human CD4 and CD8 primary T cells are transduced with the zipCARs via lentiviral transduction. Cells are allowed to reach resting states (~12 days) before starting the characterization experiments. In order to test the functionality of zipCAR CD28 and 4-1BB domains, zipCARs containing these domains are introduced separately into T cells already stably expressing an anti-Her2 CAR containing only the CD3ζ signaling domain. The behavior of these zipCARs is compared to full-length (traditional) Her2-CARs that already contain the respective signaling domains. Expression of the zipCARs is verified with anti-myc staining and flow cytometry. In killing assays, K562 cells expressing Her2 and luciferase are utilized as the antigen presenting cells. The corresponding anti-Her2 zipFvs are added to activate the zipCARs. Additionally, the antibody concentrations can be varied and zipFvs with different zipper affinities generated to determine how these parameters affect T cell response. The IL-2 production and CD69 expression of the T cells is measured to determine activation level. T cell proliferation is monitored via cell counting. Activation of CD28 leads to a higher percentage of central memory T cells compared to activation of 4-1BB[13, 14] Therefore, surface markers such as CCR7 and CD45RO are monitored via flow cytometry to determine the relative level of central memory or effector memory T cells with and without stimulation.

Testing PD-1 zipCARs: To verify whether zipCARs with PD-1 signaling domains can inhibit T cell activation, zipCARs are introduced via lentiviral transduction into primary T cells that already contain an anti-Her2 CAR. The T cells are activated with Her2+ K562 cells and inhibited with the zipFv. The antibody concentration and zipper affinity can be varied and these parameters can be used to affect the inhibition of T cell response. The inhibition is monitored by measuring IL-2 production, CD69 expression, and proliferation.

Figures 20, 21:
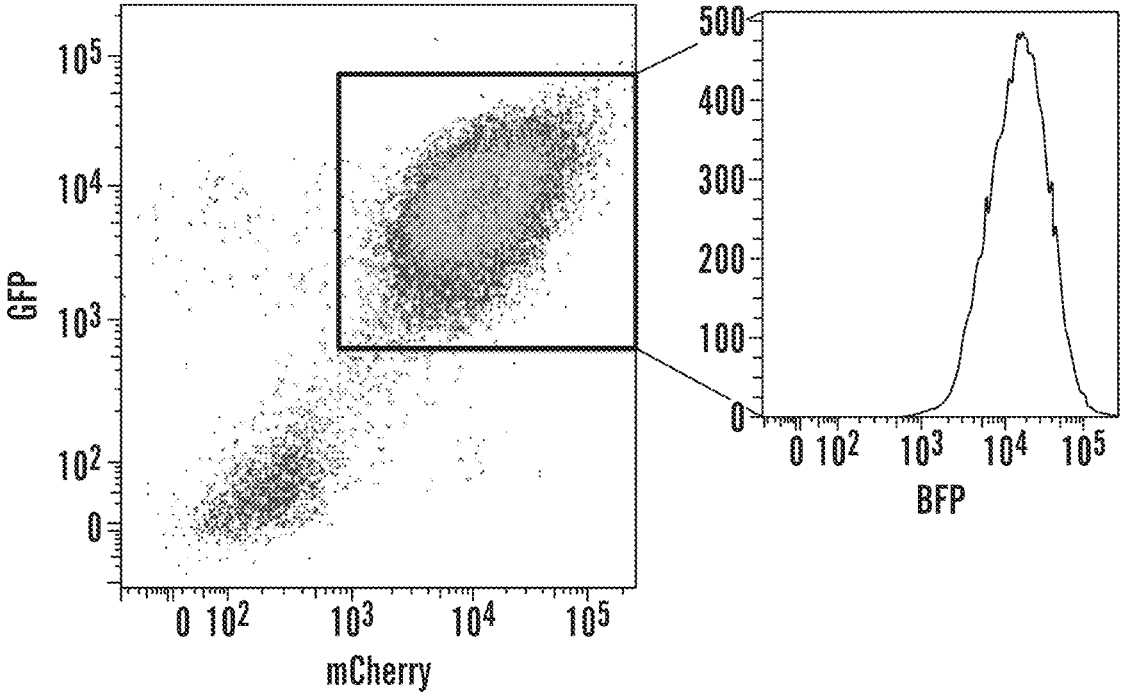
FIG. 20 depicts exemplary behaviors from SUPRA CARs controlling different pathways.
FIG. 21 depicts multiplexed PiggyBAC integration into human T cells. Three piggyBAC vectors, each expressing GFP, mCherry, or BFP and three different antibiotic resistance genes separately, were integrated into Jurkat T cells simultaneously. After selections on three antibiotics, more than 85% of cells express all three fluorescent reporter proteins.

Characterization of multiplexed control of zipCARs in vitro. Combinatorial control of different signaling pathways using zipCARs: To demonstrate separate control of signaling pathways in the same T cell, 3 zipCARs with various signaling domains are introduced into primary T cells via two sequential lentiviral transductions. Each zipCAR also has orthogonal zippers and epitope tags. 2 sets of zipCARs are depicted in FIG. 20. This collection of zipCARs displays a wide variety of behaviors depending on the zipFv attached to each scFv. In FIG. 20, the logic operations and phenotypes are derived by assuming that all three zipFvs target different antigens to generate 3-input logic behaviors. However, these zipCARs can be easily adapted to target fewer antigens. In addition, not all the zipCARs need to be activated at the same time.

zipFvs against Her2, Axl, and Mesothelin can be generated. With three different input ligands, there are 8 possible combinations: (1) no ligand, (2) Her2 only, (3) Axl only (4) Mesothelin only, (5) Her2+ Axl, (6) Her2+ Mesothelin, (7) Axl+ Mesothelin, (8) or Her2+ Axl+ Mesothelin. All 8 possible target cell lines can be generated by stably over-expressing the extracellular portions of Her2, Axl and/or Mesothelin in K562 cell lines. This set of new K562 lines also constitutively expresses luciferase and mCherry genes. Luciferase can be used for in vitro cytotoxicity assays and in vivo imaging, while mCherry marks the cells for flow cytometry analysis. Central memory T cell surface makers and cytokine production are monitoried as well as the cytotoxicity against the cancer cell lines.

Multiplexed dose response profile of individual pathways: The orthogonal zipCARs equipped with different signaling pathways afford a unique opportunity to activate each pathway at different levels, a property that is unachievable with the current, fixed CAR design. For the two set of zipCARs outlined in FIG. 20, in vitro dose-response analysis for each pathway can be conducted with T cells that contains all three zipCARs and 5 different zipFv concentrations for each zipCAR. In this experiment, each zipFv has the same anti-Her2 scFv. The target cells are Her2+K562 cells. Cytokine production (i.e., IL-2 and IFN-7) is measured via ELISA and cytotoxicity of the K562 cells. Surface markers such as CCR7 and CD45RO are also measured to determine the relative levels of central and effector memory T cells with and without stimulation.

Temporal control of individual pathways: In addition to different levels of activation, each pathway governed by the orthogonal zipCARs can be triggered at different times. The relative timing of CD28 and 4-1BB activation can influence CAR T cell response and memory T cell formation. zipCARs that control CD3ζ and CD28 can be activated simultaneously at the beginning of the experiment. The zipCAR that controls 4-1BB is then be activated at 0 h, 8 h, 16 h, 24 h, 48 h, 72 h, or 96 h after the initial activation of CD3ζ and CD28 using Her2+K562 cells and anti-Her2 zipFvs. Again, cytokine production is measured via ELISA and cytotoxicity. Surface markers such as CCR7 and CD45RO are also measured to determine the relative levels of central or effector memory T cells.

Characterization of multiplexed control of zipCARs in mouse xenograft tumor model. Multiplexed control of T cell signaling can be achieved with a set of orthogonal zipCARs in vivo. The zipCARs contain a myc, FLAG, or HA epitope tag and are cloned into 2 lentiviral vectors. To analyze the two sets of zipCARs, the lentivirus is introduced into human primary T cells via two sequential transductions. Expression of the zipCARs is verified with anti-epitope tag staining and flow cytometry. The 8 engineered K562 cell lines are implanted subcutaneously into NSG mice and allowed to grow for 2 weeks. T cells containing zipCARs are then introduced into the mice via ip injection. All three zipFvs are injected via tail-vein injection 1 day later. Six mice are grouped together (3 male and 3 female mice) for each condition to reduce bias due to the sex of the mice. Tumor growth is measured via luciferase assay and IVIS imaging. After 3 weeks, the mice are sacrificed and the bone marrow and splenic cells are harvested to determine the number of distinct T cell subsets via flow cytometry.

To evaluate the multiplexed dose-response profile of the SUPRA system in vivo, the same set of T cells described above is utilized, but the three zipFvs are injected into the mice at different doses. The tumor cells are K562 expressing Her2 only. The rest of the experiment is the same as the one described above.

To evaluate the temporal control of the SUPRA system in vivo, the same sets of T cells are used again, but the zipFv for 4-1BB is added at 0 h, 24 h, 48 h, 72 h, or 96 h after the addition of zipFvs for CD3ζ and CD28. The tumor cells implanted are K562 expressing Her2 only. The rest of the experiment will be the same as the one described above.

Described herein is a collection of orthogonal zipCARs that can flexibly control multiple signaling pathways in human T cells. These zipCARs are the basis of a new class of CAR when treating tumors with precision is necessary (e.g., one antigen is not sufficient to describe the tumor). When coupled with the receptor design outlined above, the increased number of available logic operations permits efficient identification of tumor cells.

To enhance the lentiviral transduction efficiency of transgenes such as CARs, activation of the T cell receptor (TCR) is often performed prior to the transduction procedure. The activation of the TCR can complicate the analysis of memory T cell formation because the activation step can drive T cell differentiation into different memory cells. An alternative approach for introducing transgenes is through the transient transfection of in vitro transcribed RNA that codes for the transgenes. It is contemplated herein that the zipCARs are be cloned into a vector specifically designed for in vitro RNA transcription[44]. zipCAR RNAs can be generated using commercially available kits and transfected into resting primary CD4 or CD8 T cells through nucleofection.

It is further contemplated that zipCARs can be delivered by transposases, such as PiggyBAC45 or Sleeping Beauty[46]. These systems have much higher gene delivery capacity and it is demonstrated herein that 3 separate plasmids can be simultaneously integrated into human T cells using Piggy-BAC (FIG. 21).

REFERENCES

1. Maude, S. L. et al. Chimeric antigen receptor T cells for sustained remissions in leukemia. *N Engl J Med* 371, 1507-1517 (2014).

2. Davila, M. L. et al. Efficacy and toxicity management of 19-28z CAR T cell therapy in B cell acute lymphoblastic leukemia. *Sci Transl Med* 6, 224ra225 (2014).
3. Zah, E., Lin, M. Y., Silva-Benedict, A., Jensen, M. C. & Chen, Y. Y. T Cells Expressing CD19/CD20 Bispecific Chimeric Antigen Receptors Prevent Antigen Escape by Malignant B Cells. *Cancer Immunol Res* 4, 498-508 (2016).
4. Grada, Z. et al. TanCAR: A Novel Bispecific Chimeric Antigen Receptor for Cancer Immunotherapy. *Mol Ther Nucleic Acids* 2, e105 (2013).
5. Kloss, C. C., Condomines, M., Cartellieri, M., Bachmann, M. & Sadelain, M. Combinatorial antigen recognition with balanced signaling promotes selective tumor eradication by engineered T cells. *Nat Biotechnol* 31, 71-75 (2013).
6. Lanitis, E. et al. Chimeric antigen receptor T Cells with dissociated signaling domains exhibit focused antitumor activity with reduced potential for toxicity in vivo. *Cancer Immunol Res* 1, 43-53 (2013).
7. Chen, L. & Flies, D. B. Molecular mechanisms of T cell co-stimulation and co-inhibition. *Nat Rev Immunol* 13, 227-242 (2013).
8. Ma, J. S. et al. Versatile strategy for controlling the specificity and activity of engineered T cells. *Proc Natl Acad Sci USA* 113, E450-458 (2016).
9. Rodgers, D. T. et al. Switch-mediated activation and retargeting of CAR-T cells for B-cell malignancies. *Proc Natl Acad Sci USA* 113, E459-468 (2016).
10. Urbanska, K. et al. A universal strategy for adoptive immunotherapy of cancer through use of a novel T-cell antigen receptor. *Cancer Res* 72, 1844-1852 (2012).
11. Kudo, K. et al. T lymphocytes expressing a CD16 signaling receptor exert antibody-dependent cancer cell killing. *Cancer Res* 74, 93-103 (2014).
12. Morgan, R. A. et al. Case report of a serious adverse event following the administration of T cells transduced with a chimeric antigen receptor recognizing ERBB2. *Mol Ther* 18, 843-851 (2010).
13. Kawalekar, O. U. et al. Distinct Signaling of Coreceptors Regulates Specific Metabolism Pathways and Impacts Memory Development in CAR T Cells. *Immunity* 44, 380-390 (2016).
14. Zhao, Z. et al. Structural Design of Engineered Costimulation Determines Tumor Rejection Kinetics and Persistence of CAR T Cells. *Cancer Cell* 28, 415-428 (2015).
15. Bertram, E. M., Lau, P. & Watts, T. H. Temporal segregation of 4-1BB versus CD28-mediated costimulation: 4-1BB ligand influences T cell numbers late in the primary response and regulates the size of the T cell memory response following influenza infection. *J Immunol* 168, 3777-3785 (2002).
16. Vinay, D. S. & Kwon, B. S. Role of 4-1BB in immune responses. *Semin Immunol* 10, 481-489 (1998).
17. Weinberg, A. D., Vella, A. T. & Croft, M. OX-40: life beyond the effector T cell stage. *Semin Immunol* 10, 471-480 (1998).
18. Turtle, C. J. et al. Therapy of B Cell Malignancies with CD19-Specific Chimeric Antigen Receptor-Modified T Cells of Defined Subset Composition. *Blood* 124, 384-384 (2014).
19. Fedorov, V. D., Themeli, M. & Sadelain, M. PD-1- and CTLA-4-based inhibitory chimeric antigen receptors (iCARs) divert off-target immunotherapy responses. *Sci Transl Med* 5, 215ra172 (2013).

20. Morsut, L. et al. Engineering Customized Cell Sensing and Response Behaviors Using Synthetic Notch Receptors. *Cell* 164, 780-791 (2016).

21. Roybal, K. T. et al. Precision Tumor Recognition by T Cells With Combinatorial Antigen-Sensing Circuits. *Cell* 164, 770-779 (2016).

22. Hicklin, D. J., Marincola, F. M. & Ferrone, S. HLA class I antigen downregulation in human cancers: T-cell immunotherapy revives an old story. *Mol Med Today* 5, 178-186 (1999).

23. Waldhauer, I. & Steinle, A. NK cells and cancer immunosurveillance. *Oncogene* 27, 5932-5943 (2008).

24. Bourseau-Guilmain, E. et al. Hypoxia regulates global membrane protein endocytosis through caveolin-1 in cancer cells. *Nat Commun* 7, 11371 (2016).

25. Di Stasi, A. et al. Inducible apoptosis as a safety switch for adoptive cell therapy. *N Engl J Med* 365, 1673-1683 (2011).

26. Bonini, C. et al. HSV-TK gene transfer into donor lymphocytes for control of allogeneic graft-versus-leukemia. *Science* 276, 1719-1724 (1997).

27. Wu, C. Y., Roybal, K. T., Puchner, E. M., Onuffer, J. & Lim, W. A. Remote control of therapeutic T cells through a small molecule-gated chimeric receptor. *Science* 350, aab4077 (2015).

28. Juillerat, A. et al. Design of chimeric antigen receptors with integrated controllable transient functions. *Sci Rep* 6, 18950 (2016).

29. Vinson, C., Acharya, A. & Taparowsky, E. J. Deciphering B-ZIP transcription factor interactions in vitro and in vivo. *Biochim Biophys Acta* 1759, 4-12 (2006).

30. Moll, JR., Ruvinov, S. B., Pastan, I. & Vinson, C. Designed heterodimerizing leucine zippers with a ranger of pIs and stabilities up to 10(-15) M. *Protein Sci* 10, 649-655 (2001).

31. Bashor, C. J., Helman, N. C., Yan, S. & Lim, W. A. Using engineered scaffold interactions to reshape MAP kinase pathway signaling dynamics. *Science* 319, 1539-1543 (2008).

32. Siuti, P., Yazbek, J. & Lu, T. K. Synthetic circuits integrating logic and memory in living cells. *Nat Biotechnol* 31, 448-452 (2013).

33. Bonnet, J., Yin, P., Ortiz, M. E., Subsoontom, P. & Endy, D. Amplifying Genetic Logic Gates. *Science* (2013).

34. Auslander, S., Auslander, D., Muller, M., Wieland, M. & Fussenegger, M. Programmable single-cell mammalian biocomputers. *Nature* 487, 123-127 (2012).

35. Gaber, R. et al. Designable DNA-binding domains enable construction of logic circuits in mammalian cells. *Nat Chem Biol* 10, 203-208 (2014).

36. Cho, H. M. et al. Enhanced inhibition of murine tumor and human breast tumor xenografts using targeted delivery of an antibody-endostatin fusion protein. *Mol Cancer Ther* 4, 956-967 (2005).

37. Wu, X. et al. AXL kinase as a novel target for cancer therapy. *Oncotarget* 5, 9546-9563 (2014).

38. Schier, R. et al. Isolation of picomolar affinity anti-c-erbB-2 single-chain Fv by molecular evolution of the complementarity determining regions in the center of the antibody binding site. *J Mol Biol* 263, 551-567 (1996).

39. Stiffler, M. A. et al. PDZ domain binding selectivity is optimized across the mouse proteome. *Science* 317, 364-369 (2007).

40. Dueber, J. E., Mirsky, E. A. & Lim, W. A. Engineering synthetic signaling proteins with ultrasensitive input/output control. *Nature biotechnology* 25, 660-662 (2007).

41. Dueber, J. E., Yeh, B. J., Chak, K. & Lim, W. A. Reprogramming control of an allosteric signaling switch through modular recombination. *Science* 301, 1904-1908 (2003).

42. Khalil, A. S. et al. A synthetic biology framework for programming eukaryotic transcription functions. *Cell* 150, 647-658 (2012).

43. Reinke, A. W., Grant, R. A. & Keating, A. E. A synthetic coiled-coil interactome provides heterospecific modules for molecular engineering. *J Am Chem Soc* 132, 6025-6031 (2010).

44. Zhao, Y. et al. Multiple injections of electroporated autologous T cells expressing a chimeric antigen receptor mediate regression of human disseminated tumor. *Cancer Res* 70, 9053-9061 (2010).

45. Wilson, M. H., Coates, C. J. & George, A. L., Jr. PiggyBac transposon-mediated gene transfer in human cells. *Mol Ther* 15, 139-145 (2007).

46. Hackett, P. B., Largaespada, D. A. & Cooper, L. J. A transposon and transposase system for human application. *Mol Ther* 18, 674-683 (2010).

The technology described herein is further illustrated by the following examples which in no way should be construed as being further limiting.

Some embodiments of the technology described herein can be defined according to any of the following numbered paragraphs:

1. A composition comprising a multi-component chimeric antigen receptor (CAR); the multi-component CAR comprising:
   a. a first recognition polypeptide comprising 1) an antibody reagent specific for a first target ligand and 2) a protein interaction domain; and
   b. a signaling polypeptide comprising 1) an extracellular protein interaction domain that can bind specifically with the protein interaction domain of the first recognition polypeptide and 2) an intracellular T cell receptor (TCR) signaling domain.

2. The composition of paragraph 1, wherein the protein interaction domains are leucine zipper domains.

3. The composition of paragraph 2, wherein one leucine zipper domain is BZip (RR) and the second leucine zipper domain is AZip (EE).

4. The composition of paragraph 1, wherein the protein interaction domains are PSD95-Dlg1-zo-1 (PDZ) domains.

5. The composition of paragraph 1, wherein one protein interaction domain is streptavidin and a second protein interaction domain is streptavidin binding protein (SBP).

6. The composition of paragraph 1, wherein:
   a. one protein interaction domain is FKBP-binding domain of mTOR (FRB) and a second protein interaction domain is FK506 binding protein (FKBP);
   b. one protein interaction domain is cyclophilin-Fas fusion protein (CyP-Fas) and a second protein interaction domain is FK506 binding protein (FKBP);
   c. one protein interaction domain is calcineurinA (CNA) and a second protein interaction domain is FK506 binding protein (FKBP);
   d. one protein interaction domain is gibberellin insensitive (GIA) and a second protein interaction domain is gibberellin insensitive dwarf1 (GID1);
   e. one protein interaction domain is Snap-tag and a second protein interaction domain is Halo tag; or f. one protein interaction domain is T14-3-3-cdeltaC and a second protein interaction domain is C-Terminal peptides of PMA2 (CT52).

7. The composition of paragraph 1, wherein one protein interaction domain is PYL and a second protein interaction domain is ABI.

8. The composition of paragraph 1, wherein one protein interaction domain is a nucleotide tag and the second protein interaction domain is a zinc finger domain.

9. The composition of paragraph 8, wherein the protein interaction domain of the recognition polypeptide is a nucleotide tag and the extracellular protein interaction domain of the signaling polypeptide is a zinc finger domain.

10. The composition of any of paragraphs 8-9, wherein the nucleotide tag is a DNA tag.

11. The composition of any of paragraphs 8-10, wherein the DNA tag is a dsDNA tag.

12. The composition of any of paragraphs 1-11, further comprising a second recognition polypeptide comprising 1) an antibody reagent specific for a second target ligand and 2) a protein interaction domain that competes with the protein interaction domain of the signaling polypeptide for binding to the protein interaction domain of the first recognition polypeptide.

13. The composition of paragraph 12, wherein the protein interaction domain of the second recognition polypeptide and the protein interaction domain of the first recognition polypeptide have a greater affinity than the protein interaction domain of the signaling polypeptide and the protein interaction domain of the first recognition polypeptide.

14. The composition of any of paragraphs 12-13, wherein the target ligand recognized by the second recognition polypeptide is found on a healthy and/or non-target cell and not on a diseased and/or target cell.

15. The composition of any of paragraphs 1-11, further comprising a second recognition polypeptide comprising 1) an antibody reagent specific for a second target ligand and 2) a protein interaction domain; and wherein the signaling polypeptide further comprises a secondary protein interaction domain that specifically binds with the protein interaction domain of the second recognition polypeptide.

16. The composition of paragraph 15, wherein the affinity of the signaling polypeptide's secondary protein interaction domain and the protein interaction domain of the second recognition polypeptide is weaker than the affinity of the signaling polypeptide's first protein interaction domain and the protein interaction domain of the first recognition polypeptide.

17. The composition of any of paragraphs 15-16, wherein the first and second recognition polypeptides each comprise a secondary protein interaction domain; and wherein the secondary protein interaction domains specifically bind to each other.

18. A composition comprising a multi-component chimeric antigen receptor (CAR); the multi-component CAR comprising:
   a. a first recognition polypeptide comprising 1) an antibody reagent specific for a first target ligand and 2) a first portion of a nucleotide tag;
   b. a second recognition polypeptide comprising 1) an antibody reagent specific for a second target ligand and 2) a second portion of the nucleotide tag; and
   c. a signaling polypeptide comprising 1) an extracellular zinc finger domain that can bind specifically with a complete nucleotide tag formed by the association of the individual portions of the nucleotide tag and 2) an intracellular T cell receptor (TCR) signaling domain;
   wherein the individual portions of the nucleotide tag cannot be specifically bound by the zinc finger domain unless they are associated with each other.

19. The composition of paragraph 18, wherein the first portion of the nucleotide tag is a ssDNA and the second portion of the nucleotide tag is a complementary ssDNA.

20. The composition of paragraph 18-19, further comprising a third recognition polypeptide encoding 1) an antibody reagent specific for a third target ligand and 2) a third portion of the nucleotide tag;
   wherein the individual portions or pairwise combinations individual portions of the nucleotide tag cannot be specifically bound by the zinc finger domain, but when all three portions are associated with each other, the resulting complex can be specifically bound by the zinc finger domain.

21. The composition of paragraph 20, wherein 1) the first portion of the nucleotide tag is a ssDNA; and 2) the second and third portions of the nucleotide tag are ssDNAs, each of which is complementary to the first portion and 3) the second and third portions of the nucleotide tag have sequences that do not overlap with each other.

22. A composition comprising a multi-component chimeric antigen receptor (CAR); the multi-component CAR comprising:
   a. a first recognition polypeptide comprising 1) an antibody reagent specific for a first target ligand and 2) a first nucleotide tag;
   b. a second recognition polypeptide comprising 1) an antibody reagent specific for a second target ligand and 2) a second nucleotide tag; and
   c. a signaling polypeptide comprising 1) an extracellular zinc finger domain that can bind specifically with the first nucleotide tag and 2) an intracellular T cell receptor (TCR) signaling domain;
   wherein the nucleotide tags cannot be specifically bound by the zinc finger domain when they are associated with each other.

23. The composition of paragraph 22, wherein the first nucleotide tag forms a hairpin-loop structure and wherein the second nucleotide tag is complementary to a portion of the first nucleotide tag that encompasses a portion of one leg of the hairpin-loop and a portion of the loop of the hairpin-loop.

24. The composition of any of paragraphs 22-23, wherein the second target ligand is found on a healthy and/or non-target cell and not on a diseased and/or target cell.

25. The composition of any of paragraphs 1-24, wherein a target ligand is a ligand found on a diseased and/or target cell.

26. The composition of any of paragraphs 1-24, wherein the target ligand specifically bound by a recognition polypeptide that can specifically bind with a signaling polypeptide is a ligand found on a diseased and/or target cell.

27. The composition of any of paragraphs 1-26, wherein the target ligand specifically bound by a recognition polypeptide that can specifically bind with a signaling polypeptide is a ligand found on a diseased and/or target cell and not on a healthy and/or non-target cell.

28. The composition of any of paragraphs 1-27, wherein the diseased cell is a cancerous cell.

29. The composition of any of paragraphs 1-28, wherein the antibody reagent is selected from the group consisting of:

an immunoglobulin molecule, a monoclonal antibody, a chimeric antibody, a CDR-grafted antibody, a human antibody, a humanized antibody, a Fab, a Fab', a F(ab')2, a Fv, a disulfide linked Fv, a scFv, a single domain antibody, a diabody, a multispecific antibody, a dual specific antibody, an anti-idiotypic antibody, and a bispecific antibody.

30. The composition of any of paragraphs 1-29, wherein the intracellular TCR signaling domain is a signaling domain from a protein selected from the group consisting of: TCRζ, FcRγ, FcRβ, CD3γ, CD3δ, CD3ε, CD3ζ, CD22, CD79a, CD79b, CD66d, CARD11, CD2, CD7, CD27, CD28, CD30, CD40, CD54 (ICAM), CD83, CD134 (OX40), CD137 (4-1BB), CD150 (SLAMF1), CD152 (CTLA4), CD223 (LAG3), CD270 (HVEM), CD273 (PD-L2), CD274 (PD-L1), CD278 (ICOS), DAP10, LAT, NKD2C SLP76, TRIM, ZAP70, and 41BB.

31. The composition of any of paragraphs 1-30, further comprising second multi-component CAR according to any of paragraphs 1-30.

32. The composition of paragraph 31, wherein the antibody reagents of second multi-component CAR bind specifically to different target ligands than those bound by the antibody reagents of the first multi-component CAR.

33. The composition of any of paragraphs 30-32, wherein the intracellular T cell receptor (TCR) signaling domain of the second multi-component CAR inhibits T cell activity.

34. The composition of paragraph 33, wherein the intracellular T cell receptor (TCR) signaling domain of the second multi-component CAR which inhibits T cell activity comprises a signaling domain of a polypeptide selected from the group consisting of: PD1; CTLA4; BTLA; KIR; LAG-3; TIM-3; A2aR; LAIR-1; and TGIT.

35. The composition of any of paragraphs 33-34, wherein the target ligand specifically bound by a recognition polypeptide that can specifically bind with the signaling polypeptide of the second multi-component CAR is a ligand found on a healthy and/or non-target cell.

36. The composition of any of paragraphs 33-34, wherein the target ligand specifically bound by a recognition polypeptide that can specifically bind with the signaling polypeptide of the second multi-component CAR is a ligand found on a healthy and/or non-target cell and not on a diseased and/or target cell.

37. The composition of any of paragraphs 1-36, wherein the signaling polypeptide is present on the membrane of a cell.

38. The composition of paragraph 37, wherein the one or more recognition polypeptides are present in the extracellular space.

39. An engineered cell expressing the composition of any of paragraphs 1-38.

40. The cell or composition of any of paragraphs 1-39, wherein the cell is a T cell, NK cell, or NKT cell.

41. The cell or composition of any of paragraphs 1-40, wherein the cell is a T cell.

42. A method of killing a target cell, the method comprising contacting the cell with a composition or cells of any of paragraphs 1-41.

43. A method of treating a disease, comprising administering a composition or cells of any of paragraphs 1-41 to a subject in need of treatment thereof.

44. The method of paragraph 42, wherein the disease is selected from the group consisting of:

cancer; solid cancers; breast cancer; lung cancer; acute lymphoblastic leukemia; multiple myeloma; and refractory multiple myeloma.

45. A method of treating cancer, comprising administering a composition or cells of any of paragraphs 1-41 to a subject in need of treatment thereof.

46. The method of paragraph 45, wherein the cell is autologous to the subject.

47. The method of paragraph 46, wherein the administered cell is derived and/or descended from a cell obtained from the subject and has been modified ex vivo to comprise the at least one multi-component CAR.

48. An engineered cell comprising a multi-component chimeric antigen receptor (CAR) signaling polypeptide, the signaling polypeptide comprising 1) an extracellular protein interaction domain and 2) an intracellular T cell receptor (TCR) signaling domain.

49. The cell of paragraph 48, wherein the protein interaction domain is a leucine zipper domain.

50. The cell of paragraph 49, wherein the leucine zipper domain is BZip (RR) or AZip (EE).

51. The cell of paragraph 48, wherein the protein interaction domain is a PSD95-Dlg1-zo-1 (PDZ) domain.

52. The cell of paragraph 48, wherein the protein interaction domain is streptavidin or streptavidin binding protein (SBP).

53. The cell of paragraph 48, wherein the protein interaction domain is FKBP-binding domain of mTOR (FRB) or FK506 binding protein (FKBP).

54. The cell of paragraph 48, wherein the protein interaction domain is PYL or ABI.

55. The cell of paragraph 48, wherein the protein interaction domain is a nucleotide tag or a zinc finger domain.

56. The cell of paragraph 55, wherein the nucleotide tag is a DNA tag.

57. The cell of paragraph 56, wherein the DNA tag is a dsDNA tag.

58. The cell of paragraph 55, wherein the protein interaction domain is a zinc finger domain.

59. The cell of any of paragraphs 48-58, wherein the signaling polypeptide is present on the membrane of the cell.

60. The cell of any of paragraphs 48-59, wherein the cell is a T cell, NK cell, or NKT cell.

61. The cell of any of paragraphs 48-60, wherein the cell is a T cell.

62. The cell of any of paragraphs 48-61, wherein the intracellular TCR signaling domain is a signaling domain from a protein selected from the group consisting of:

TCRζ, FcRγ, FcRβ, CD3γ, CD3δ, CD3ε, CD3ζ, CD22, CD79a, CD79b, CD66d, CARD11, CD2, CD7, CD27, CD28, CD30, CD40, CD54 (ICAM), CD83, CD134 (OX40), CD137 (4-1BB), CD150 (SLAMF1), CD152 (CTLA4), CD223 (LAG3), CD270 (HVEM), CD273 (PD-L2), CD274 (PD-L1),

CD278 (ICOS), DAP10, LAT, NKD2C SLP76, TRIM, ZAP70, and 41BB.

63. The cell of any of paragraphs 48-62, wherein the signaling polypeptide further comprises a secondary protein interaction domain that specifically binds with the protein interaction domain of the second recognition polypeptide.

64. The cell of any of paragraphs 48-62, further comprising a second multi-component CAR signaling peptide according to any of paragraphs 48-62.

65. A method of treating a disease, the method comprising administering:
   a cell of any of paragraphs 48-64; and
   a first recognition polypeptide comprising 1) an antibody reagent specific for a first target ligand and 2) a protein interaction domain that can bind specifically with the protein interaction domain of the signaling polypeptide;
   to a subject in need of treatment therefor.

66. The method of paragraph 65, wherein the antibody reagent is selected from the group consisting of:
   an immunoglobulin molecule, a monoclonal antibody, a chimeric antibody, a CDR-grafted antibody, a human antibody, a humanized antibody, a Fab, a Fab', a F(ab')2, a Fv, a disulfide linked Fv, a scFv, a single domain antibody, a diabody, a multispecific antibody, a dual specific antibody, an anti-idiotypic antibody, and a bispecific antibody.

67. The method of any of paragraphs 65-66, wherein the cell is autologous to the subject.

68. The method of any of paragraphs 65-67, wherein the administered cell is derived and/or descended from a cell obtained from the subject and has been modified ex vivo to comprise the at least one multi-component CAR.

69. The method of any of paragraphs 65-68, wherein the protein interaction domains are leucine zipper domains.

70. The method of paragraph 69, wherein one leucine zipper domain is BZip (RR) and the second leucine zipper domain is AZip (EE).

71. The method of any of paragraphs 65-68, wherein the protein interaction domains are PSD95-Dlg1-zo-1 (PDZ) domains.

72. The method of any of paragraphs 65-68, wherein one protein interaction domain is streptavidin and a second protein interaction domain is streptavidin binding protein (SBP).

73. The method of any of paragraphs 65-68, wherein:
   a. one protein interaction domain is FKBP-binding domain of mTOR (FRB) and a second protein interaction domain is FK506 binding protein (FKBP);
   b. one protein interaction domain is cyclophilin-Fas fusion protein (CyP-Fas) and a second protein interaction domain is FK506 binding protein (FKBP);
   c. one protein interaction domain is calcineurinA (CNA) and a second protein interaction domain is FK506 binding protein (FKBP);
   d. one protein interaction domain is gibberellin insensitive (GIA) and a second protein interaction domain is gibberellin insensitive dwarf1 (GID1);
   e. one protein interaction domain is Snap-tag and a second protein interaction domain is Halo tag; or
   f. one protein interaction domain is T14-3-3-cdeltaC and a second protein interaction domain is C-Terminal peptides of PMA2 (CT52).

74. The method of paragraph 74, wherein:
   a. when one protein interaction domain is FKBP-binding domain of mTOR (FRB) and a second protein interaction domain is FK506 binding protein (FKBP), the method further comprises administering tacrolimus, a rapalog, or everolimus;
   b. when one protein interaction domain is cyclophilin-Fas fusion protein (CyP-Fas) and a second protein interaction domain is FK506 binding protein (FKBP), the method further comprises administering FKCsA;
   c. when one protein interaction domain is calcineurinA (CNA) and a second protein interaction domain is FK506 binding protein (FKBP), the method further comprises administering FK506;
   d. one protein interaction domain is gibberellin insensitive (GIA) and a second protein interaction domain is gibberellin insensitive dwarf1 (GID1), the method further comprises administering gibberellin;
   e. when one protein interaction domain is Snap-tag and a second protein interaction domain is Halo tag, the method further comprises administering HaXS; or
   f. when one protein interaction domain is T14-3-3-cdeltaC and a second protein interaction domain is C-Terminal peptides of PMA2 (CT52), the method further comprises administering fusicoccin.

75. The method of any of paragraphs 65-68, wherein one protein interaction domain is PYL and a second protein interaction domain is ABI.

76. The method of any of paragraphs 65-68, wherein the protein interaction domain of the recognition polypeptide is a nucleotide tag and the extracellular protein interaction domain of the signaling polypeptide is a zinc finger domain.

77. The method of paragraph 76, wherein the nucleotide tag is a DNA tag.

78. The method of paragraph 77, wherein the DNA tag is a dsDNA tag.

79. The method of any paragraphs 65-78, further comprising administering a second recognition polypeptide comprising 1) an antibody reagent specific for a second target ligand and 2) a protein interaction domain that competes with the protein interaction domain of the signaling polypeptide for binding to the protein interaction domain of the first recognition polypeptide.

80. The method of paragraph 79, wherein the protein interaction domain of the second recognition polypeptide and the protein interaction domain of the first recognition polypeptide have a greater affinity than the protein interaction domain of the signaling polypeptide and the protein interaction domain of the first recognition polypeptide.

81. The method of any of paragraphs 79-80, wherein the target ligand recognized by the second recognition polypeptide is found on a healthy and/or non-target cell and not on a diseased and/or target cell.

82. The method of any of paragraphs 65-78, further comprising administering a second recognition polypeptide comprising 1) an antibody reagent specific for a second target ligand and 2) a protein interaction domain; and wherein the signaling polypeptide further comprises a secondary protein interaction domain that specifically binds with the protein interaction domain of the second recognition polypeptide.

83. The method of paragraph 82, wherein the affinity of the signaling polypeptide's secondary protein interaction domain and the protein interaction domain of the second recognition polypeptide is weaker than the affinity of the signaling polypeptide's first protein interaction domain and the protein interaction domain of the first recognition polypeptide.

84. The method of any of paragraphs 82-83, wherein the first and second recognition polypeptides each comprise a secondary protein interaction domain; and wherein the secondary protein interaction domains specifically bind to each other.

85. The method of any of paragraphs 65-78, further comprising administering:

a. a first recognition polypeptide comprising 1) an antibody reagent specific for a first target ligand and 2) a first portion of a nucleotide tag;

b. a second recognition polypeptide comprising 1) an antibody reagent specific for a second target ligand and 2) a second portion of the nucleotide tag;

wherein the signaling polypeptide comprises 1) an extracellular zinc finger domain that can bind specifically with a complete nucleotide tag formed by the association of the individual portions of the nucleotide tag; and wherein the individual portions of the nucleotide tag cannot be specifically bound by the zinc finger domain unless they are associated with each other.

86. The method of paragraph 85, wherein the first portion of the nucleotide tag is a ssDNA and the second portion of the nucleotide tag is a complementary ssDNA.

87. The method of any of paragraphs 85-86, further comprising administering a third recognition polypeptide encoding 1) an antibody reagent specific for a third target ligand and 2) a third portion of the nucleotide tag;

wherein the individual portions or pairwise combinations individual portions of the nucleotide tag cannot be specifically bound by the zinc finger domain, but when all three portions are associated with each other, the resulting complex can be specifically bound by the zinc finger domain.

88. The method of paragraph 87, wherein 1) the first portion of the nucleotide tag is a ssDNA; and 2) the second and third portions of the nucleotide tag are ssDNAs, each of which is complementary to the first portion and 3) the second and third portions of the nucleotide tag have sequences that do not overlap with each other.

89. A method of any of paragraphs 65-78, comprising administering:

a. a first recognition polypeptide comprising 1) an antibody reagent specific for a first target ligand and 2) a first nucleotide tag;

b. a second recognition polypeptide comprising 1) an antibody reagent specific for a second target ligand and 2) a second nucleotide tag;

wherein the signaling polypeptide comprises 1) an extracellular zinc finger domain that can bind specifically with the first nucleotide tag; and wherein the nucleotide tags cannot be specifically bound by the zinc finger domain when they are associated with each other.

90. The method of paragraph 89, wherein the first nucleotide tag forms a hairpin-loop structure and wherein the second nucleotide tag is complementary to a portion of the first nucleotide tag that encompasses a portion of one leg of the hairpin-loop and a portion of the loop of the hairpin-loop.

91. The method of any of paragraphs 89-90, wherein the second target ligand is found on a healthy and/or non-target cell and not on a diseased and/or target cell.

92. The method of any of paragraphs 65-91, wherein a target ligand is a ligand found on a diseased and/or target cell.

93. The method of any of paragraphs 65-92, wherein the target ligand specifically bound by a recognition polypeptide that can specifically bind with a signaling polypeptide is a ligand found on a diseased and/or target cell.

94. The method of any of paragraphs 65-93, wherein the target ligand specifically bound by a recognition polypeptide that can specifically bind with a signaling polypeptide is a ligand found on a diseased and/or target cell and not on a healthy and/or non-target cell.

95. The method of any of paragraphs 65-94, wherein the diseased cell is a cancerous cell.

96. The method of any of paragraphs 65-95, wherein the cell is a cell of paragraph 64 and the subject is further administered a second recognition polypeptide comprising 1) an antibody reagent specific for a second target ligand and 2) a protein interaction domain that can bind specifically with the protein interaction domain of the second signaling polypeptide.

97. The method of paragraph 96, wherein the intracellular T cell receptor (TCR) signaling domain of the second multi-component CAR signaling polypeptide inhibits T cell activity.

98. The method of paragraph 96, wherein the target ligand specifically bound by a recognition polypeptide that can specifically bind with the second signaling polypeptide is a ligand found on a healthy and/or non-target cell.

99. The method of any of paragraphs 96-98, wherein the target ligand specifically bound by a recognition polypeptide that can specifically bind with the second signaling polypeptide is a ligand found on a healthy and/or non-target cell and not on a diseased and/or target cell.

EXAMPLES

Example 1

Adoptive T cell therapy is becoming a paradigm shifting technology for cancer therapy. The transfer of chimeric antigen receptor (CAR)-expressing T cells to patients has demonstrated phenomenal success in clinical trials against B cell malignancies, and led to some major commercial investment transactions in recent years. Although promising, cancer specificity remains a major limitation because of its reliance on identifying a single tumor associated biomarker. Existing CAR systems can only integrate two antigens and have no capacity for further enhancement. Provided herein is a novel CAR platform (referred to herein as multicomponent CARs or SMART CARs) that can sense a large number of cancer targets, perform complex logic computation, and execute cancer cells killing.

Furthermore, the CARs described herein are designed to be modular such that new targets can be accommodated in vivo without further genetic manipulation of patient's T cells. This highly modular design affords unrivaled specificity and flexibility, with transformative impact on cell-based therapy for cancers. The technology described herein makes adoptive T-cell therapy more powerful by making it tunable to a patient's own needs. Therapy with existing CARs is viable for a select group of patients due to the difficulty in making changes to the therapy once it has been applied. Therapy with the multi-component CARs described herein permits a means to change the activity of the therapy at bedside, providing doctors a simple and effective means to control adoptive T-cell therapy.

The transfer of chimeric antigen receptor (CAR)-expressing T cells to patients is a promising approach for cancer immunotherapy. This therapeutic approach is based on the genetic reprogramming of T cells with a synthetic immune receptor that directs them to destroy malignant cells. A CAR typically is consisted of a single-chain variable fragment (scFv) antibody as the extracellular antigen-recognition domain, and signaling cytoplasmic domains to trigger the T cell activation (FIG. 1A). CAR expressing T cells targeted to CD19 have been successfully shown to cure leukemia in clinical trials, where up to 92% of patients entered into durable complete remission after the treatment. Although promising, this technology also has drawbacks. Fatal events have emerged from clinical trials in which CAR-bearing T-cells responded to normal host tissue expressing low levels of the targeted tumor antigens. A reason to why the anti-CD19 CAR is more successful than other CARs is because the off-target effect for CD19 CAR is expected and manageable. CD19 expression is restricted mostly to B cells. Although T cells expressing CD19 CAR will destroy both healthy and malignant B cells, long-term B cells deficiency is manageable with immunoglobulin replacement therapy.

Unfortunately, this is not the case for most other tumors, where the cancer antigen is only found in a very restricted set of tissues. To combat the dangerous off-target issues, a combinatorial receptors approach has been developed where two different antigen recognition antibodies are fused to TCR and co-stimulatory domains separately such that only tumors with both antigens will trigger the full T cell activation program. However, this approach only allows two antigens to be recognized simultaneously, thus severely constrains the potential of this approach.

The CAR platform described herein, also referred to herein as SMART CAR, allows a T cell to detect cancer cells using multiple biomarkers, and perform complex combinatorial logic computation based on these markers. This computation capability is almost impossible to achieve in any other forms of therapeutic agents (e.g. biologics and small molecules) and will enable extremely high tumor specificity.

Notably, existing CAR technologies rely on finding a single biomarker or "magic bullet" that specifically distinguishes cancer from healthy cells, which has proven to be extremely challenging. In fact, a major bottleneck for adoption for the CAR technology to other cancers is finding the proper targets. The technology described herein greatly increases the number of targetable cancer antigens, thus transforming the adoptive immunotherapy field.

A chimeric antigen receptor is a fusion of cancer antigen-specific single-chain antibodies with intracellular signaling domains from the T cell receptor (TCR) and/or other co-stimulatory pathways. Existing CAR technologies rely solely on the recognition of one antigen by a single-chain antibody, which constrains their specificity. Specificity can be greatly improved if more cancer antigen can be detected simultaneously. The technology described herein permits recognition of multiple antigens. Moreover, antigens that help identify normal tissues can also be detected by the T cells described herein, such that the presence of these antigens on healthy cells inhibits T cell activation. Therefore, the technology described herein, which can detect antigens from both cancer and normal cells and perform complex combinatorial logic computation greatly improves specificity.

Described herein are multi-component CARs that utilize programmable interaction to perform molecular computation. In some embodiments, leucine zipper, which is a protein domain that can form heteromeric structures through charge interactions, is used in the present receptor design. In this new CAR design, a leucine zipper replaces the extracellular domains on CARs and the cognate leucine zipper is fused to the antibody. When the cognate leucine zippers are bound to each other, they can activate the signaling activity of the CAR. Leucine zipper domains can also be engineered to compete with each other for the same binding partner, thus allowing inhibition and "OFF" functionality. Moreover, multiple orthogonal pairs permit control of different signaling domains (e.g. PD-1, CTLA-4) independently. Also, different affinities between leucine zipper pairs permit engineering of complex functions. For example, the strength of output signal of zipCAR can be tuned and weak interactions between leucine zipper pairs permits the use of cooperative behavior, allowing "AND" functionality.

For example, two jurkat cell lines were transduced with two different lentivirus vectors. One jurkat cell line expressed zipCAR with signaling domain (CD3 zeta) fused to mCherry. The other jurkat cell lines expressed zipCAR with cognate leucine zipper and did not have a signaling domain (CD3 zeta) nor were they fused to mCherry. It was observed that Jurkat T cells expressing zipCAR with signaling domain were able to activate and initiate signaling pathway by interacting with cells expressing cognate zipCAR. This demonstrates the functionality of zipCAR in primary T cells (data not shown).

In a further example, antibodies which contain single chain variable fragment (scFv) targeting HER2 connected to a leucine zipper that can bind to zipCARs were purified. It was verified that zipCARs can be activated by purified antibodies in primary CD4+ T cells (measured secreted cytokines) as well as in Jurkat cell lines (measured NFAT promoter activity) (data not shown).

Moreover, described herein are several orthogonal pairs of leucine zipper pairs that can be used to control different signaling domains (e.g. co-stimulatory, co-inhibitory signaling domains).

In contrast to existing technologies that use antibodies, streptaviding, or CD16 as the extracellular domain, the present use of leucine zippers permits sophisticated molecular computation.

Many leucine-zipper domains can be chosen to allow sensing of multiple inputs. The signaling domains can also be manipulated and/or selected such that different pathway can be controlled. Furthermore, variation in the affinity of leucine zipper interactions permits control of the activation strength. Lastly, it is contemplated herein that any protein-protein interaction domain can replace the leucine zipper domain such as PDZ domains, SBP(Streptavidin Biding Protein)-Streptavidin, or drug inducible FKBP-FRB pairs or PYL-ABI pairs.

Example 2

In some embodiments, the multi-component CARs described herein utilize zinc-finger protein as the extracellular portion of the CAR (zfCAR) and various signaling proteins as the intracellular communication domains. Furthermore, zinc-finger proteins can be engineered to bind to predefined double stranded DNA sequence with high affinity and specificity. An antibody can be labeled with any DNA sequences. Together, when the antibody binds to the antigen, the zfCAR will bind to the DNA and trigger T cell activation. Such a split system is very flexible because the zfCAR does not need to be redesigned for different antigens. Additionally, the technology described herein can perform complex molecular computation that cannot be duplicated by existing systems. For instance, different antibodies can be conjugated with different complementary single stranded DNA sequence where only in the presence of all the antibodies will the proper double stranded DNA be formed, which is required for the binding to zinc finger. This configuration represents a multi-input AND gate. By using just three antibodies, the systems described herein will already surpass the most antigen recognitions (2) ever demonstrated by CARs. Furthermore, a DNA sequence can be made to disrupt double stranded DNA that binds to a zinc-finger domain, thus forming NOT gates. These interruptive DNA sequences can be attached to an antibody that binds to normal cells, thus preventing T cells from attacking healthy tissues. Together, highly sophisticated logic computation can be achieved for the first time in CAR-based therapy.

Another unique feature of the zfCAR is that zinc-finger proteins can be readily designed to bind to different DNA sequences. As such, multiple orthogonal zfCAR can be engineered with different intracellular signaling domains that activate distinct signaling pathways. There are at least two advantages of this design. 1) It allows more antigens to be detected and integrated into the overall T cell response. 2) Different signaling pathways can be controlled independently, thus providing a highly customized method of tuning T cell response. Inhibitory signaling pathways can also be used, therefore providing an "OFF" switch that can further improve safety and specificity. By merging three emerging fields of bioscience, DNA nanotechnology, synthetic biology, and adoptive immunotherapy, provided herein is a groundbreaking receptor technology that promises to greatly improve cancer therapy.

Multiple zinc-finger domains can be utilized to permit sensing of multiple inputs. The signaling domains can be varied such that different pathway can be controlled. Additionally, the zinc-finger affinity to DNA can be varied to control the activation strength. In some embodiments, the zinc finger domain can be substituted for with another protein-protein interaction domain.

Example 3: a Split, Universal, Programmable, and Reconfigurable (SUPRA) CAR Platform Described herein is the improvement of the specificity and safety of CAR-based therapy, via development of a CAR platform that can perform multiplexed antigens targeting, perform logic computation, and execute cancer cells killing. In the exemplary embodiment described herein, heterodimeric leucine zipper proteins were utilized as the extracellular domain to TCR intracellular signaling domains to generate universal receptors. The receptors can be activated by a fusion protein consisted of a single chain antibody and a cognate leucine zipper domain. The antibody-zipper fusion serves as an adaptor between antigens and engineered T cells. The antibodies provide antigen specificity and the identity of the leucine zipper dictates which receptor to activate. This CAR platform allows the engineered T cells to target new targets in vivo without further genetic manipulation of the T cells. This modular design affords specificity, flexibility, and programmability.

The transfer of chimeric antigen receptor (CAR)-expressing T cells to patients is a promising approach for cancer immunotherapy[1,2]. This therapeutic approach is based on the genetic reprogramming of T cells with a synthetic immune receptor that directs them to destroy malignant cells. A CAR typically is consisted of a single-chain variable fragment (scFv) antibody as the extracellular antigen-recognition domain, and cytoplasmic signaling domains to trigger the T cell activation (FIG. 1A). CAR expressing T cells targeted to CD19 have been successfully shown to cure leukemia in clinical trials, where up to 90% of patients entered into durable complete remission after the treatment-. Although promising, this technology also has its drawbacks. Fatal events had emerged from clinical trials in which CAR-bearing T-cells responded to normal host tissue expressing low levels of the targeted tumor antigens[3]. A reason to why the anti-CD19 CAR is more successful than other CARs is that the off-target effect for CD19 CAR is expected and manageable. CD19 expression is restricted mostly to B cells. Although T cells expressing CD19 CAR will destroy both healthy and malignant B cells, long-term B cells deficiency is manageable with immunoglobulin replacement therapy. Unfortunately, this is not the case for most other tumors, where the cancer antigen is only found in a very restricted set of tissues.

Figure 1B:
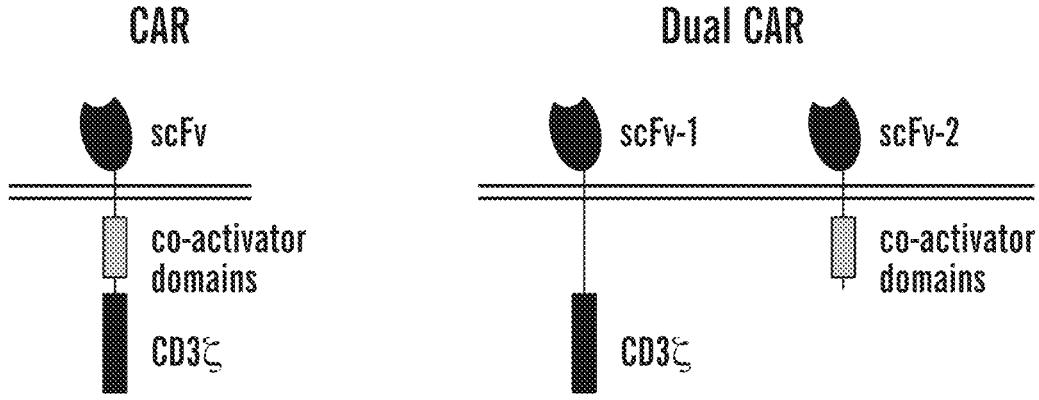
Figure 1B:
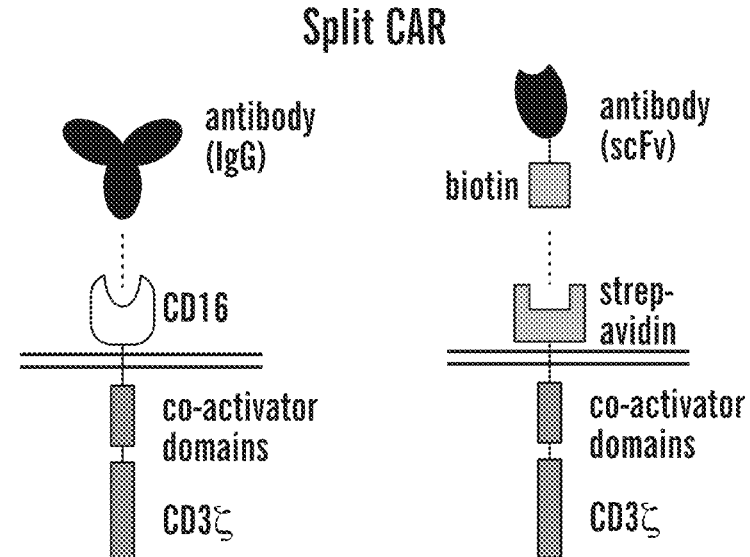

To combat the dangerous off-target issue, combinatorial receptors approach has been developed where two different antigen recognition antibodies are fused to TCR and co-stimulatory domains separately such that only tumors with both antigens will trigger the full T cell activation program[4,5](FIG. 1B). However, this approach only allows two antigens to be recognized simultaneously, and thus severely constrains the potential of this approach. Moreover, others had shown that two scFvs with different antigen specificities could be fused together into one CAR, thus allowing either one of the two antigens to trigger T cell activations. This system recapitulates an OR logic and can reduce the chance of tumor escape because mutations to two antigens are needed. At this moment, however, this tandem antibody CAR design can only perform OR logic. Specificity can be greatly improved if more cancer antigen can be detected simultaneously. Moreover, antigens that identify normal tissues should also be detected by the T cells such that the presence of these antigens on healthy cells inhibits T cell activation. Therefore, a strategy that can accommodate multiple inputs and perform complex logic would be desirable.

Another challenge of using the "fixed" CAR design is that if different antigens are to be targeted by the engineered T cells, a new set of receptors has to be created and the patient's T cells needs to be modified again with the new receptors.

As such, a split or universal CAR design is being explored where the CAR is split into two portions, a receptor portion and an antibody portion. The receptor portion is expressed on the cell surface with a recruitment domain. This receptor is not able to recognize antigen. The antibody portion is modified with a ligand or a cognate binding domain that the receptor on the cell can recognize. The antibody will bind to the cancer cell, and the ligand on the antibody will recruit and active the T cells expressing the corresponding receptor. The split CAR configuration allows a large panel of antigens to be targeted without reengineering the receptor and immune cells. Two different strategies are available for recruiting antigen recognition motif to the signaling motif on the T cells, and they served as the inspiration for this project (FIG. 1b). The simplest version of a split CAR design is accomplished with the fusion of CD16 extracellular domain and intracellular TCR signaling domains[7]. CD16 is a low affinity Fc receptor that binds to the constant region of monoclonal antibody. Therefore, many monoclonal antibodies that were produced by pharmaceutical companies can be used for adoptive immunotherapy without modification. Although convenient, this CD16 CAR can have many potential off-target effects through binding to endogenous antibody produced by patients.

Figure 2A:
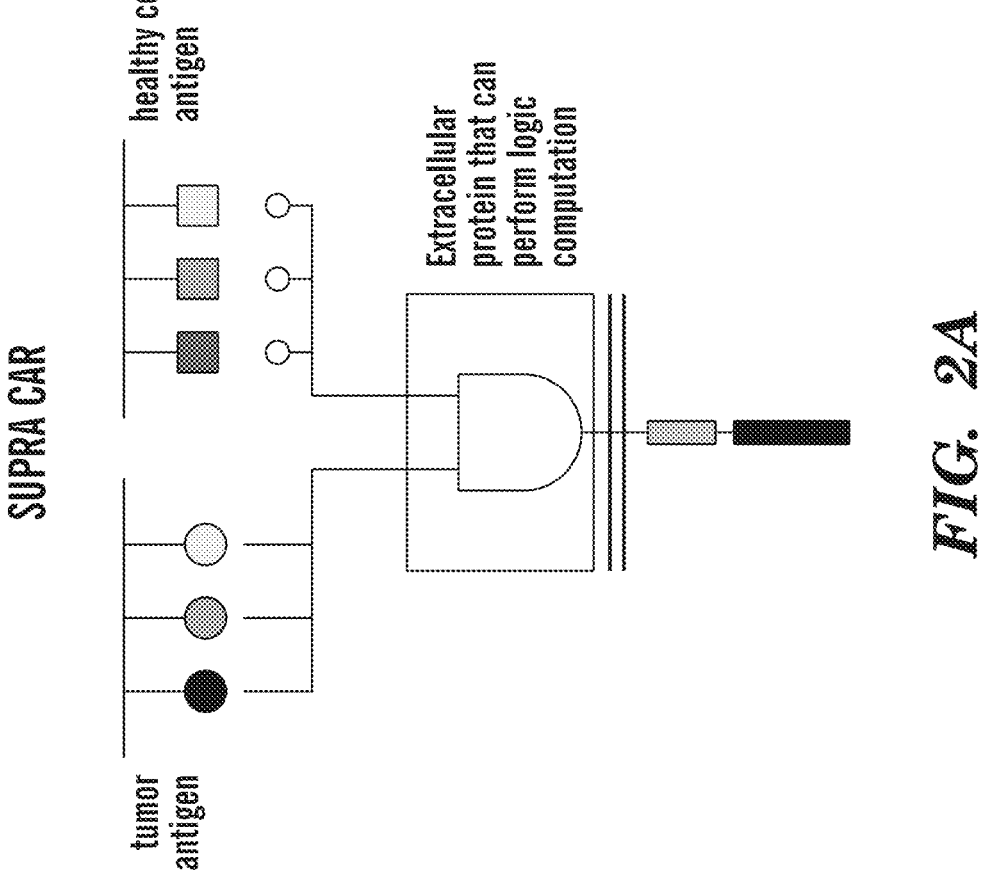
FIGS. 2A-2B depict schematics of the SUPRA CAR platform design.
Figure 2B:
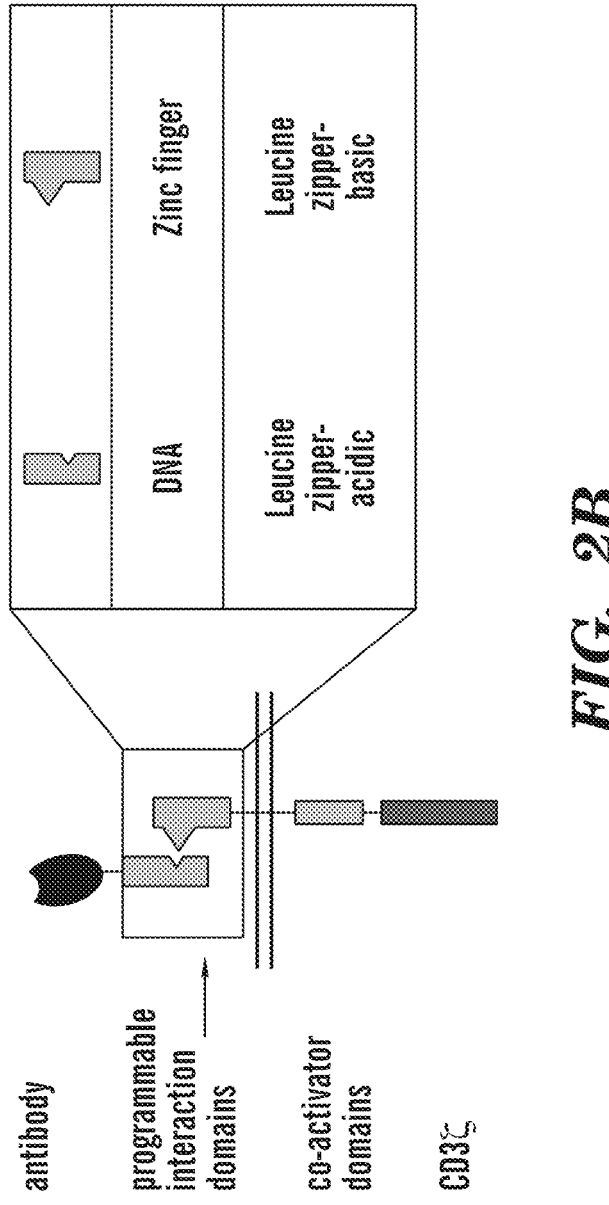
Figure 3A:
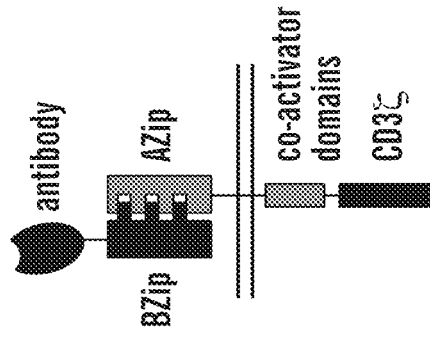
Figure 3A:
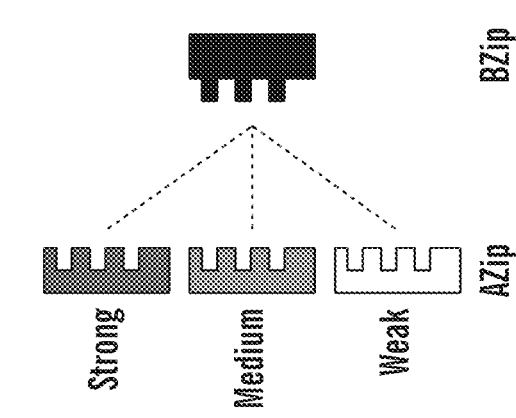
Figure 3A:
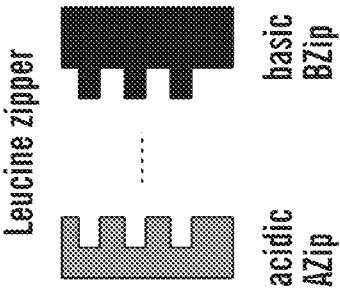
Figure 3B:
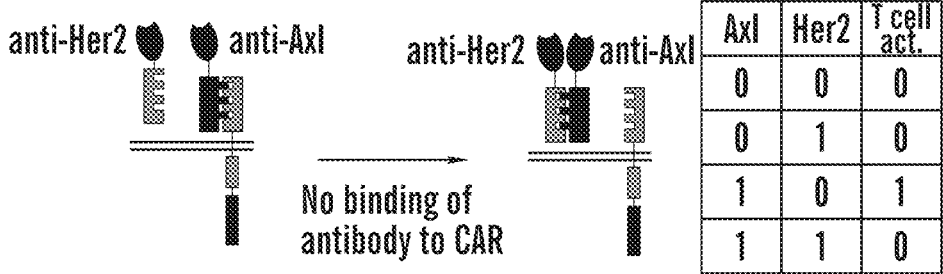
Figure 3B:
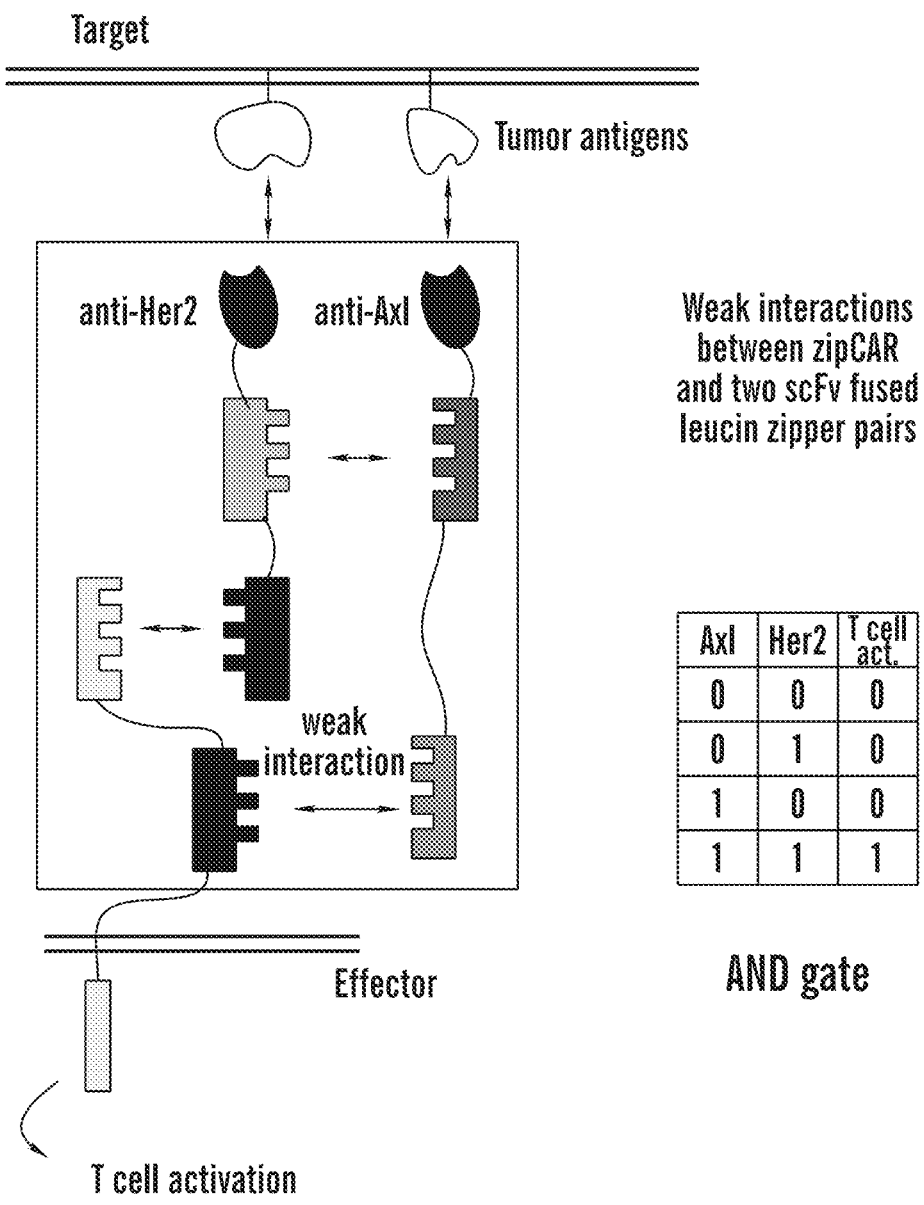
Figure 3C:
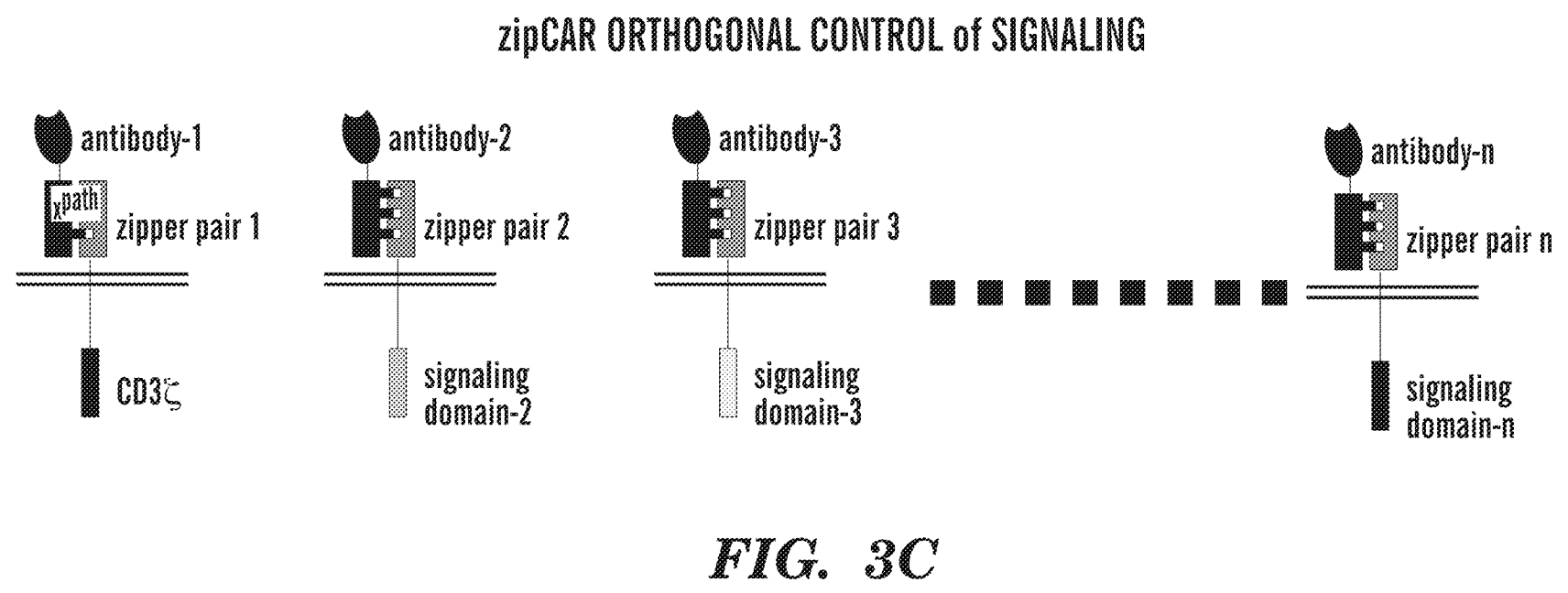

To address the antigen specificity limitation in adoptive immunotherapy, developed herein is a developed a Split, Universal, Programmable, and ReconfigurAble (SUPRA) CAR platform (FIG. 2A). The SUPRA platform uses programmable biomolecular interaction domains as the extracellular portion of the CAR and various signaling proteins as the intracellular domains (FIG. 2B). In particular, leucine zipper, a protein domain that can form heteromeric structures through charge interactions, was used in the receptor design. In this new CAR design, a leucine zipper replaces the extracellular domains on CARs and the cognate leucine zipper is be fused to the antibody (FIG. 3A). Leucine zippers are good candidates for the SUPRA platform because many orthogonal pairs of leucine zipper are available, thus providing a large pool of candidates for our design effort. Leucine zipper domains can also be engineered to compete with each other for the same binding partner, thus allowing inhibition and "OFF" functionality (FIG. 3B). Moreover, weak interactions between leucine zipper fused to scFv and zipCAR permits AND gate functionality to perform multiplexed antigens targeting. In addition, different affinities between leucine zipper pairs permit engineering of complex functions. Moreover, multiple orthogonal pairs permit control of different signaling domains (e.g. PD-1, CTLA-4) independently (FIG. 3C).

Figure 4:
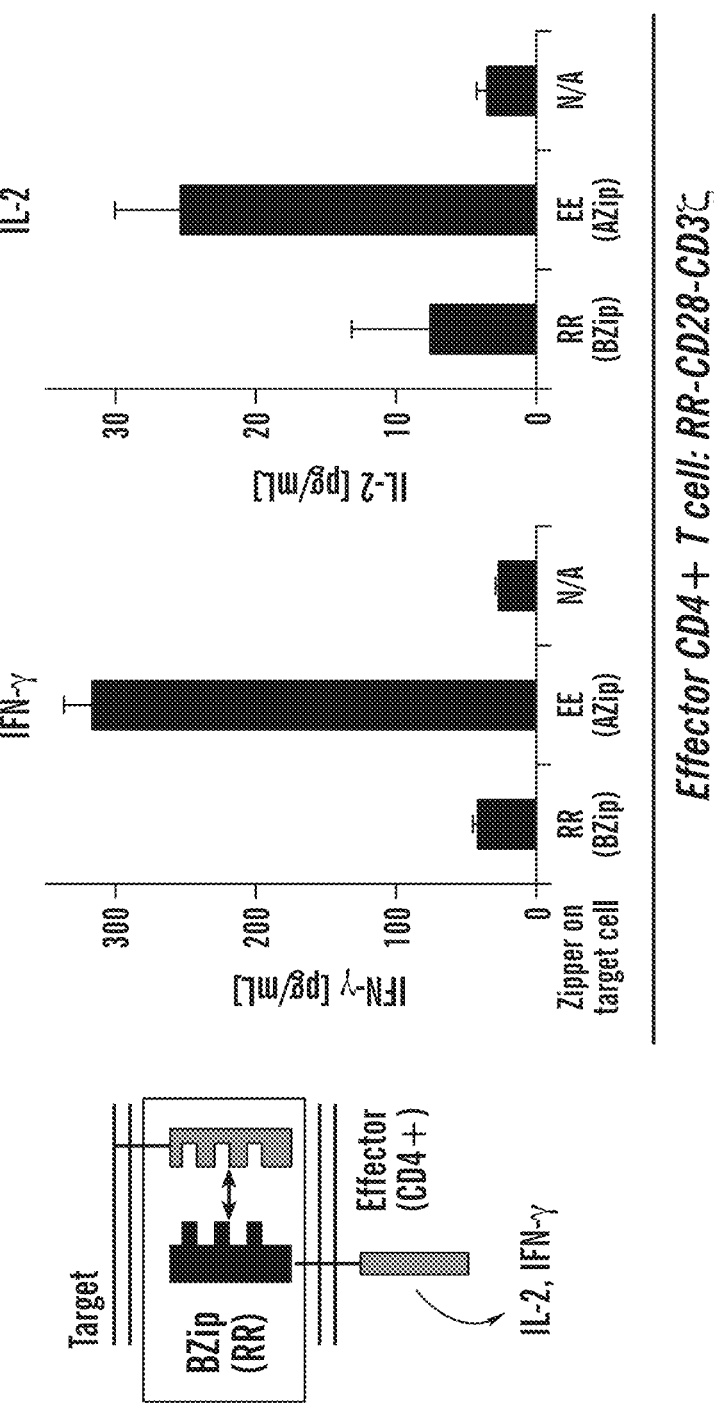
FIG. 4 demonstrates activation of primary CD4 T cells by the zipCAR. IFN-g and IL-2 secretion by the CD4 T cells expressing the BZip(RR) CAR when mixed with cell expressing either the RR or EE zipper. Only cells expressing the EE zipper (the complementary pair to RR) will activate the BZip CAR.

The activity of the SUPRA CAR was tested by transducing primary CD4 T cells with a CAR composed the BZip (RR)[9] as the extracellular domain and signaling domain from CD28, 41BB, and CD3z as the intracellular domains. Jurkat T cell lines expressing either the AZip (EE) or BZip (RR) leucine zipper domains on the surface were also generated. When the cell lines were mixed together, the engineered CD4 T cells expressing zipCAR were able to activate and initiate signaling pathway by interacting with Jurkat T cells expressing the AZip (EE) domain on the surface (FIG. 4).

Figure 5:
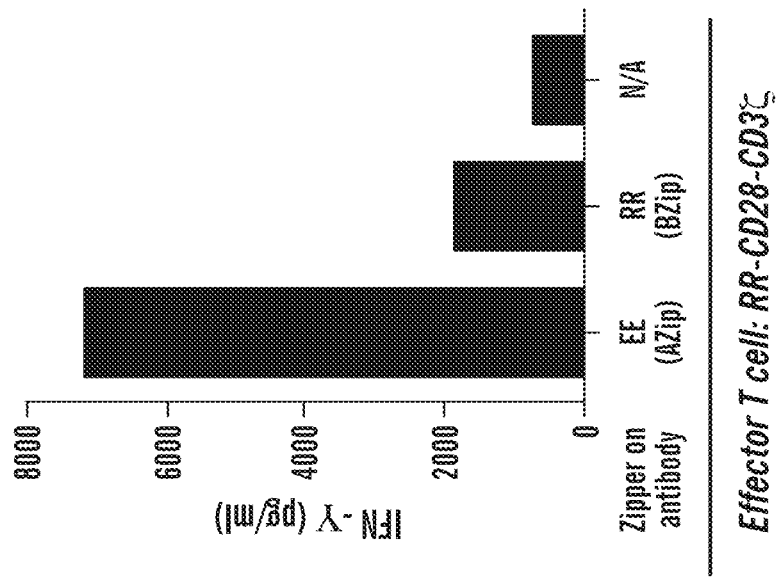
FIG. 5 demonstrates that primary CD4 T cells activation by antibody-zipper fusion and target tumor cells. Anti-Her2-zipper fusion proteins are added to the media containing CD4 T cells modified with RR-CAR and tumor cells expressing Her2. The antibody-zipper fusion protein containing the EE zipper can activate the production of IFN-gamma in primary T cells.
Figure 5:
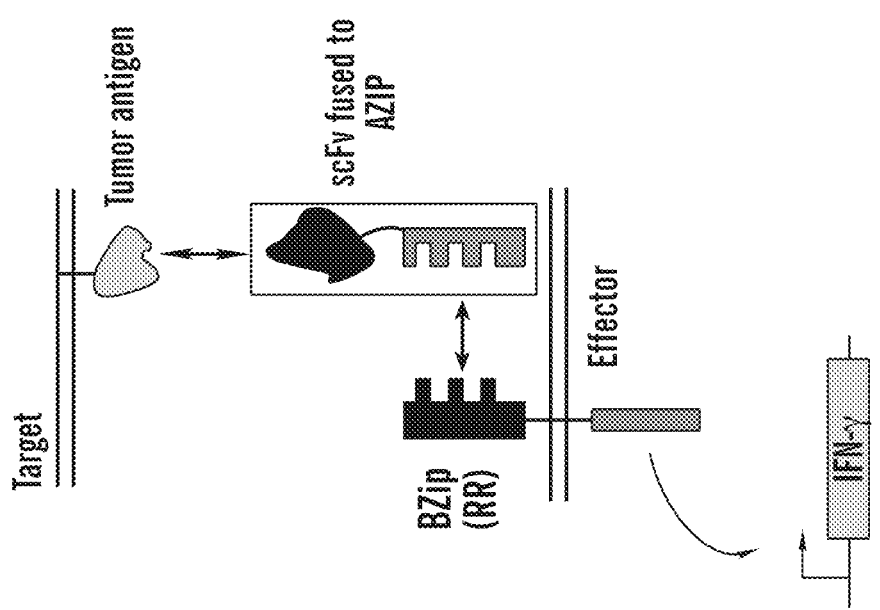
Figure 6A:
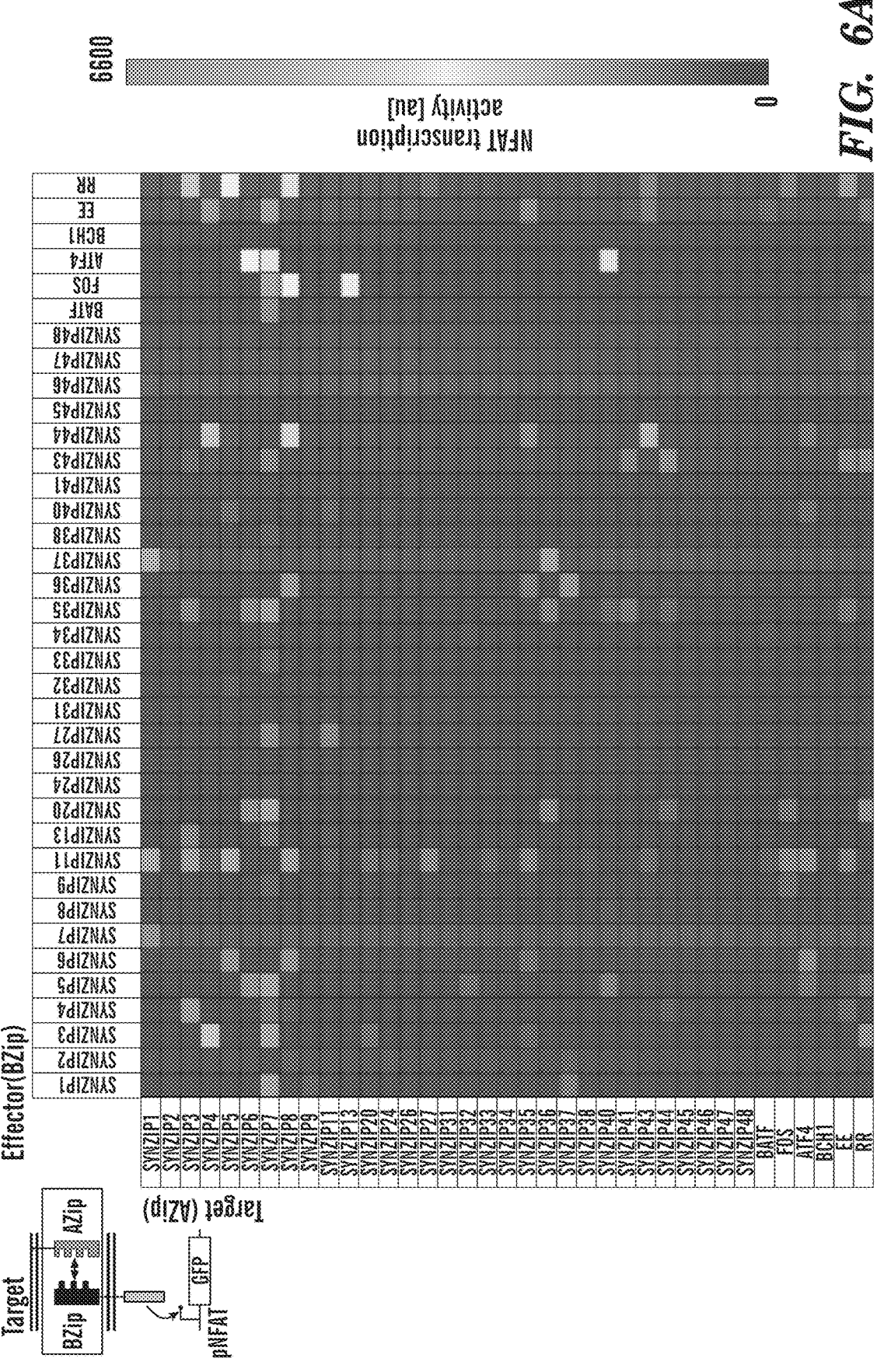
FIGS. 6A-6D depict heatmaps showing the cross-reactivity of 37 leucine zippers in the SUPRA CAR design.
Figure 6B:
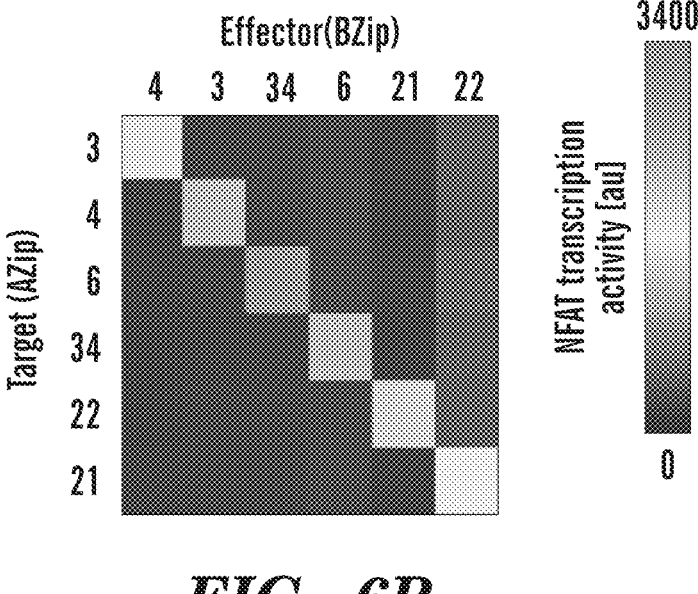
Figure 6C:
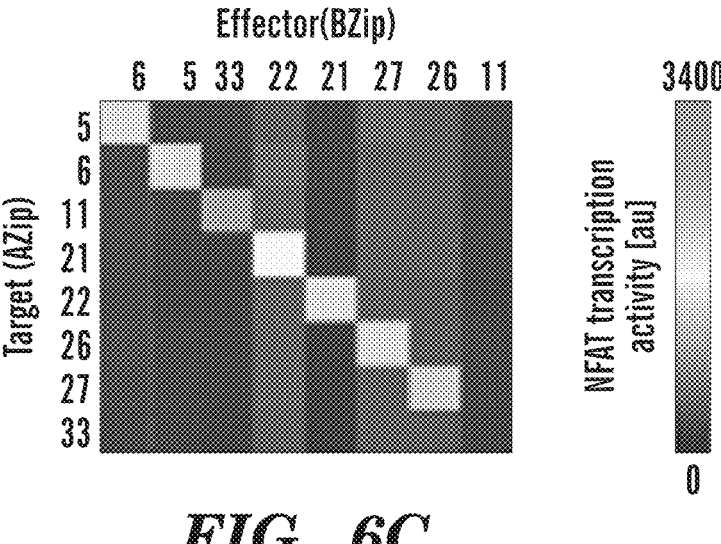
Figure 6D:
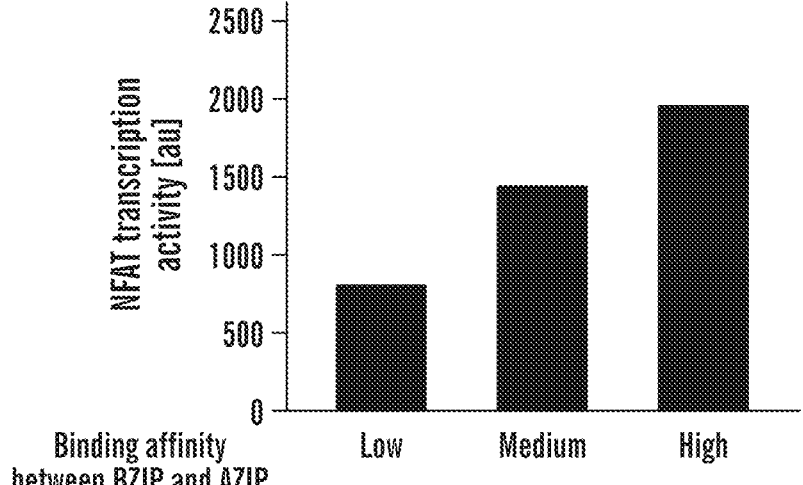
Figure 7:
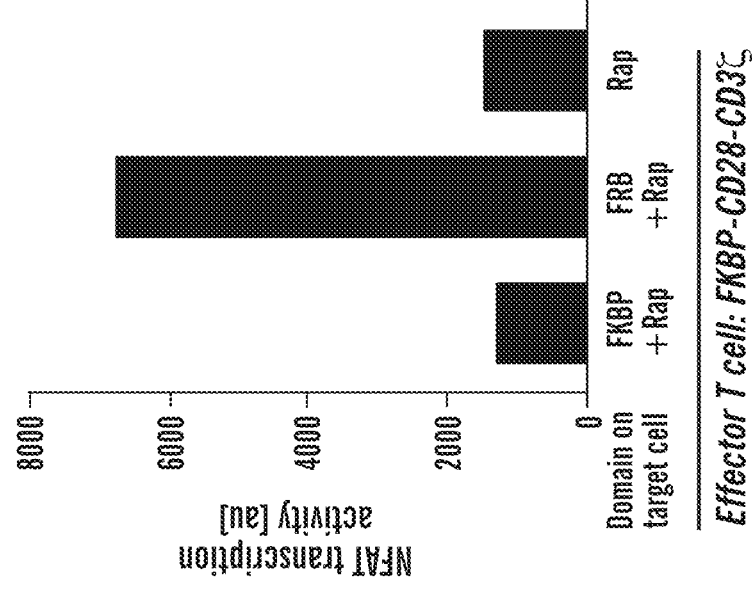
FIG. 7 demonstrates activation of Jurkat T cells expressing an FKBP CAR with small molecular inducer. When this engineered T cells is mixed with target cells expressing FRB on the surface, the addition of small molecule Rapalog leads to the activation of NFAT transcriptional response.
Figure 7:
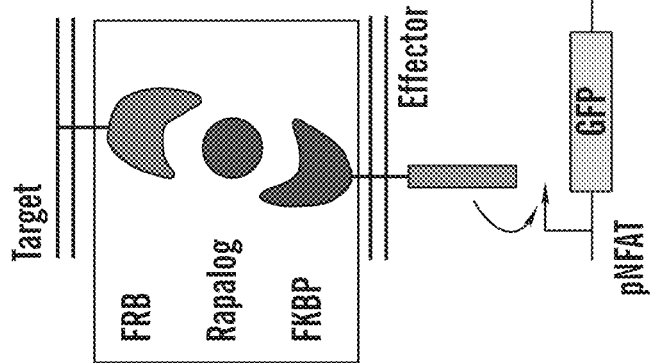

Purified antibodies that contain single chain variable fragment (scFv) targeting HER2 connected to leucine zipper that can bind to zipCARs were produced. BZip CAR (RR) can be activated by purified antibodies in primary CD4+ T cells (measured secreted cytokines) when mixed with Her2 expressing K562 cells (FIG. 5). Moreover, at least 3 orthogonal pairs of leucine zipper pairs that can be used to control different signaling domains (e.g. co-stimulatory, co-inhibitory signaling domains) were identified[10] (FIG. 6a). The signaling domains can be substituted such that different pathways can be controlled independently by the receptors described herein. The affinity of leucine zipper can be varied to control the activation strength. Indeed, it was demonstrated that weaker binding zipper pair leads to weaker activation of T cells (FIGS. 6B, 6D). Lastly, any protein-protein interaction domain can replace the leucine zipper domain such as PDZ domains, SBP(Streptavidin Biding Protein)-Streptavidin, or drug inducible FKBP-FRB pairs, PYL-ABI pair. In fact, it was demonstrated that FKBP and FRB can be used as extracellular recruitment domain and activate T cells with the addition of rapamycin analog (FIG. 7). The FRB domain can be fused to an antibody, thus giving another control over the activation of the T cells. The small molecule drug is less stable, thus can be clear by the body faster then antibody and allow quicker OFF after stopping the drug administration.

Another programmable interaction domain that can be used in the SUPRA platform is the zinc-finger domain. Zinc-finger domains have been expressed on cell surface for barcoding cells with DNA[11]. Furthermore, zinc-finger proteins can be engineered to bind to predefined double stranded DNA sequences with high affinity and specificity. In addition, antibody can be labeled with any DNA sequences using commercially available kits and services. Together, when the DNA-antibody conjugate binds to the antigen on cancer cells, the zinc-finger CAR (zfCAR) can bind to the DNA and trigger T cell activation (FIG. 8A). Moreover, through the development of DNA nanotechnology, DNA can be programmed to perform complex molecular computation that is difficult to duplicate by other systems. For instance, antibodies can be conjugated with different complementary single stranded DNA sequences where only in the presence of all the antibodies will the proper double stranded DNA be formed, which is required for the binding to a zinc-finger protein (FIG. 8B). This configuration represents a multi-input AND gate. By using just three antibodies, it can recognize more antigens than any CAR systems developed. Furthermore, DNA sequences can be made to disrupt double stranded DNAs that bind to zinc-finger domains, thus forming NOT gates. These interruptive DNA sequences can be attached to antibodies that bind to antigens from normal cells, thus preventing T cells from attacking healthy tissues (FIG. 8C). Together, sophisticated logic computation can be achieved in CAR-based therapy. It is demonstrated herein that zfCAR can be activated with DNA (FIG. 8D).

The CAR platform described herein provides at least two distinct advantages over other technologies. First, numerous orthogonal recruitment pairs are readily available from zinc-fingers and leucine zippers. These orthogonal pairs allow independent control of different signaling pathways and fine tuning the T cell signaling to achieve optimal response. Second, the CAR platform described herein can perform complex logic computation through extracellular programmed molecular interaction. This computation capability is almost impossible to achieve in any other forms of therapeutic agents (e.g. biologics and small molecules) and permits extremely high tumor specificity.

REFERENCES

1 Davila, M. L. et al. Efficacy and toxicity management of 19-28z CAR T cell therapy in B cell acute lymphoblastic leukemia. *Science translational medicine* 6, 224ra225, (2014).
2 Grupp, S. A. et al. Chimeric antigen receptor-modified T cells for acute lymphoid leukemia. *N Engl J Med* 368, 1509-1518, (2013).
3 Morgan, R. A. et al. Case report of a serious adverse event following the administration of T cells transduced with a chimeric antigen receptor recognizing ERBB2. *Mol Ther* 18, 843-851, (2010).
4 Kloss, C. C., Condomines, M., Cartellieri, M., Bachmann, M. & Sadelain, M. Combinatorial antigen recognition with balanced signaling promotes selective tumor eradication by engineered T cells. *Nat Biotechnol* 31, 71-75, (2013).
5. Lanitis, E. et al. Chimeric antigen receptor T Cells with dissociated signaling domains exhibit focused antitumor activity with reduced potential for toxicity in vivo. *Cancer Immunol Res* 1, 43-53, (2013).

6 Grada, Z. et al. TanCAR: A Novel Bispecific Chimeric Antigen Receptor for Cancer Immunotherapy. *Mol Ther Nucleic Acids* 2, e105, (2013).

7 Kudo, K. et al. T lymphocytes expressing a CD16 signaling receptor exert antibody-dependent cancer cell killing. *Cancer Res* 74, 93-103, (2014).

8 Urbanska, K. et al. A universal strategy for adoptive immunotherapy of cancer through use of a novel T-cell antigen receptor. *Cancer Res* 72, 1844-1852, (2012).

9 Moll, J. R., Ruvinov, S. B., Pastan, I. & Vinson, C. Designed heterodimerizing leucine zippers with a ranger of pIs and stabilities up to 10(-15) M. *Protein Sci* 10, 649-655, (2001).

10. Reinke, A. W., Grant, R. A. & Keating, A. E. A synthetic coiled-coil interactome provides heterospecific modules for molecular engineering. *J Am Chem Soc* 132, 6025-6031, (2010).

11 Mali, P. et al. Barcoding cells using cell-surface programmable DNA-binding domains. *Nat Methods* 10, 403-406, (2013).

12. Thompson, K E. et al. SYNZIP Protein Interaction Toolbox: in Vitro and in Vivo Specifications of Heterospecific Coiled-Coil Interaction Domains. *ACS Synth. Biol.* 1, 118-129, (2012)

Example 4

Using CRISPR to activate expression of target genes It is possible to overexpress a gene via lentiviral integration of a sequence containing the gene expressed under a constitutive promoter. And while it is conceivable to use this design to overexpress one or two genes that can promote T-cell function in the tumor, the tumor microenvironment may require a more involved system that can overexpress many genes at once to combat the many challenges that limit the T-cell. Using lentivirus integration to directly transduce multiple genes will become inefficient, requiring time for viral integration and screening to ensure the gene has been expressed. In addition, lentiviral integration loses efficiency over multiple rounds of infection, making it a less ideal candidate for integrating a large number of constitutively expressed genes.

It is contemplated herein that CRISPR can be utilized for multiplex expression in T-cells. The Type II CRISPR system relies on a DNA nuclease called Cas9, which cuts targeted sequences of DNA. These targets are defined by a guide RNA (sgRNA), which is complimentary to the targeted DNA sequence. The requirement for targeting is very simple: the target sequence must directly precede a short PAM sequence, which can be as simple as NGG. The gRNA binds to a trans-activating crRNA (tracrRNA) to form a complex that can guide Cas9 to the specified sequence.

Figure 10A:
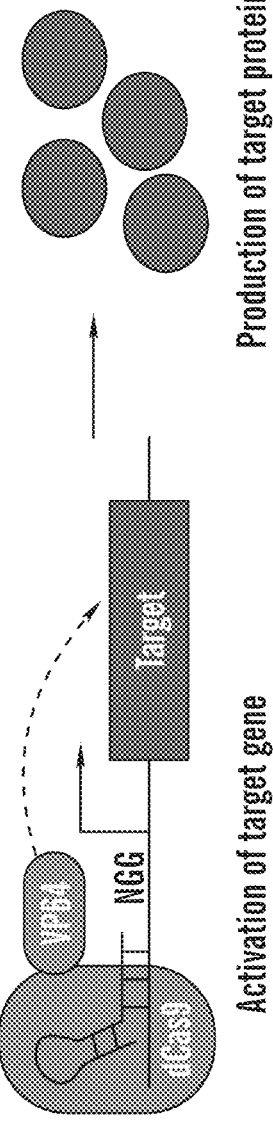
FIGS. 10A-10B depict schematics for the use of the CRISPR system for (FIG. 10A) targeted activation of a gene through dCas9 tagged to an activation domain and (FIG. 10B) multiplexed activation using Csy4 to generate multiple guide RNAs from a single transcript that expresses cleavage sites (CS) between the guide RNAs.
Figure 10B:
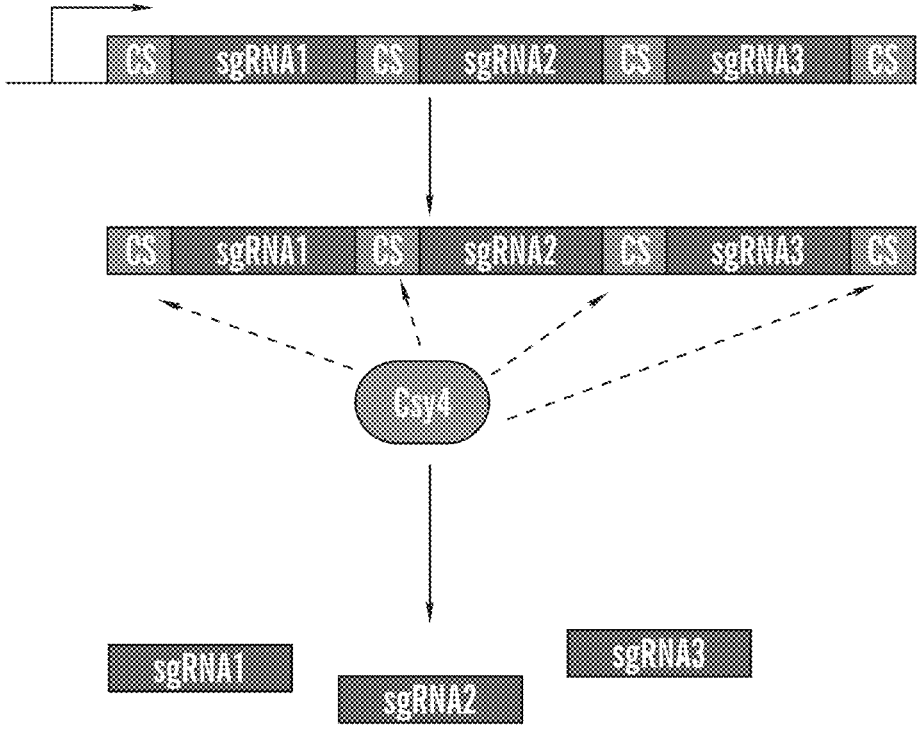

The CRISPR system has been retooled for gene activation by removing the nuclease capability to make a nuclease-deficient Cas9 (dCas9) and attaching it to an activation domain like VP64. In addition, a single guide RNA (sgRNA) has been designed to mimic the gRNA/tracrRNA system so that only one RNA component is required to target the desire sequence. The sgRNA can be designed to target dCas9 towards a promoter, where VP64 can turn on gene expression (FIG. 10A). There are several advantages to using CRISPR to regulate gene expression. As the requirement for a sequence to be targeted is the presence of an adjacent PAM sequence, it is very easy to find many potential targets. In addition, these guide RNAs can be packaged for multiplexed activation using the Type III CRISPR system, which uses an enzyme called Csy4 to cleave RNA at 28-nucleotide long cleavage sites (41). In this system, a single transcript containing all guide RNAs can be expressed under one promoter. The guide RNAs can be spaced apart from each other by the cleavage sites, and Csy4 can cleave the single transcript into distinct guide RNA. Because of the small size of guide RNAs, many can be packaged in one lentiviral plasmid to create a system that leads to the overexpress of multiple genes.

Several genes that affect T-cell activity, proliferation, and apoptosis can be targeted. To promote proliferation, target interleukin-2 (IL-2), which is necessary for growth and proliferation of T-cells and has been used to expand T-cell populations for adoptive T-cell therapy ex vivo (12) can be targeted. In some embodiments, the α chain of the IL-2 receptor, which increases T-cell affinity for IL-2 (42) can be overexpressed. It is also contemplated that T-cell activity can be expressed by over-expressing interleukin-12 (IL-12), which drives CD4 Tcells towards the Th1 phenotype that activates CD8 T-cells (43). Similarly, overexpression of interferon γ (IFN γ), which also promotes the Th1 phenotype and activates macrophages (44), is contemplated.

To contend with the ability of the tumor to promote apoptosis in T-cells, interleukin-15 (IL-15), which induces an apoptosis inhibitor (45), can be overexpressed. In addition to these factors, the α chain of the IL-7 receptor, which promotes CD8T-cell memory, and tumor necrosis factor α (TNFα), a cytokine that inhibits tumorigenesis (46,47), can be overexpressed. Potential sgRNAs to target the endogenous promoters controlling the expressions of each gene can be designed by using the ZiFit web tool to identify sequences adjacent to PAM sequences. The guide RNAs can be designed so that in total, the guide RNAs span the length of the promoter.

The guide RNAs can be expressed, e.g., in Jurkat that are transiently transfected with the individual guide sgRNAs and dCas9-VP64. The expression of the respective genes can be monitored using ELISAs, antibodies, or qRT-PCR depending on the target. It has been observed that using a combination of sgRNAs to target endogenous genes is more effective than the use of a single sgRNA, and combinations that work well to activate a promoter can be identified and tested.

Simulating tumor microenvironment To demonstrate the use of these sgRNAs to increase Tcell activity in a tumor microenvironment, many of the challenges faced by the Tcell in vitro can be simulated. For example, inclusion of TGF-beta and PD-L in the media introduces factors that downregulate T-cell activity. Tryptophan and arginine-depleted media, can stimulate the lack of nutrients in the tumor microenvironment. Additionally, introduction of other cells like Tregs that downregulate T-cell activity, or cells that secrete Indoleamine 2,3-dioxygenase (IDO), which is involved in toxicity against T-cells in the microenvironment, can be useful in simulating the tumor microenvironment. Additionally, a hypoxic, low pH system can be used. The behavior of T-cells in this simulated microenvironment can be determined and compared to cells that express the sgRNAs. Lentiviral integration can be utilized to create stable lines of Jurkat expressing dCas9-VPP64 and the sgRNA combination that best activates the gene. These T-cells can be exposed to the simulated tumor microenvironment and their proliferation and activation compared using T-cell counting, live/dead assays, and monitoring of the CD69 activation marker.

Designing and testing multiplexed activation systems. Combinations of multiplexed factors can be constructed using the Csy4 cleavage system. The three components (dCas9-VP64, Csy4, and multiplexed guide RNA) can be expressed in a lentiviral backbone, adding fluorescent tags to track integration. These constructs can be integrated into Jurkat cells, using the fluorescent tags to sort for cells that have taken up all of the components of the system. The simulated tumor microenvironment and assays developed to measure T-cell activity and proliferation can be used to determine the best combinations to create a better T-cell for tumor microenvironment. Because T-cell signaling is complex and reliant on many interactions between the genes we are targeting, it will be determined whether certain factors are able to act in synergy and whether there is redundancy in targeting two at the same time.

Testing in primary cells and mice Primary cells can be transduced with the multiplexed activation system. Using the simulated T-cell microenvironment and assays tested on Jurkat, T-cell activation can be monitored. In addition, artificial antigen presenting cells can be used to test the ability of primary CD8 T-cells to kill cancer cells in the deprived microenvironment. This system can be further tested in mice to demonstrate that increasing the activity and proliferative ability of T-cells can enhance their ability to kill tumors in vivo.

In some embodiments, reduced transfection efficiency can be addressed by the use of transposons to implement CRISPR or as a method to integrate multiple genes into the T-cell (48).

It is important that the guide RNAs are specific to the promoter of interest. In particular, the observed need for multiple guide RNAs to activate a single gene suggests that CRISPR activation may be specific. In the case that off-target activation is observed, different combinations of sgR-NAs that will be more specific can be identified. Transposon-integration of the desired genes, which will allow for over-expression without gene activation can also be utilized.

Figure 11:
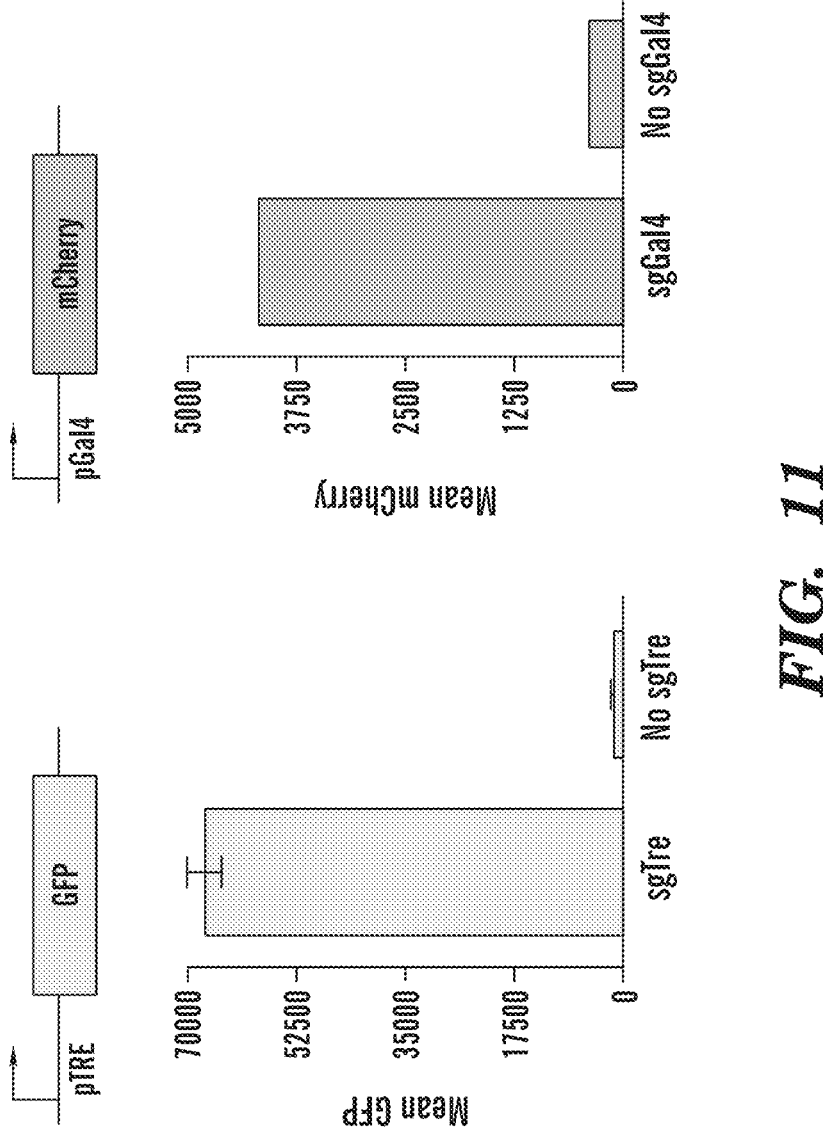
FIG. 11 demonstrates the activation of promoters containing TetO-binding sites (left panel) and Gal4 binding sites (right panel) using a sgRNA targeted towards the promoter and dCas9-VP64.

While increasing the expression of factors that promote activation and proliferation can be helpful in the setting of the tumor microenvironment, the increased activity of the T-cell may trigger a high immune response that is toxic to the surrounding tissue. It will be important to track this issue in a mouse model. One strategy to address this issue is to make dCas9 inducible so that activation of the targeted genes can be controlled. It is demonstrated herein that CRISPR system can activate plasmid genes in Hek, designing guide RNAs to turn on Tet-specific or Gal4-specific promoters (FIG. 11). These results confirmed the use of CRISPR to activate genes in mammalian cells.

REFERENCES

41. Nissim L, Perli S D, Fridkin A, Perez-Pinera P, Lu T. An integrated RNA and CRISPR/Cas toolkit for multiplexed synthetic circuits and endogenous gene regulation in human cells. 2014 April 42. Willerford D M, Chen J, Ferry J A, Davidson L, Ma A. Interleukin-2 receptor a chain regulates the size and content of the peripheral lymphoid compartment. Immunity. 1995.
43. Melero I, Mazzolini G, Narvaiza I, Qian C, Chen L, Prieto J. IL-12 gene therapy for cancer: in synergy with other immunotherapies. 2001 March; 22(3):113-5.
44. Windbichler G H, Hausmaninger H, Stummvoll W, Graf A H, Kainz C, Lahodny J, et al. Interferon-gamma in the first-line therapy of ovarian cancer: a randomized phase III trial. 2000 March; 82(6):1138-44. PMCID: PMC2363351.
45. Klebanoff C A, Finkelstein S E, Surman D R, Lichtman M K, Gattinoni L, Theoret M R, et al. IL-15 enhances the in vivo antitumor activity of tumor-reactive CD8+ T Cells. 2004 Feb. 17; 101(7):1969-74.
46. Kaech S M, Tan J T, Wherry E J, Konieczny B T, Surh C D, Ahmed R. Selective expression of the interleukin 7 receptor identifies effector CD8 T cells that give rise to long-lived memory cells. 2003 Nov. 16; 4(12):1191-8.
47. Lejeune F J, Ruegg C, Lienard D. Clinical applications of TNF-α in cancer. 1998 October; 10(5):573-80.
48. Kahlig K M, Saridey S K, Kaja A, Daniels M A, George A L, Wilson M H. Multiplexed transposon-mediated stable gene transfer in human cells. 2010 Jan. 26; 107(4):1343-8.

Example 5

Figure 13A:
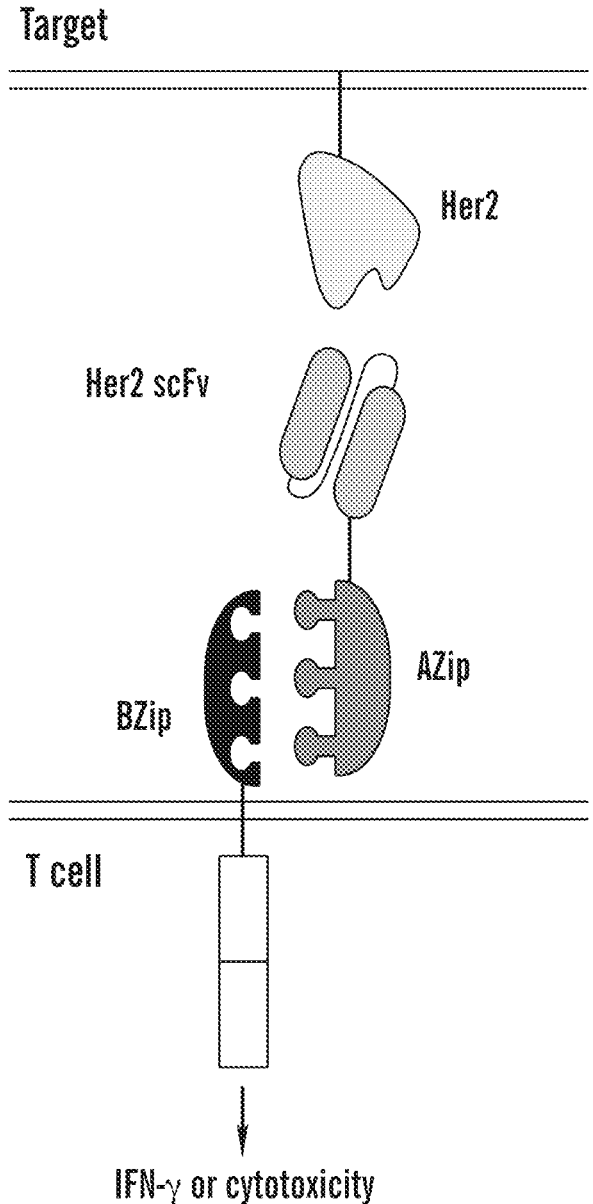
FIGS. 13A-13C demonstrate results of the SUPRA CAR platform in human primary CD4 and CD8 T cells.
Figure 13C:
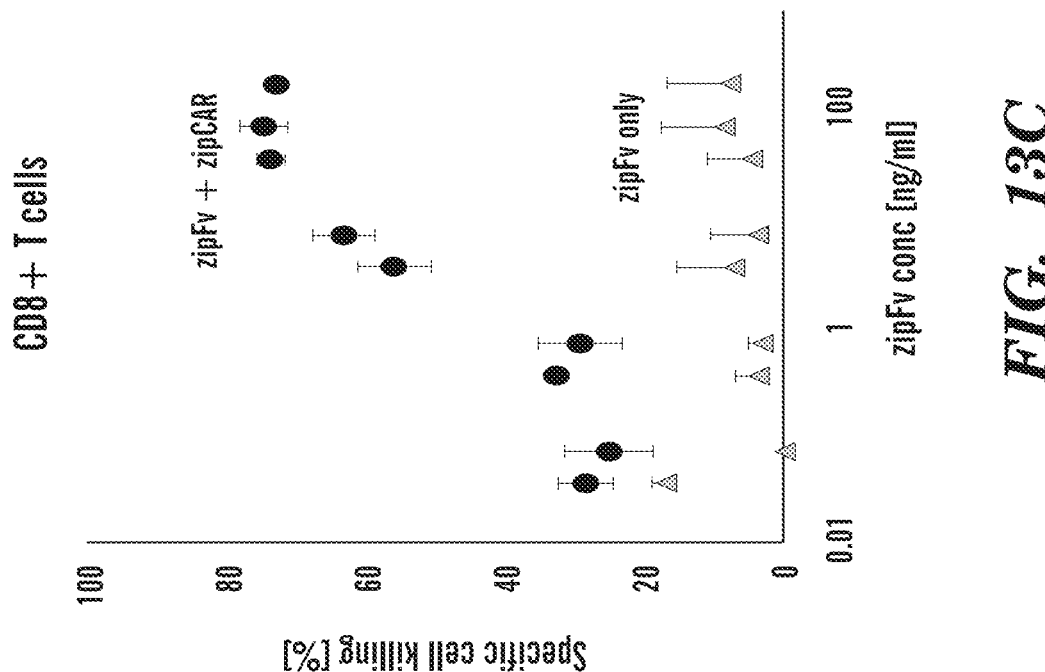
Figure 13B:
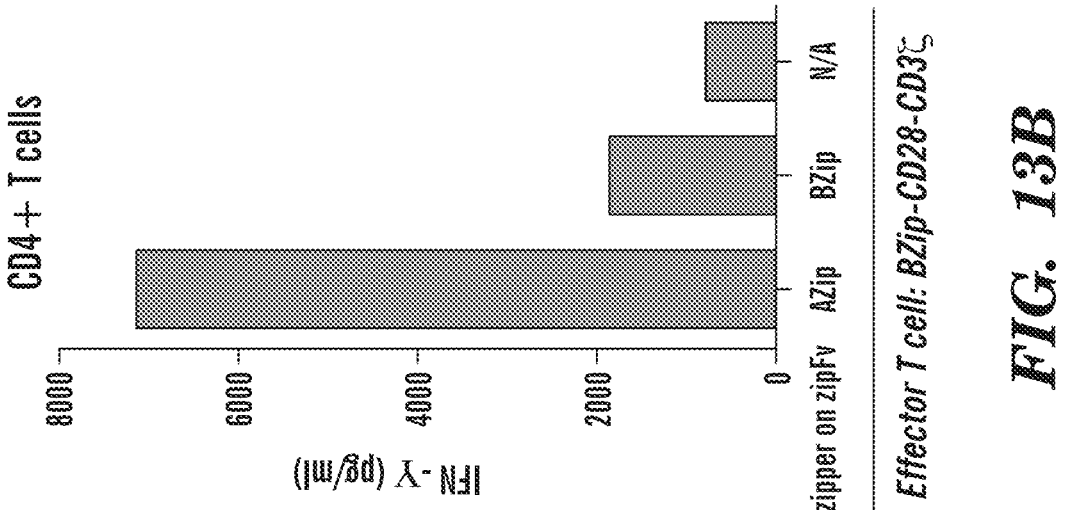

A SUPRA CAR platform by fusing an extracellular BZIP leucine zipper[30] domain to CD28, 4-1BB, and CD3ζ as the intracellular signaling domains. An mCherry fluorescent protein and myc epitope tag were also fused to the BZIP CAR (zipCAR) to facilitate transduction efficiency measurement. The activity of this SUPRA CAR was tested by modifying human primary CD4 T cells with lentivirus containing the zipCAR. A zipFv containing an anti-Her2 scFv connected to an AZIP leucine zipper was purified. This zipFv can bind to the zipCAR and Her2. The zipCAR can be activated by the purified anti-Her2 zipFv in primary CD4+ T cells (as measured by secreted cytokines) when mixed with Her2 expressing K562 cells (FIG. 13A). In contrast, an anti-Her2 zipFv with the BZIP domain did not activate the zipCAR and the T cells. To test the ability of a SUPRA CAR to mediate cytotoxicity against cancer cells, the SUPRA CAR was transduced into human primary CD8 T cells and the SUPRA CAR CD8 T cells mixed with zipFv and K562 cells expressing Her2 (FIG. 13B). As a result, the SUPRA CAR platform is demonstrated herein to lead to the killing of target cancer cells in a dose-dependent manner. zipFv alone did not lead to any significant cell killing, thus confirming that the cell killing is mediated by the engineered T cells and zipCAR.

The affinity of leucine zippers (FIG. 14B) and scFvs (FIG. 14C) was varied to control the activation strength of a zipCAR. By varying the binding affinity of the zipper pair, the response of human primary CD8 T cells equipped with a zipCAR against cancer cells could be modulated. Moreover, it was also demonstrated primary CD8 T cells' killing against target cancer cells could be modulated by varying the scFv affinity to the antigen.

---

What is claimed is:

1. A composition comprising a multi-component chimeric antigen receptor (CAR); the multi-component CAR comprising:

a) a first recognition polypeptide comprising 1) an antibody reagent specific for a first target ligand and 2) a protein interaction domain; and b) a signaling polypeptide comprising 1) an extracellular protein interaction domain that can bind specifically with the protein interaction domain of the first recognition polypeptide, 2) a transmembrane domain, and 3) an intracellular T cell receptor (TCR) signaling domain, wherein one protein interaction domain comprises streptavidin and the other comprises streptavidin binding protein (SBP).

2. The composition of claim 1, further comprising a second recognition polypeptide comprising 1) an antibody reagent specific for a second target ligand and 2) a protein interaction domain that competes with the protein interaction domain of the signaling polypeptide for binding to the protein interaction domain of the first recognition polypeptide.

3. The composition of claim 2, wherein the protein interaction domain of the second recognition polypeptide and the protein interaction domain of the first recognition polypeptide have a greater affinity than the protein interaction domain of the signaling polypeptide and the protein interaction domain of the first recognition polypeptide.

4. The composition of claim 2, wherein the target ligand recognized by the second recognition polypeptide is found on a healthy and/or non-target cell and not on a diseased and/or target cell.

5. The composition of claim 4, wherein the diseased cell is a cancerous cell.

6. The composition of claim 1, further comprising a second recognition polypeptide comprising 1) an antibody reagent specific for a second target ligand and 2) a protein interaction domain; and wherein the signaling polypeptide further comprises a secondary protein interaction domain that specifically binds with the protein interaction domain of the second recognition polypeptide.

7. The composition of claim 6, wherein the affinity of the signaling polypeptide's secondary protein interaction domain and the protein interaction domain of the second recognition polypeptide is weaker than the affinity of the signaling polypeptide's first protein interaction domain and the protein interaction domain of the first recognition polypeptide.

8. The composition of claim 6, wherein the first and second recognition polypeptides each comprise a secondary protein interaction domain; and wherein the secondary protein interaction domains specifically bind to each other.

* * * * *

SEQUENCE LISTING

Sequence total quantity: 3
SEQ ID NO: 1          moltype = DNA  length = 87
FEATURE               Location/Qualifiers

```
misc_feature            1..87
                        note = Description of Artificial Sequence: Synthetic
                         oligonucleotide
source                  1..87
                        mol_type = other DNA
                        organism = synthetic construct
SEQUENCE: 1
cccatgggtg gcataaaatg ggtggcataa aatgggtggc ataaaatggg tggcataaaa   60
tgggtggcat aaaatgggtg gcataaa                                       87

SEQ ID NO: 2            moltype = AA  length = 51
FEATURE                 Location/Qualifiers
REGION                  1..51
                        note = Description of Artificial Sequence: Synthetic
                         polypeptide
source                  1..51
                        mol_type = protein
                        organism = synthetic construct
SEQUENCE: 2
MDPDLEIRAA FLRQRNTALR TEVAELEQEV QRLENEVSQY ETRYGPLGGG K            51

SEQ ID NO: 3            moltype = AA  length = 51
FEATURE                 Location/Qualifiers
REGION                  1..51
                        note = Description of Artificial Sequence: Synthetic
                         polypeptide
source                  1..51
                        mol_type = protein
                        organism = synthetic construct
SEQUENCE: 3
MDPDLEIEAA FLERENTALE TRVAELRQRV QRLRNRVSQY RTRYGPLGGG K            51
```